United States Patent
Polakis et al.

(10) Patent No.: US 9,926,377 B2
(45) Date of Patent: Mar. 27, 2018

(54) ANTI-GPC3 ANTIBODIES AND IMMUNOCONJUGATES

(71) Applicant: GENENTECH, INC., South San Francisco, CA (US)

(72) Inventors: Paul Polakis, Mill Valley, CA (US); Youjun Chen, Redwood City, CA (US)

(73) Assignee: Genentech, Inc., South San Francisco, CA (US)

( * ) Notice: Subject to any disclaimer, the term of this patent is extended or adjusted under 35 U.S.C. 154(b) by 163 days.

(21) Appl. No.: 14/718,932

(22) Filed: May 21, 2015

(65) Prior Publication Data

US 2016/0017049 A1 Jan. 21, 2016

Related U.S. Application Data

(60) Provisional application No. 62/001,868, filed on May 22, 2014.

(51) Int. Cl.
| | |
|---|---|
| C07K 16/00 | (2006.01) |
| C07K 16/30 | (2006.01) |
| A61K 47/48 | (2006.01) |
| A61K 39/395 | (2006.01) |
| A61K 51/10 | (2006.01) |

(52) U.S. Cl.
CPC ...... *C07K 16/303* (2013.01); *A61K 39/39558* (2013.01); *A61K 47/486* (2013.01); *A61K 47/48384* (2013.01); *A61K 47/48407* (2013.01); *A61K 47/48561* (2013.01); *A61K 47/48715* (2013.01); *A61K 51/1057* (2013.01); *C07K 2317/33* (2013.01); *C07K 2317/34* (2013.01); *C07K 2317/77* (2013.01); *G01N 2333/4722* (2013.01)

(58) Field of Classification Search
None
See application file for complete search history.

(56) References Cited

U.S. PATENT DOCUMENTS

| 2007/0087005 A1 | 4/2007 | Lazar et al. | |
| 2007/0172488 A1* | 7/2007 | Aburatani | C07K 16/18 424/155.1 |

FOREIGN PATENT DOCUMENTS

| EP | 1541680 A1 | 6/2005 |
| EP | 2196541 A1 | 6/2010 |
| WO | 2013/070468 A1 | 5/2013 |

OTHER PUBLICATIONS

Chen et al. Reevaluation of glypican-3 as a serological marker for hepatocellular carcinoma. Clinica Chimica Acta 423 (2013) 105-111, Available online May 2, 2013.*
Richard W. Burry, Immunocytochemistry: A Practical Guide for Biomedical Research, Springer Science & Business Media, Dec. 8, 2009—Science. pp. 7-16.*
Owens RJ, Young RJ. The genetic engineering of monoclonal antibodies. J Immunol Methods. 168(2):149-165, 1994.*
Nakatsura et al. Glypican-3, overexpressed specifically in human hepatocellular carcinoma, is a novel tumor marker. Biochemical and Biophysical Research Communications 306 (2003) 16-25.*
Brown et al. Tolerance of single, but not multiple, amino acid replacements in antibody VH CDR 2: a means of minimizing B cell wastage from somatic hypermutation? J. Immuno. May 1996, 3285-91.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Feng et al., "Glypican-3 antibodies: A new therapeutic target for liver cancer" FEBS Letters 588:377-382 (2013).
Feng et al., "Therapeutically targeting glypican-3 via a confirmation-specific single-domain antibody in hepatocellular carcinoma" PNAS 110(12):E1083-E1091 (2013).
Hanaoka et al., "Glypican 3 Targeted Human Heavy Chain Antibody as a Drug Carrier for Hepatocellular Carcinoma Therapy" Mol. Pharmaceutics 12:2151-2157 (2012).
Junutula et al., "Site-specific conjugation of a cytotoxic drug to an antibody improves the therapeutic index" Nat Biotechnol 26(8):925-32 (Aug. 2008).
Lu et al., "Abstract #1233: Development of anti-Glypican 3 therapeutic antibodies" Abstract, 100th AACR Annual Meeting, Denver, CO, p. 296 (Apr. 18-22, 2009).
Nakano et al., "Anti-glypican 3 antibodies cause ADCC against human hepatocellular carcinoma cells" Biochem. Biophys. Res. Comm. 378:279-284 (2009).
Nakano et al., "Generation of a humanized anti-glypican 3 antibody by CDR grafting and stability optimization" Anti-Cancer Drugs 21:907-916 (2010).
Notification of Transmittal of the International Search Report and Written Opinion of the International Searching Authority, or the Declaration, for PCT/US2015/031997 (dated Dec. 10, 2015) (28 pages).
Phung, "High-affinity monoclonal antibodies to cell surface tumor antigen glypican-3 generated through a combination of peptide immunization and flow cytometry screening" mAbs 4(5):592-599 ( 2012).
Yamauchi, "The glypican 3 oncofetal protein is a promising diagnostic marker for hepatocellular carcinoma" Modern Pathology 18:1591-1598 (2005)
Yang et al., "Imaging of hepatocellular carcinoma patient-derived xenografts using $^{89}$Zr-labeled anti-glypican-3 monoclonal antibodies" Biomaterials 35:6964-6971 (2014).
Zhu et al., "First-in-Man Phase I Study of GC33, a Novel Recombinant Humanized Antibody Against Glypican-3, in Patients with Advanced Hepatocellular Carcinoma" Clin. Caner Res. 19(4):920-928 (2013).

* cited by examiner

*Primary Examiner* — Maher M Haddad
(74) *Attorney, Agent, or Firm* — McNeill Baur PLLC

(57) ABSTRACT

The invention provides anti-GPC3 antibodies and immunoconjugates and methods of using the same.

26 Claims, 18 Drawing Sheets

Heavy chain variable region

| Kabat number | 1 2 3 4 5 6 7 8 9 10 11 12 13 14 15 16 17 18 19 20 21 22 23 24 25 26 27 28 29 30 31 32 33 34 35 36 37 38 39 40 41 42 |
|---|---|
| 7H1  | Q V Q L Q Q S G P E L V K P G A S V R M S C K A S G Y T F T D Y Y I N W V K Q R P G |
| 4A11 | E V Q L Q Q S G A A E L A R P G A S V K L S C K A S G Y T F T S G F W M S W V K Q R P G |
| 15G1 | E V Q L Q Q S G T V L A R P G G S V K M S C K A S G Y T F T S Y W M H W V K Q R P G |
| 4G7  | E V Q L Q Q S G T V L A R P G A S V K M S C K A S G Y T F T S Y W M H W V K Q R P G |

CDR H1 - Contact: positions 30-35
CDR H1 - Kabat: positions 31-35

| Kabat number | 43 44 45 46 47 48 49 50 51 52 52a 53 54 55 56 57 58 59 60 61 62 63 64 65 66 67 68 69 70 71 72 73 74 75 76 77 78 79 80 81 82a |
|---|---|
| 7H1  | Q G L E W I G W I Y P G S G H T E Y N E T F K G K A T L T V D T S S S T A Y M Q L S |
| 4A11 | Q G L E W I G Y I N P N S D G S S Y N Q K F K D R F T I T A D K S S N T A Y M Q L S |
| 15G1 | K T L E W I G D I N — P A S Y N Q K F K G K A T L T V D K S S S T A Y M Q L Y L Q M T |
| 4G7  | Q G L E W I G A I Y P G N I D A S Y N Q K F K G K A K L T A V T S T A Y M E L S |

CDR H2 - Contact
CDR H2 - Kabat

| Kabat number | 82b 82c 83 84 85 86 87 88 89 90 91 92 93 94 95 96 97 98 99 100 100a 100b 100c 100d 101 102 103 104 105 106 107 108 109 110 111 112 113 | SEQ ID NO: |
|---|---|---|
| 7H1  | S L T S E D T A V Y F C T R G Y Y A P M G Y F D Y W G Q G T T L T V S S | 2 |
| 4A11 | S L T S E D S A V Y Y C T R N F — — — — — D Y W G Q G T T L T V S S | 10 |
| 15G1 | N V R S E D T G T Y F C V T T Y G — — — — D Y W G Q G T T L T V S S | 18 |
| 4G7  | S L T N E D S A V Y Y C S Y D Y D A W F — — — V Y W G Q G T L V T V S A | 26 |

CDR H3 - Contact
CDR H3 - Kabat

FIG. 4A

Light chain variable region

| Kabat number | Sequence (positions 1–42) |
|---|---|
| 7H1 | D I Q M T Q S P S S L S A S V G D R V S I T C K A S Q D I — S Y L S W F Q Q K P G K |
| 4A11 | D I V M T Q S P S S M Y A S L G E R V T I T C K A S Q N V G T N V A W Y Q Q K P G Q |
| 15G1 | D I V M T Q S Q K F M S T S V G D R V S I T C K A S Q D V S T A V A W Y Q Q K P G Q |
| 4G7 | D I Q M T Q S H K F M S T S V G D R V S I T C K A S Q D V S T A V A W Y Q Q K P G Q |

CDR L1 – Contact / CDR L1 – Kabat

| Kabat number | Sequence (positions 43–86) |
|---|---|
| 7H1 | T K R L I Y A A S T L D S G V P S R F S G S G S G T D F T L T I S S L Q S E D F A |
| 4A11 | S P K T L L I Y R N R L V D G V P D R F T G S G S G T D F T L T I S S V Q A E D L A |
| 15G1 | S P K A L L I Y S A S N R Y T G V P D R F T G S G S G T D F T F T I S S V Q A E D L A |
| 4G7 | S P T L L I Y S A S Y R Y T G V P D R F T G S G S G T D F T F T I S S V Q A E D L A |

CDR L2 – Contact / CDR L2 – Kabat

| Kabat number | Sequence (positions 87–107) | SEQ ID NO: |
|---|---|---|
| 7H1 | D Y Y C L Q Y A S Y P Y T F G Q G T K L E I K | 3 |
| 4A11 | I Y Y C Q Q Y D E F P L T F G A G T K L E L K | 11 |
| 15G1 | E Y F C Q Q Y H I Y P Y T F G Q G T R L E I K | 19 |
| 4G7 | V Y Y C Q Q H Y F T P R T F G G G T K L E L K | 27 |

CDR L3 – Contact / CDR L3 – Kabat

FIG. 4B

```
human    MAGTVRTACLVVAMLLSLDFPGQAQPPPPPPPDATCHQVRSFFQRLQPGLKWVPETPVPGS
cyno     MAGTVRTACLVVAMLLSLDFPGQAQPPPPPPPDATCHQVRSFFQRLQPGLKWVPETPVPGS
rhesus   MAGTVRTACLVVAMLLSLDFPGQAQPPPPPPPDATCHQVRSFFQRLQPGLKWVPETPVPGS
mouse    MAGTVRTACLLVAMLLGLGCLGQAQPP-PPPDATCHQVRSFFQRLQPGLKWVPETPVPGS
rat      MAGTVRTACLLVAMLLGLGCLGQAQPP-PPPDATCHQVRSFFQRLQPGLKWVPETPVPGS
         ********:***.*      **** ******************************* human    DLQVCLPKGPTCCSRKMEEKYQLTARLNMEQLLQSASMELKFLIIQNAAVFQEAFEIVVR
cyno     DLQVCLPKGPTCCSRKMEEKYQLTARLNMEQLLQSASMELKFLIIQNAAVFQEAFEIVVR
rhesus   DLQVCLPKGPTCCSRKMEEKYQLTARLNMEQLLQSASMELKFLIIQNAAVFQEAFEIVVR
mouse    DLQVCLPKGPTCCSRKMEEKYQLTARLNMEQLLQSASMELKFLIIQNAAVFQEAFEIVVR
rat      DLQVCLPKGPTCCSRKMEEKYQLTARLNMEQLLQSASMELKFLIIQNAAVFQEAFEIVVR
         ************************************************************
                      7H1 epitope (aa 25-137)
human    HAKNYTNAMFKNNYPSLTPQAFEFVGEFFTDVSLYILGSDINVDDMVNELFDSLFPVIYT
cyno     HAKNYTNAMFKNNYPSLTPQAFEFVGEFFTDVSLYILGSDINVDDMVNELFDSLFPVIYT
rhesus   HAKNYTNAMFKNNYPSLTPQAFEFVGEFFTDVSLYILGSDINVDDMVNELFDSLFPVIYT
mouse    HAKNYTNAMFKNNYPSLTPQAFEFVGEFFTDVSLYILGSDINVDDMVNELFDSLFPVIYT
rat      HAKNYTNAMFKNNYPSLTPQAFEFVGEFFTDVSLYILGSDINVDDMVNELFDSLFPVIYT
         ************************************************************ human    QLMNPGLPDSALDINECLRGARRDLKVFGNFPKLIMTQVSKSLQVTRIFLQALNLGIEVI
cyno     QLMNPGLPDSALDINECLRGARRDLKVFGNFPKLIMTQVSKSLQVTRIFLQALNLGIEVI
rhesus   QLMNPGLPDSALDINECLRGARRDLKVFGNFPKLIMTQVSKSLQVTRIFLQALNLGIEVI
mouse    QMMNPGLPESVLDINECLRGARRDLKVFGSFPKLIMTQVSKSLQVTRIFLQALNLGIEVI
rat      QMMNPGLPESVLDINECLRGARRDLKVFGSFPKLIMTQVSKSLQVTRIFLQALNLGIEVI
         *:******:*.***************.***************************** human    NTTDHLKFSKDCGRMLTRMWYCSYCQGLMMVKPCGGYCNVVMQGCMAGVVEIDKYWREYI
cyno     NTTDHLKFSKDCGRMLTRMWYCSYCQGLMMVKPCGGYCNVVMQGCMAGVVEIDKYWREYI
rhesus   NTTDHLKFSKDCGRMLTRMWYCSYCQGLMMVKPCGGYCNVVMQGCMAGVVEIDKYWREYI
mouse    NTTDHLKFSKDCGRMLTRMWYCSYCQGLMMVKPCGGYCNVVMQGCMAGVVEIDKYWREYI
rat      NTTDHLKFSKDCGRMLTRMWYCSYCQGLMMVKPCGGYCNVVMQGCMAGVVEIDKYWREYI
         ************************************************************ human    LSLEELVNGMYRIYDMENVLLGLFSTIHDSIQYVQKNAGKLTTTIGKLCAHSQQRQYRSA
cyno     LSLEELVNGMYRIYDMENVLLGLFSTIHDSIQYVQKNAGKLTTTIGKLCAHSQQRQYRSA
rhesus   LSLEELVNGMYRIYDMENVLLGLFSTIHDSIQYVQKNAGKLTTTIGKLCAHSQQRQYRSA
mouse    LSLEELVNGMYRIYDMENVLLGLFSTIHDSIQYVQKNGGKLTTTIGKLCAHSQQRQYRSA
rat      LSLEELVNGMYRIYDMENVLLGLFSTIHDSIQYVQKNGGKLTTTIGKLCAHSQQRQYRSA
         ************************************.***********************
                                           Furin cleavage / 4G7 epitope
human    YYPEDLFIDKKVLKVAHVEHEETLSSRRRELIQKLKSFISFYSALPGYICSHSPVAENDT
cyno     YYPEDLFIDKKVLKVAHVEHEETLSSRRRELIQKLKSFISFYSALPGYICSHSPVAENDT
rhesus   YYPEDLFIDKKVLKVAHVEHEETLSSRRRELIQKLKSFISFYSALPGYICSHSPVAENDT
mouse    YYPEDLFIDKKVLKVARVEHEETLSSRRRELIQKLKSFINFYSALPGYICSHSPVAENDT
rat      YYPEDLFIDKKVLKVARVEHEETLSSRRRELIQKLKSFISFYSALPGYICSHSPVAENDT
         ****************.*********************.*********************
```

FIG. 11

```
human    LCWNGQELVERYSQKAARNGMKNQFNLHELKMKGPEPVVSQIIDKLKHINQLLRTMSMPK
cyno     LCWNGQELVERYSQKAARNGMKNQFNLHELKMKGPEPVVSQIIDKLKHINQLLRTMSVPK
rhesus   LCWNGQELVERYSQKAARNGMKNQFNLHELKMKGPEPVVSQIIDKLKHINQLLRTMSVPK
mouse    LCWNGQELVERYSQKAARNGMKNQFNLHELKMKGPEPVVSQIIDKLKHINQLLRTMSVPK
rat      LCWNGQELVERYSQKAARNGMKNQFNLHELKMKGPEPVVSQIIDKLKHINQLLRTMSVPK
         ************************************************** :**
```
15G1 epitope (aa 420-470)

```
human    GRVLDKNLDEEGFESGDCGDDEDECIGGSGDGMIKVKNQLRFLAELAYDLDVDDAPGNSQ
cyno     GRVLDKNLDEEGFESGDCGDDEDECIGGSGDGMMKVKNQLRFLAELAYDLDVDDVPGNNQ
rhesus   GRVLDKNLDEEGFESGDCCDDEDECIGGSGDGMMKVKNQLRFLAELAYDLDVDDVPGNNQ
mouse    GKVLDKSLDEEGLESGDCGDDEDECIGGSGDGMVKVKNQLRFLAELAYDLDVDDAPGNKQ
rat      GKVVDKSLDEEGLESGDCGDDEDECIGSSGDGMMKVKNQLRFLAELAYDLDVDDAPGNKQ
         *:*:** ***** .***************.*****:******************.*** *
```
4A11 epitope (aa 470-509)    Santa Cruz 1G12 immunogen (aa 511-580)

```
human    QATPKDNEISTFHNLGNVHSPLKLLTSMAISVVCFFFLVH     SEQ ID NO: 1
cyno     QATPKDNEISTFHNLGNVHSPLKLLTSMAISVVCFFFLVH     SEQ ID NO: 37
rhesus   QATPKDNEISTFHNLGNVHSPLKLLTSMAISVVCFFFLVH     SEQ ID NO: 38
mouse    HGNQKDNEITTSHSVGNMPSPLKILISVAIYVACFFFLVH     SEQ ID NO: 39
rat      HGNQKDNEITTSHSVGNMPSPLKILISVAIYVACFFFLVH     SEQ ID NO: 40
         :.. *****:* *.:** **** *:** *.*******
```

FIG. 11 (cont.)

*FIG. 12A*  maleimide acetal PNU-159682 antibody-drug conjugate
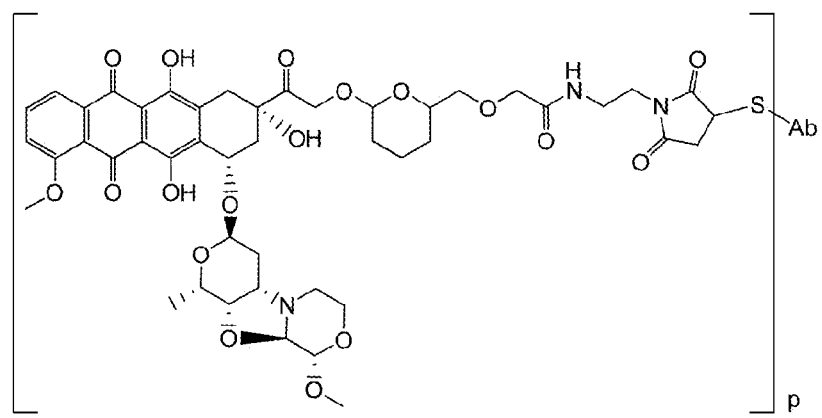
*FIG. 12B*  monomethyl disulfide N10-linked PBD antibody-drug conjugate
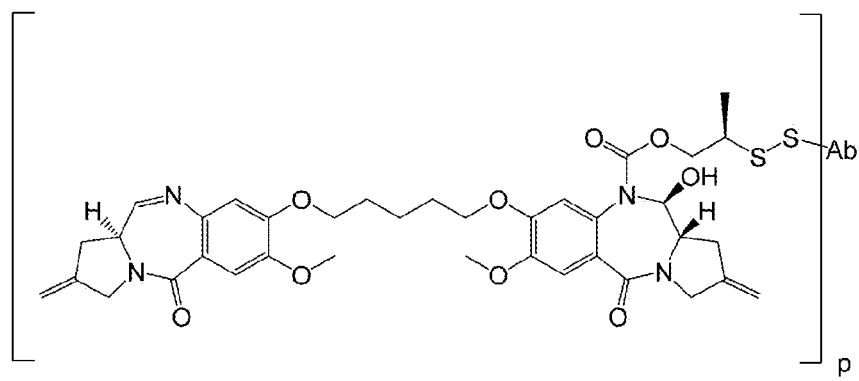

FIG. 13A
FIG. 13B
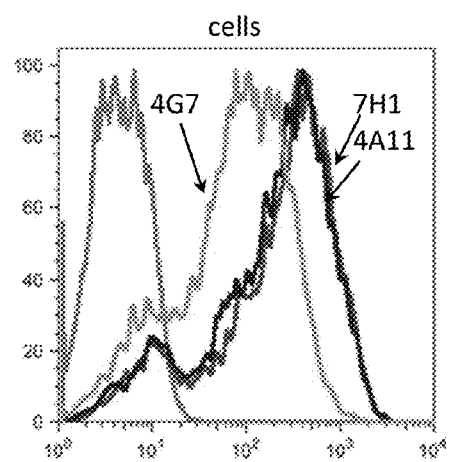
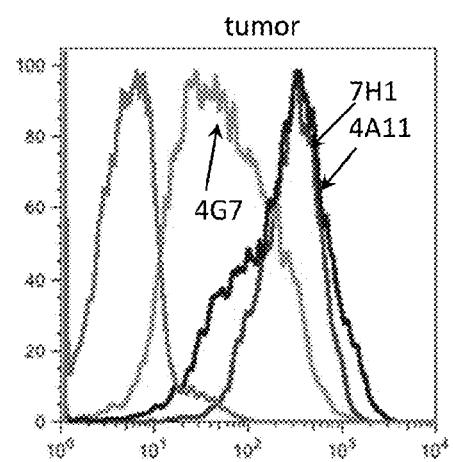

SEQUENCE LISTING

<160> NUMBER OF SEQ ID NOS: 48

<210> SEQ ID NO 1
<211> LENGTH: 580
<212> TYPE: PRT
<213> ORGANISM: Homo sapiens

<400> SEQUENCE: 1

```
Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
            20                  25                  30

Ala Thr Cys His Gln Val Arg Ser Phe Phe Gln Arg Leu Gln Pro Gly
        35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110

Glu Ala Phe Glu Ile Val Val Arg His Ala Lys Asn Tyr Thr Asn Ala
        115                 120                 125

Met Phe Lys Asn Asn Tyr Pro Ser Leu Thr Pro Gln Ala Phe Glu Phe
    130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
            180                 185                 190

Asp Ile Asn Glu Cys Leu Arg Gly Ala Arg Arg Asp Leu Lys Val Phe
        195                 200                 205

Gly Asn Phe Pro Lys Leu Ile Met Thr Gln Val Ser Lys Ser Leu Gln
    210                 215                 220

Val Thr Arg Ile Phe Leu Gln Ala Leu Asn Leu Gly Ile Glu Val Ile
```

```
                    225                 230                 235                 240
Asn Thr Thr Asp His Leu Lys Phe Ser Lys Asp Cys Gly Arg Met Leu
                    245                 250                 255

Thr Arg Met Trp Tyr Cys Ser Tyr Cys Gln Gly Leu Met Met Val Lys
                    260                 265                 270

Pro Cys Gly Gly Tyr Cys Asn Val Met Gln Gly Cys Met Ala Gly
                    275                 280                 285

Val Val Glu Ile Asp Lys Tyr Trp Arg Glu Tyr Ile Leu Ser Leu Glu
                    290                 295                 300

Glu Leu Val Asn Gly Met Tyr Arg Ile Tyr Asp Met Glu Asn Val Leu
305                 310                 315                 320

Leu Gly Leu Phe Ser Thr Ile His Asp Ser Ile Gln Tyr Val Gln Lys
                    325                 330                 335

Asn Ala Gly Lys Leu Thr Thr Thr Ile Gly Lys Leu Cys Ala His Ser
                    340                 345                 350

Gln Gln Arg Gln Tyr Arg Ser Ala Tyr Tyr Pro Glu Asp Leu Phe Ile
                    355                 360                 365

Asp Lys Lys Val Leu Lys Val Ala His Val Glu His Glu Thr Leu
370                 375                 380

Ser Ser Arg Arg Arg Glu Leu Ile Gln Lys Leu Lys Ser Phe Ile Ser
385                 390                 395                 400

Phe Tyr Ser Ala Leu Pro Gly Tyr Ile Cys Ser His Ser Pro Val Ala
                    405                 410                 415

Glu Asn Asp Thr Leu Cys Trp Asn Gly Gln Glu Leu Val Glu Arg Tyr
                    420                 425                 430

Ser Gln Lys Ala Ala Arg Asn Gly Met Lys Asn Gln Phe Asn Leu His
                    435                 440                 445

Glu Leu Lys Met Lys Gly Pro Glu Pro Val Val Ser Gln Ile Ile Asp
                    450                 455                 460

Lys Leu Lys His Ile Asn Gln Leu Leu Arg Thr Met Ser Met Pro Lys
465                 470                 475                 480

Gly Arg Val Leu Asp Lys Asn Leu Asp Glu Glu Gly Phe Glu Ser Gly
                    485                 490                 495

Asp Cys Gly Asp Asp Glu Asp Glu Cys Ile Gly Gly Ser Gly Asp Gly
                    500                 505                 510

Met Ile Lys Val Lys Asn Gln Leu Arg Phe Leu Ala Glu Leu Ala Tyr
                    515                 520                 525

Asp Leu Asp Val Asp Asp Ala Pro Gly Asn Ser Gln Gln Ala Thr Pro
                    530                 535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                    565                 570                 575

Phe Leu Val His
            580

<210> SEQ ID NO 2
<211> LENGTH: 120
<212> TYPE: PRT
<213> ORGANISM: Mus musculus

<400> SEQUENCE: 2

Gln Val Gln Leu Gln Gln Ser Gly Pro Glu Leu Val Lys Pro Gly Ala
1               5                   10                  15
```

```
Ser Val Lys Ile Ser Cys Lys Ala Ser Gly Tyr Thr Phe Thr Asp Tyr
            20                  25                  30

Tyr Ile Asn Trp Val Lys Gln Lys Pro Gly Gln Gly Leu Glu Trp Ile
            35                  40                  45

Gly Trp Ile Tyr Pro Gly Ser Gly His Thr Glu Cys Asn Glu Thr Phe
50                      55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Thr Arg Gly Tyr Tyr Ala Pro Met Gly Tyr Phe Asp Tyr Trp Gly Gln
            100                 105                 110

Gly Thr Thr Leu Thr Val Ser Ser
            115                 120

<210> SEQ ID NO 3
<211> LENGTH: 107
<212> TYPE: PRT
<213> ORGANISM: Mus musculus

<400> SEQUENCE: 3

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
            35                  40                  45

Tyr Ala Ala Ser Thr Leu Asp Ser Gly Val Pro Lys Arg Phe Ser Gly
50                  55                  60

Ser Arg Ser Gly Ser Asp Tyr Ser Leu Thr Ile Ser Gly Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Gly Gly Thr Lys Leu Glu Ile Lys
            100                 105

<210> SEQ ID NO 4
<211> LENGTH: 5
<212> TYPE: PRT
<213> ORGANISM: Mus musculus

<400> SEQUENCE: 4

Asp Tyr Tyr Ile Asn
1               5

<210> SEQ ID NO 5
<211> LENGTH: 17
<212> TYPE: PRT
<213> ORGANISM: Mus musculus

<400> SEQUENCE: 5

Trp Ile Tyr Pro Gly Ser Gly His Thr Glu Cys Asn Glu Thr Phe Lys
1               5                   10                  15

Gly

<210> SEQ ID NO 6
<211> LENGTH: 11
<212> TYPE: PRT
<213> ORGANISM: Mus musculus
```

```
<400> SEQUENCE: 6

Gly Tyr Tyr Ala Pro Met Gly Tyr Phe Asp Tyr
1               5                   10

<210> SEQ ID NO 7
<211> LENGTH: 11
<212> TYPE: PRT
<213> ORGANISM: Mus musculus

<400> SEQUENCE: 7

Arg Ala Ser Gln Glu Ile Ser Gly Tyr Leu Ser
1               5                   10

<210> SEQ ID NO 8
<211> LENGTH: 7
<212> TYPE: PRT
<213> ORGANISM: Mus musculus

<400> SEQUENCE: 8

Ala Ala Ser Thr Leu Asp Ser
1               5

<210> SEQ ID NO 9
<211> LENGTH: 9
<212> TYPE: PRT
<213> ORGANISM: Mus musculus

<400> SEQUENCE: 9

Leu Gln Tyr Ala Ser Tyr Pro Tyr Thr
1               5

<210> SEQ ID NO 10
<211> LENGTH: 113
<212> TYPE: PRT
<213> ORGANISM: Mus musculus

<400> SEQUENCE: 10

Glu Val Gln Leu Gln Gln Ser Ala Ala Glu Leu Ala Arg Pro Gly Ala
1               5                   10                  15

Ser Val Arg Met Ser Cys Arg Thr Ser Gly Tyr Thr Phe Thr Thr Tyr
                20                  25                  30

Thr Ile His Trp Met Lys Gln Arg Pro Gly Gln Gly Leu Glu Trp Ile
            35                  40                  45

Gly Tyr Ile Asn Pro Asn Gly Gly Tyr Thr Glu Tyr Asn Gln Lys Phe
        50                  55                  60

Arg Asp Arg Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asn Phe Asp Tyr Trp Gly Gln Gly Thr Thr Leu Thr Val Ser
                100                 105                 110

Ser

<210> SEQ ID NO 11
<211> LENGTH: 107
<212> TYPE: PRT
<213> ORGANISM: Mus musculus

<400> SEQUENCE: 11

Asp Ile Val Met Thr Gln Ser Pro Ser Ser Met Tyr Ala Ser Leu Gly
```

```
            1               5                  10                 15
        Glu Arg Val Thr Ile Thr Cys Lys Ala Ser Gln Asp Ile Asn Ser Tyr
                        20                 25                 30
        Leu Ser Trp Phe Gln Gln Lys Pro Gly Lys Ser Pro Lys Thr Leu Ile
                        35                 40                 45
        Tyr Arg Val Asn Arg Leu Val Asp Gly Val Pro Ser Arg Phe Ser Gly
                        50                 55                 60
        Ser Gly Ser Gly Gln Asp Tyr Ser Leu Thr Ile Ser Ser Leu Glu Tyr
        65                     70                 75                 80
        Glu Asp Val Gly Ile Tyr Tyr Cys Leu Gln Tyr Asp Glu Phe Pro Leu
                        85                 90                 95
        Thr Leu Gly Ala Gly Thr Lys Leu Glu Leu Lys
                        100                105
```

<210> SEQ ID NO 12
<211> LENGTH: 5
<212> TYPE: PRT
<213> ORGANISM: Mus musculus

<400> SEQUENCE: 12

```
Thr Tyr Thr Ile His
1               5
```

<210> SEQ ID NO 13
<211> LENGTH: 17
<212> TYPE: PRT
<213> ORGANISM: Mus musculus

<400> SEQUENCE: 13

```
Tyr Ile Asn Pro Asn Gly Gly Tyr Thr Glu Tyr Asn Gln Lys Phe Arg
1               5                   10                  15
Asp
```

<210> SEQ ID NO 14
<211> LENGTH: 4
<212> TYPE: PRT
<213> ORGANISM: Mus musculus

<400> SEQUENCE: 14

```
Asn Phe Asp Tyr
1
```

<210> SEQ ID NO 15
<211> LENGTH: 11
<212> TYPE: PRT
<213> ORGANISM: Mus musculus

<400> SEQUENCE: 15

```
Lys Ala Ser Gln Asp Ile Asn Ser Tyr Leu Ser
1               5                   10
```

<210> SEQ ID NO 16
<211> LENGTH: 7
<212> TYPE: PRT
<213> ORGANISM: Mus musculus

<400> SEQUENCE: 16

```
Arg Val Asn Arg Leu Val Asp
1               5
```

<210> SEQ ID NO 17

```
<211> LENGTH: 9
<212> TYPE: PRT
<213> ORGANISM: Mus musculus

<400> SEQUENCE: 17

Leu Gln Tyr Asp Glu Phe Pro Leu Thr
1               5

<210> SEQ ID NO 18
<211> LENGTH: 114
<212> TYPE: PRT
<213> ORGANISM: Mus musculus

<400> SEQUENCE: 18

Glu Val Gln Leu Leu Glu Thr Gly Gly Gly Leu Val Gln Pro Gly Gly
1               5                   10                  15

Ser Arg Gly Leu Ser Cys Glu Gly Ser Gly Phe Thr Phe Ser Gly Phe
            20                  25                  30

Trp Met Ser Trp Val Arg Gln Thr Pro Gly Lys Thr Leu Glu Trp Ile
        35                  40                  45

Gly Asp Ile Asn Ser Asp Gly Ser Ser Ile Asn Tyr Ala Pro Ser Ile
    50                  55                  60

Lys Asp Arg Phe Thr Ile Phe Arg Asp Asn Asp Lys Ser Ile Leu Tyr
65                  70                  75                  80

Leu Gln Met Thr Asn Val Arg Ser Glu Asp Thr Gly Thr Tyr Phe Cys
                85                  90                  95

Val Thr Thr Tyr Gly Asp Tyr Trp Gly Gln Gly Thr Thr Leu Thr Val
            100                 105                 110

Ser Ser

<210> SEQ ID NO 19
<211> LENGTH: 107
<212> TYPE: PRT
<213> ORGANISM: Mus musculus

<400> SEQUENCE: 19

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ser His
            20                  25                  30

Val Gly Trp Tyr Gln Gln Lys Ser Gly Gln Ser Pro Lys Ala Leu Ile
        35                  40                  45

Tyr Ser Ala Ser Asn Arg Tyr Ile Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr His Ile Tyr Pro Tyr
                85                  90                  95

Thr Phe Gly Gly Gly Thr Arg Leu Glu Ile Lys
            100                 105

<210> SEQ ID NO 20
<211> LENGTH: 5
<212> TYPE: PRT
<213> ORGANISM: Mus musculus

<400> SEQUENCE: 20

Gly Phe Trp Met Ser
1               5
```

<210> SEQ ID NO 21
<211> LENGTH: 17
<212> TYPE: PRT
<213> ORGANISM: Mus musculus

<400> SEQUENCE: 21

Asp Ile Asn Ser Asp Gly Ser Ser Ile Asn Tyr Ala Pro Ser Ile Lys
1               5                   10                  15

Asp

<210> SEQ ID NO 22
<211> LENGTH: 5
<212> TYPE: PRT
<213> ORGANISM: Mus musculus

<400> SEQUENCE: 22

Thr Tyr Gly Asp Tyr
1               5

<210> SEQ ID NO 23
<211> LENGTH: 11
<212> TYPE: PRT
<213> ORGANISM: Mus musculus

<400> SEQUENCE: 23

Lys Ala Ser Gln Asn Val Gly Ser His Val Gly
1               5                   10

<210> SEQ ID NO 24
<211> LENGTH: 7
<212> TYPE: PRT
<213> ORGANISM: Mus musculus

<400> SEQUENCE: 24

Ser Ala Ser Asn Arg Tyr Ile
1               5

<210> SEQ ID NO 25
<211> LENGTH: 9
<212> TYPE: PRT
<213> ORGANISM: Mus musculus

<400> SEQUENCE: 25

Gln Gln Tyr His Ile Tyr Pro Tyr Thr
1               5

<210> SEQ ID NO 26
<211> LENGTH: 117
<212> TYPE: PRT
<213> ORGANISM: Mus musculus

<400> SEQUENCE: 26

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
                20                  25                  30

Trp Val His Trp Val Lys Gln Arg Pro Gly Gln Gly Leu Glu Trp Ile
            35                  40                  45

Gly Ala Ile Tyr Pro Gly Asn Ile Asp Ala Ser Tyr Asn Gln Lys Phe
        50                  55                  60

Lys Gly Lys Ala Lys Leu Thr Ala Val Thr Ser Thr Ser Thr Ala Tyr

```
                65                  70                  75                  80
Met Glu Leu Ser Ser Leu Thr Asn Glu Asp Ser Ala Val Tyr Tyr Cys
                        85                  90                  95

Ser Tyr Asp Tyr Asp Ala Trp Phe Val Tyr Trp Gly Gln Gly Thr Leu
                100                 105                 110

Val Thr Val Ser Ala
        115

<210> SEQ ID NO 27
<211> LENGTH: 107
<212> TYPE: PRT
<213> ORGANISM: Mus musculus

<400> SEQUENCE: 27

Asp Ile Gln Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Thr Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Phe Thr Pro Arg
                85                  90                  95

Thr Phe Gly Gly Gly Thr Lys Leu Glu Leu Lys
                100                 105

<210> SEQ ID NO 28
<211> LENGTH: 5
<212> TYPE: PRT
<213> ORGANISM: Mus musculus

<400> SEQUENCE: 28

Ser Tyr Trp Val His
1               5

<210> SEQ ID NO 29
<211> LENGTH: 17
<212> TYPE: PRT
<213> ORGANISM: Mus musculus

<400> SEQUENCE: 29

Ala Ile Tyr Pro Gly Asn Ile Asp Ala Ser Tyr Asn Gln Lys Phe Lys
1               5                   10                  15

Gly

<210> SEQ ID NO 30
<211> LENGTH: 8
<212> TYPE: PRT
<213> ORGANISM: Mus musculus

<400> SEQUENCE: 30

Asp Tyr Asp Ala Trp Phe Val Tyr
1               5

<210> SEQ ID NO 31
<211> LENGTH: 11
<212> TYPE: PRT
```

```
<213> ORGANISM: Mus musculus

<400> SEQUENCE: 31

Lys Ala Ser Gln Asp Val Ser Thr Ala Val Ala
1               5                   10

<210> SEQ ID NO 32
<211> LENGTH: 7
<212> TYPE: PRT
<213> ORGANISM: Mus musculus

<400> SEQUENCE: 32

Ser Ala Ser Tyr Arg Tyr Thr
1               5

<210> SEQ ID NO 33
<211> LENGTH: 9
<212> TYPE: PRT
<213> ORGANISM: Mus musculus

<400> SEQUENCE: 33

Gln Gln His Tyr Phe Thr Pro Arg Thr
1               5

<210> SEQ ID NO 34
<211> LENGTH: 106
<212> TYPE: PRT
<213> ORGANISM: Artificial Sequence
<220> FEATURE:
<223> OTHER INFORMATION: V205C cysteine engineered light chain constant
      region (Igkappa)

<400> SEQUENCE: 34

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Cys Thr Lys Ser Phe Asn Arg Gly Glu Cys
            100                 105

<210> SEQ ID NO 35
<211> LENGTH: 330
<212> TYPE: PRT
<213> ORGANISM: Artificial Sequence
<220> FEATURE:
<223> OTHER INFORMATION: A118C cysteine engineered heavy chain constant
      region (IgG1)

<400> SEQUENCE: 35

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
```

```
                35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 36
<211> LENGTH: 330
<212> TYPE: PRT
<213> ORGANISM: Artificial Sequence
<220> FEATURE:
<223> OTHER INFORMATION: S400C cysteine engineered heavy chain constant
      region (IgG1)

<400> SEQUENCE: 36

Ala Ser Thr Lys Gly Pro Ser Val Phe Pro Leu Ala Pro Ser Ser Lys
 1                   5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60
```

```
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Cys Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 580
<212> TYPE: PRT
<213> ORGANISM: Macaca fascicularis

<400> SEQUENCE: 37

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
                20                  25                  30

Ala Thr Cys His Gln Val Arg Ser Phe Phe Gln Arg Leu Gln Pro Gly
            35                  40                  45

Leu Lys Trp Val Pro Glu Thr Pro Val Pro Gly Ser Asp Leu Gln Val
    50                  55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
            100                 105                 110
```

-continued

```
Glu Ala Phe Glu Ile Val Val Arg His Ala Lys Asn Tyr Thr Asn Ala
            115                 120                 125
Met Phe Lys Asn Asn Tyr Pro Ser Leu Thr Pro Gln Ala Phe Glu Phe
        130                 135                 140
Val Gly Glu Phe Phe Thr Asp Val Ser Leu Tyr Ile Leu Gly Ser Asp
145                 150                 155                 160
Ile Asn Val Asp Asp Met Val Asn Glu Leu Phe Asp Ser Leu Phe Pro
                165                 170                 175
Val Ile Tyr Thr Gln Leu Met Asn Pro Gly Leu Pro Asp Ser Ala Leu
            180                 185                 190
Asp Ile Asn Glu Cys Leu Arg Gly Ala Arg Arg Asp Leu Lys Val Phe
        195                 200                 205
Gly Asn Phe Pro Lys Leu Ile Met Thr Gln Val Ser Lys Ser Leu Gln
    210                 215                 220
Val Thr Arg Ile Phe Leu Gln Ala Leu Asn Leu Gly Ile Glu Val Ile
225                 230                 235                 240
Asn Thr Thr Asp His Leu Lys Phe Ser Lys Asp Cys Gly Arg Met Leu
                245                 250                 255
Thr Arg Met Trp Tyr Cys Ser Tyr Cys Gln Gly Leu Met Met Val Lys
            260                 265                 270
Pro Cys Gly Gly Tyr Cys Asn Val Val Met Gln Gly Cys Met Ala Gly
        275                 280                 285
Val Val Glu Ile Asp Lys Tyr Trp Arg Glu Tyr Ile Leu Ser Leu Glu
    290                 295                 300
Glu Leu Val Asn Gly Met Tyr Arg Ile Tyr Asp Met Glu Asn Val Leu
305                 310                 315                 320
Leu Gly Leu Phe Ser Thr Ile His Asp Ser Ile Gln Tyr Val Gln Lys
                325                 330                 335
Asn Ala Gly Lys Leu Thr Thr Thr Ile Gly Lys Leu Cys Ala His Ser
            340                 345                 350
Gln Gln Arg Gln Tyr Arg Ser Ala Tyr Tyr Pro Glu Asp Leu Phe Ile
        355                 360                 365
Asp Lys Lys Val Leu Lys Val Ala His Val Glu His Glu Glu Thr Leu
    370                 375                 380
Ser Ser Arg Arg Arg Glu Leu Ile Gln Lys Leu Lys Ser Phe Ile Ser
385                 390                 395                 400
Phe Tyr Ser Ala Leu Pro Gly Tyr Ile Cys Ser His Ser Pro Val Ala
                405                 410                 415
Glu Asn Asp Thr Leu Cys Trp Asn Gly Gln Glu Leu Val Glu Arg Tyr
            420                 425                 430
Ser Gln Lys Ala Ala Arg Asn Gly Met Lys Asn Gln Phe Asn Leu His
        435                 440                 445
Glu Leu Lys Met Lys Gly Pro Glu Pro Val Val Ser Gln Ile Ile Asp
    450                 455                 460
Lys Leu Lys His Ile Asn Gln Leu Leu Arg Thr Met Ser Val Pro Lys
465                 470                 475                 480
Gly Arg Val Leu Asp Lys Asn Leu Asp Glu Glu Gly Phe Glu Ser Gly
                485                 490                 495
Asp Cys Gly Asp Asp Glu Asp Glu Cys Ile Gly Gly Ser Gly Asp Gly
            500                 505                 510
Met Met Lys Val Lys Asn Gln Leu Arg Phe Leu Ala Glu Leu Ala Tyr
        515                 520                 525
```

```
Asp Leu Asp Val Asp Val Pro Gly Asn Asn Gln Gln Ala Thr Pro
    530             535                 540

Lys Asp Asn Glu Ile Ser Thr Phe His Asn Leu Gly Asn Val His Ser
545                 550                 555                 560

Pro Leu Lys Leu Leu Thr Ser Met Ala Ile Ser Val Val Cys Phe Phe
                565                 570                 575

Phe Leu Val His
            580

<210> SEQ ID NO 38
<211> LENGTH: 580
<212> TYPE: PRT
<213> ORGANISM: Macaca mulatta

<400> SEQUENCE: 38

Met Ala Gly Thr Val Arg Thr Ala Cys Leu Val Val Ala Met Leu Leu
1               5                   10                  15

Ser Leu Asp Phe Pro Gly Gln Ala Gln Pro Pro Pro Pro Pro Pro Asp
                20                  25                  30

Ala Thr Cys His Gln Val Arg Ser Phe Phe Gln Arg Leu Gln Pro Gly
                35                  40                  45

Leu Lys Trp Val Pro Glu Thr Pro Val Pro Gly Ser Asp Leu Gln Val
50              55                  60

Cys Leu Pro Lys Gly Pro Thr Cys Cys Ser Arg Lys Met Glu Glu Lys
65                  70                  75                  80

Tyr Gln Leu Thr Ala Arg Leu Asn Met Glu Gln Leu Leu Gln Ser Ala
                85                  90                  95

Ser Met Glu Leu Lys Phe Leu Ile Ile Gln Asn Ala Ala Val Phe Gln
                100                 105                 110

Glu Ala Phe Glu Ile Val Val Arg His Ala Lys Asn Tyr Thr Asn Ala
                115                 120                 125

Met Phe Lys Asn Asn Tyr Pro Ser Leu Thr Pro Gln Ala Phe Glu Phe
            130                 135                 140

Val Gly Glu Phe Phe Thr Asp Val Ser Leu Tyr Ile Leu Gly Ser Asp
145                 150                 155                 160

Ile Asn Val Asp Asp Met Val Asn Glu Leu Phe Asp Ser Leu Phe Pro
                165                 170                 175

Val Ile Tyr Thr Gln Leu Met Asn Pro Gly Leu Pro Asp Ser Ala Leu
                180                 185                 190

Asp Ile Asn Glu Cys Leu Arg Gly Ala Arg Arg Asp Leu Lys Val Phe
            195                 200                 205

Gly Asn Phe Pro Lys Leu Ile Met Thr Gln Val Ser Lys Ser Leu Gln
210                 215                 220

Val Thr Arg Ile Phe Leu Gln Ala Leu Asn Leu Gly Ile Glu Val Ile
225                 230                 235                 240

Asn Thr Thr Asp His Leu Lys Phe Ser Lys Asp Cys Gly Arg Met Leu
                245                 250                 255

Thr Arg Met Trp Tyr Cys Ser Tyr Cys Gln Gly Leu Met Met Val Lys
            260                 265                 270

Pro Cys Gly Gly Tyr Cys Asn Val Val Met Gln Gly Cys Met Ala Gly
            275                 280                 285

Val Val Glu Ile Asp Lys Tyr Trp Arg Glu Tyr Ile Leu Ser Leu Glu
        290                 295                 300

Glu Leu Val Asn Gly Met Tyr Arg Ile Tyr Asp Met Glu Asn Val Leu
305                 310                 315                 320
```

-continued

Leu Gly Leu Phe Ser Thr Ile His Asp Ser Ile Gln Tyr Val Gln Lys
                325                 330                 335
Asn Ala Gly Lys Leu Thr Thr Thr Ile Gly Lys Leu Cys Ala His Ser
            340                 345                 350
Gln Gln Arg Gln Tyr Arg Ser Ala Tyr Tyr Pro Glu Asp Leu Phe Ile
        355                 360                 365
Asp Lys Lys Val Leu Lys Val Ala His Val Glu His Glu Glu Thr Leu
    370                 375                 380
Ser Ser Arg Arg Arg Glu Leu Ile Gln Lys Leu Lys Ser Phe Ile Ser
385                 390                 395                 400
Phe Tyr Ser Ala Leu Pro Gly Tyr Ile Cys Ser His Ser Pro Val Ala
                405                 410                 415
Glu Asn Asp Thr Leu Cys Trp Asn Gly Gln Glu Leu Val Glu Arg Tyr
            420                 425                 430
Ser Gln Lys Ala Ala Arg Asn Gly Met Lys Asn Gln Phe Asn Leu His
        435                 440                 445
Glu Leu Lys Met Lys Gly Pro Glu Pro Val Val Ser Gln Ile Ile Asp
    450                 455                 460
Lys Leu Lys His Ile Asn Gln Leu Leu Arg Thr Met Ser Val Pro Lys
465                 470                 475                 480
Gly Arg Val Leu Asp Lys Asn Leu Asp Glu Glu Gly Phe Glu Ser Gly
                485                 490                 495
Asp Cys Gly Asp Asp Glu Asp Glu Cys Ile Gly Gly Ser Gly Asp Gly
            500                 505                 510
Met Met Lys Val Lys Asn Gln Leu Arg Phe Leu Ala Glu Leu Ala Tyr
        515                 520                 525
Asp Leu Asp Val Asp Asp Val Pro Gly Asn Asn Gln Gln Ala Thr Pro
    530                 535                 540
Lys Asp Asn Glu Ile Ser Thr Phe His Asn Leu Gly Asn Val His Ser
545                 550                 555                 560
Pro Leu Lys Leu Leu Thr Ser Met Ala Ile Ser Val Val Cys Phe Phe
                565                 570                 575
Phe Leu Val His
            580

<210> SEQ ID NO 39
<211> LENGTH: 579
<212> TYPE: PRT
<213> ORGANISM: Mus musculus

<400> SEQUENCE: 39

Met Ala Gly Thr Val Arg Thr Ala Cys Leu Leu Val Ala Met Leu Leu
1               5                   10                  15
Gly Leu Gly Cys Leu Gly Gln Ala Gln Pro Pro Pro Pro Asp Ala
            20                  25                  30
Thr Cys His Gln Val Arg Ser Phe Phe Gln Arg Leu Gln Pro Gly Leu
        35                  40                  45
Lys Trp Val Pro Glu Thr Pro Val Pro Gly Ser Asp Leu Gln Val Cys
    50                  55                  60
Leu Pro Lys Gly Pro Thr Cys Cys Ser Arg Lys Met Glu Glu Lys Tyr
65                  70                  75                  80
Gln Leu Thr Ala Arg Leu Asn Met Glu Gln Leu Leu Gln Ser Ala Ser
                85                  90                  95
Met Glu Leu Lys Phe Leu Ile Ile Gln Asn Ala Ala Val Phe Gln Glu

```
            100                 105                 110
Ala Phe Glu Ile Val Val Arg His Ala Lys Asn Tyr Thr Asn Ala Met
            115                 120                 125
Phe Lys Asn Asn Tyr Pro Ser Leu Thr Pro Gln Ala Phe Glu Phe Val
            130                 135                 140
Gly Glu Phe Phe Thr Asp Val Ser Leu Tyr Ile Leu Gly Ser Asp Ile
145                 150                 155                 160
Asn Val Asp Asp Met Val Asn Glu Leu Phe Asp Ser Leu Phe Pro Val
                    165                 170                 175
Ile Tyr Thr Gln Met Met Asn Pro Gly Leu Pro Glu Ser Val Leu Asp
                    180                 185                 190
Ile Asn Glu Cys Leu Arg Gly Ala Arg Arg Asp Leu Lys Val Phe Gly
                    195                 200                 205
Ser Phe Pro Lys Leu Ile Met Thr Gln Val Ser Lys Ser Leu Gln Val
            210                 215                 220
Thr Arg Ile Phe Leu Gln Ala Leu Asn Leu Gly Ile Glu Val Ile Asn
225                 230                 235                 240
Thr Thr Asp His Leu Lys Phe Ser Lys Asp Cys Gly Arg Met Leu Thr
                    245                 250                 255
Arg Met Trp Tyr Cys Ser Tyr Cys Gln Gly Leu Met Met Val Lys Pro
            260                 265                 270
Cys Gly Gly Tyr Cys Asn Val Val Met Gln Gly Cys Met Ala Gly Val
            275                 280                 285
Val Glu Ile Asp Lys Tyr Trp Arg Glu Tyr Ile Leu Ser Leu Glu Glu
            290                 295                 300
Leu Val Asn Gly Met Tyr Arg Ile Tyr Asp Met Glu Asn Val Leu Leu
305                 310                 315                 320
Gly Leu Phe Ser Thr Ile His Asp Ser Ile Gln Tyr Val Gln Lys Asn
                    325                 330                 335
Gly Gly Lys Leu Thr Thr Thr Ile Gly Lys Leu Cys Ala His Ser Gln
                    340                 345                 350
Gln Arg Gln Tyr Arg Ser Ala Tyr Tyr Pro Glu Asp Leu Phe Ile Asp
                    355                 360                 365
Lys Lys Ile Leu Lys Val Ala His Val Glu His Glu Glu Thr Leu Ser
            370                 375                 380
Ser Arg Arg Arg Glu Leu Ile Gln Lys Leu Lys Ser Phe Ile Asn Phe
385                 390                 395                 400
Tyr Ser Ala Leu Pro Gly Tyr Ile Cys Ser His Ser Pro Val Ala Glu
                    405                 410                 415
Asn Asp Thr Leu Cys Trp Asn Gly Gln Glu Leu Val Glu Arg Tyr Ser
                    420                 425                 430
Gln Lys Ala Ala Arg Asn Gly Met Lys Asn Gln Phe Asn Leu His Glu
            435                 440                 445
Leu Lys Met Lys Gly Pro Glu Pro Val Val Ser Gln Ile Ile Asp Lys
            450                 455                 460
Leu Lys His Ile Asn Gln Leu Leu Arg Thr Met Ser Val Pro Lys Gly
465                 470                 475                 480
Lys Val Leu Asp Lys Ser Leu Asp Glu Glu Gly Leu Glu Ser Gly Asp
                    485                 490                 495
Cys Gly Asp Asp Glu Asp Glu Cys Ile Gly Ser Ser Gly Asp Gly Met
                    500                 505                 510
Val Lys Val Lys Asn Gln Leu Arg Phe Leu Ala Glu Leu Ala Tyr Asp
            515                 520                 525
```

```
Leu Asp Val Asp Asp Ala Pro Gly Asn Lys Gln His Gly Asn Gln Lys
            530                 535                 540

Asp Asn Glu Ile Thr Thr Ser His Ser Val Gly Asn Met Pro Ser Pro
545                 550                 555                 560

Leu Lys Ile Leu Ile Ser Val Ala Ile Tyr Val Ala Cys Phe Phe Phe
            565                 570                 575

Leu Val His

<210> SEQ ID NO 40
<211> LENGTH: 579
<212> TYPE: PRT
<213> ORGANISM: Rattus rattus

<400> SEQUENCE: 40

Met Ala Gly Thr Val Arg Thr Ala Cys Leu Leu Val Ala Met Leu Leu
1               5                   10                  15

Gly Leu Gly Cys Leu Gly Gln Ala Gln Pro Pro Pro Pro Asp Ala
            20                  25                  30

Thr Cys His Gln Val Arg Ser Phe Phe Gln Arg Leu Gln Pro Gly Leu
            35                  40                  45

Lys Trp Val Pro Glu Thr Pro Val Pro Gly Ser Asp Leu Gln Val Cys
        50                  55                  60

Leu Pro Lys Gly Pro Thr Cys Cys Ser Arg Lys Met Glu Glu Lys Tyr
65                  70                  75                  80

Gln Leu Thr Ala Arg Leu Asn Met Glu Gln Leu Leu Gln Ser Ala Ser
                85                  90                  95

Met Glu Leu Lys Phe Leu Ile Ile Gln Asn Ala Ala Val Phe Gln Glu
            100                 105                 110

Ala Phe Glu Ile Val Val Arg His Ala Lys Asn Tyr Thr Asn Ala Met
            115                 120                 125

Phe Lys Asn Asn Tyr Pro Ser Leu Thr Pro Gln Ala Phe Glu Phe Val
        130                 135                 140

Gly Glu Phe Phe Thr Asp Val Ser Leu Tyr Ile Leu Gly Ser Asp Ile
145                 150                 155                 160

Asn Val Asp Asp Met Val Asn Glu Leu Phe Asp Ser Leu Phe Pro Val
            165                 170                 175

Ile Tyr Thr Gln Met Met Asn Pro Gly Leu Pro Glu Ser Val Leu Asp
            180                 185                 190

Ile Asn Glu Cys Leu Arg Gly Ala Arg Arg Asp Leu Lys Val Phe Gly
        195                 200                 205

Ser Phe Pro Lys Leu Ile Met Thr Gln Val Ser Lys Ser Leu Gln Val
210                 215                 220

Thr Arg Ile Phe Leu Gln Ala Leu Asn Leu Gly Ile Glu Val Ile Asn
225                 230                 235                 240

Thr Thr Asp His Leu Lys Phe Ser Lys Asp Cys Gly Arg Met Leu Thr
            245                 250                 255

Arg Met Trp Tyr Cys Ser Tyr Cys Gln Gly Leu Met Met Val Lys Pro
            260                 265                 270

Cys Gly Gly Tyr Cys Asn Val Val Met Gln Gly Cys Met Ala Gly Val
        275                 280                 285

Val Glu Ile Asp Lys Tyr Trp Arg Glu Tyr Ile Leu Ser Leu Glu Glu
        290                 295                 300

Leu Val Asn Gly Met Tyr Arg Ile Tyr Asp Met Glu Asn Val Leu Leu
305                 310                 315                 320
```

-continued

```
Gly Leu Phe Ser Thr Ile His Asp Ser Ile Gln Tyr Val Gln Lys Asn
                325                 330                 335
Gly Gly Lys Leu Thr Thr Thr Ile Gly Lys Leu Cys Ala His Ser Gln
            340                 345                 350
Gln Arg Gln Tyr Arg Ser Ala Tyr Tyr Pro Glu Asp Leu Phe Ile Asp
        355                 360                 365
Lys Lys Val Leu Lys Val Ala Arg Val Glu His Glu Thr Leu Ser
    370                 375                 380
Ser Arg Arg Arg Glu Leu Ile Gln Lys Leu Lys Ser Phe Ile Ser Phe
385                 390                 395                 400
Tyr Ser Ala Leu Pro Gly Tyr Ile Cys Ser His Ser Pro Val Ala Glu
                405                 410                 415
Asn Asp Thr Leu Cys Trp Asn Gly Gln Glu Leu Val Glu Arg Tyr Ser
            420                 425                 430
Gln Lys Ala Ala Arg Asn Gly Met Lys Asn Gln Phe Asn Leu His Glu
        435                 440                 445
Leu Lys Met Lys Gly Pro Glu Pro Val Val Ser Gln Ile Ile Asp Lys
    450                 455                 460
Leu Lys His Ile Asn Gln Leu Leu Arg Thr Met Ser Val Pro Lys Gly
465                 470                 475                 480
Lys Val Val Asp Lys Ser Leu Asp Glu Glu Gly Leu Glu Ser Gly Asp
                485                 490                 495
Cys Gly Asp Asp Glu Asp Glu Cys Ile Gly Ser Ser Gly Asp Gly Met
            500                 505                 510
Met Lys Val Lys Asn Gln Leu Arg Phe Leu Ala Glu Leu Ala Tyr Asp
        515                 520                 525
Leu Asp Val Asp Asp Ala Pro Gly Asn Lys Gln His Gly Asn Gln Lys
    530                 535                 540
Asp Asn Glu Ile Thr Thr Ser His Ser Val Gly Asn Met Pro Ser Pro
545                 550                 555                 560
Leu Lys Ile Leu Ile Ser Val Ala Ile Tyr Val Ala Cys Phe Phe Phe
                565                 570                 575
Leu Val His

<210> SEQ ID NO 41
<211> LENGTH: 50
<212> TYPE: PRT
<213> ORGANISM: Artificial Sequence
<220> FEATURE:
<223> OTHER INFORMATION: HSV signal sequence gD (HSV ss gD)

<400> SEQUENCE: 41

Met Gly Gly Thr Ala Ala Arg Leu Gly Ala Val Ile Leu Phe Val Val
1               5                   10                  15
Ile Val Gly Leu His Gly Val Arg Gly Lys Tyr Ala Leu Ala Asp Ala
            20                  25                  30
Ser Leu Lys Met Ala Asp Pro Asn Arg Phe Arg Gly Lys Asp Leu Pro
        35                  40                  45
Val Leu
    50

<210> SEQ ID NO 42
<211> LENGTH: 450
<212> TYPE: PRT
<213> ORGANISM: Artificial Sequence
<220> FEATURE:
```

<223> OTHER INFORMATION: 7H1 IgG1 heavy chain

<400> SEQUENCE: 42

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Lys Gln Lys Pro Gly Gln Gly Leu Glu Trp Ile
        35                  40                  45

Gly Trp Ile Tyr Pro Gly Ser Gly His Thr Glu Cys Asn Glu Thr Phe
    50                  55                  60

Lys Gly Lys Ala Thr Leu Thr Val Asp Thr Ser Ser Thr Ala Tyr
65                  70                  75                  80

Met Gln Leu Ser Ser Leu Thr Ser Glu Asp Thr Ala Val Tyr Phe Cys
                85                  90                  95

Thr Arg Gly Tyr Tyr Ala Pro Met Gly Tyr Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
        420                 425                 430
Glu Ala Leu His Asn His Tyr Thr Gln Lys Ser Leu Ser Leu Ser Pro
            435                 440                 445
Gly Lys
    450

<210> SEQ ID NO 43
<211> LENGTH: 450
<212> TYPE: PRT
<213> ORGANISM: Artificial Sequence
<220> FEATURE:
<223> OTHER INFORMATION: 7H1 A118C IgG1 heavy chain

<400> SEQUENCE: 43

Gln Val Gln Leu Gln Gln Ser Gly Pro Glu Leu Val Lys Pro Gly Ala
1               5                   10                  15
Ser Val Lys Ile Ser Cys Lys Ala Ser Gly Tyr Thr Phe Thr Asp Tyr
            20                  25                  30
Tyr Ile Asn Trp Val Lys Gln Lys Pro Gly Gln Gly Leu Glu Trp Ile
        35                  40                  45
Gly Trp Ile Tyr Pro Gly Ser Gly His Thr Glu Cys Asn Glu Thr Phe
    50                  55                  60
Lys Gly Lys Ala Thr Leu Thr Val Asp Thr Ser Ser Ser Thr Ala Tyr
65                  70                  75                  80
Met Gln Leu Ser Ser Leu Thr Ser Glu Asp Thr Ala Val Tyr Phe Cys
                85                  90                  95
Thr Arg Gly Tyr Tyr Ala Pro Met Gly Tyr Phe Asp Tyr Trp Gly Gln
            100                 105                 110
Gly Thr Thr Leu Thr Val Ser Ser Cys Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 44
<211> LENGTH: 214
<212> TYPE: PRT
<213> ORGANISM: Artificial Sequence
<220> FEATURE:
<223> OTHER INFORMATION: 7H1 kappa light chain

<400> SEQUENCE: 44

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Gly Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

-continued

```
Phe Asn Arg Gly Glu Cys
    210

<210> SEQ ID NO 45
<211> LENGTH: 443
<212> TYPE: PRT
<213> ORGANISM: Artificial Sequence
<220> FEATURE:
<223> OTHER INFORMATION: 4A11 A118C IgG1 heavy chain

<400> SEQUENCE: 45

Glu Val Gln Leu Gln Gln Ser Ala Ala Glu Leu Ala Arg Pro Gly Ala
1               5                   10                  15

Ser Val Arg Met Ser Cys Arg Thr Ser Gly Tyr Thr Phe Thr Thr Tyr
            20                  25                  30

Thr Ile His Trp Met Lys Gln Arg Pro Gly Gln Gly Leu Glu Trp Ile
        35                  40                  45

Gly Tyr Ile Asn Pro Asn Gly Gly Tyr Thr Glu Tyr Asn Gln Lys Phe
    50                  55                  60

Arg Asp Arg Thr Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Asn Phe Asp Tyr Trp Gly Gln Gly Thr Thr Leu Thr Val Ser
            100                 105                 110

Ser Cys Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350
```

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 46
<211> LENGTH: 214
<212> TYPE: PRT
<213> ORGANISM: Artificial Sequence
<220> FEATURE:
<223> OTHER INFORMATION: 4A11 kappa light chain

<400> SEQUENCE: 46

Asp Ile Val Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Val Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Val Gly Ile Tyr Tyr Cys Leu Gln Tyr Asp Glu Phe Pro Leu
                85                  90                  95

Thr Leu Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 47
<211> LENGTH: 444
<212> TYPE: PRT
<213> ORGANISM: Artificial Sequence
<220> FEATURE:
<223> OTHER INFORMATION: 15G1 A118C IgG1 heavy chain

<400> SEQUENCE: 47

-continued

```
Glu Val Gln Leu Leu Glu Thr Gly Gly Gly Leu Val Gln Pro Gly Gly
1               5                   10                  15

Ser Arg Gly Leu Ser Cys Glu Gly Ser Gly Phe Thr Phe Ser Gly Phe
            20                  25                  30

Trp Met Ser Trp Val Arg Gln Thr Pro Gly Lys Thr Leu Glu Trp Ile
        35                  40                  45

Gly Asp Ile Asn Ser Asp Gly Ser Ser Ile Asn Tyr Ala Pro Ser Ile
    50                  55                  60

Lys Asp Arg Phe Thr Ile Phe Arg Asp Asn Asp Lys Ser Ile Leu Tyr
65                  70                  75                  80

Leu Gln Met Thr Asn Val Arg Ser Glu Asp Thr Gly Tyr Tyr Phe Cys
                85                  90                  95

Val Thr Thr Tyr Gly Asp Tyr Trp Gly Gln Gly Thr Thr Leu Thr Val
            100                 105                 110

Ser Ser Cys Ser Thr Lys Gly Pro Ser Val Phe Pro Leu Ala Pro Ser
        115                 120                 125

Ser Lys Ser Thr Ser Gly Gly Thr Ala Ala Leu Gly Cys Leu Val Lys
    130                 135                 140

Asp Tyr Phe Pro Glu Pro Val Thr Val Ser Trp Asn Ser Gly Ala Leu
145                 150                 155                 160

Thr Ser Gly Val His Thr Phe Pro Ala Val Leu Gln Ser Ser Gly Leu
                165                 170                 175

Tyr Ser Leu Ser Ser Val Val Thr Val Pro Ser Ser Ser Leu Gly Thr
            180                 185                 190

Gln Thr Tyr Ile Cys Asn Val Asn His Lys Pro Ser Asn Thr Lys Val
        195                 200                 205

Asp Lys Lys Val Glu Pro Lys Ser Cys Asp Lys Thr His Thr Cys Pro
210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285

Arg Glu Glu Gln Tyr Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Lys Leu Thr Val Asp Lys Ser Arg Trp Gln Gln
                405                 410                 415
```

```
Gly Asn Val Phe Ser Cys Ser Val Met His Glu Ala Leu His Asn His
                420                 425                 430

Tyr Thr Gln Lys Ser Leu Ser Leu Ser Pro Gly Lys
        435                 440

<210> SEQ ID NO 48
<211> LENGTH: 214
<212> TYPE: PRT
<213> ORGANISM: Artificial Sequence
<220> FEATURE:
<223> OTHER INFORMATION: 15G1 kappa light chain

<400> SEQUENCE: 48

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Ser His
                20                  25                  30

Val Gly Trp Tyr Gln Gln Lys Ser Gly Gln Ser Pro Lys Ala Leu Ile
            35                  40                  45

Tyr Ser Ala Ser Asn Arg Tyr Ile Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr His Ile Tyr Pro Tyr
                85                  90                  95

Thr Phe Gly Gly Gly Thr Arg Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

US 9,926,377 B2

ANTI-GPC3 ANTIBODIES AND IMMUNOCONJUGATES

CROSS-REFERENCE TO RELATED APPLICATIONS

The present application claims the benefit of priority of U.S. Provisional Application No. 60/001,868, filed May 22, 2014.

FIELD OF THE INVENTION

The present invention relates to anti-GPC3 antibodies and immunoconjugates and methods of using the same.

BACKGROUND

Glypican-3 (GPC3) is a member of the glypican family, which are heparin sulfate proteoglycans linked to the cell surface through a glycosyl-phosphatidylinositol anchor. GPC3 has been shown to be highly expressed in over 70% of hepatocellular carcinoma biopsies, but not in adjacent nontumor tissue. Patients with GPC3-positive HCC have a significantly lower disease-free survival rate than patients with GPC3-negative HCC.

There is a need in the art for safe and effective agents that target GPC3 for the diagnosis and treatment of GPC3-associated conditions, such as cancer. The invention fulfills that need and provides other benefits.

SUMMARY

The invention provides anti-GPC3 antibodies and immunoconjugates and methods of using the same.

In some embodiments, an isolated antibody that binds to GPC3 is provided. In some embodiments, the antibody binds to GPC3 and has one or more of the following characteristics:
  a) binds to recombinant human GPC3;
  b) binds to recombinant cynomolgus monkey GPC3;
  c) binds to endogenous GPC3 on the surface of HepG2 cells;
  d) binds to cynomolgus monkey GPC3 expressed on the surface of 293 cells;
  e) binds to endogenous GPC3 on the surface of a cancer cell;
  f) binds to endogenous GPC3 on the surface of hepatocellular carcinoma cell;
  g) binds to endogenous GPC3 on the surface of cells of a cell line selected from HepG2, Hep3B, Huh7, and JHH-7;
  h) binds to an epitope within amino acids 25 to 137 of human GPC3;
  i) binds to an epitope spanning the furin cleavage site at amino acids R358/S359 of human GPC3;
  j) binds to full-length mature human GPC3 (e.g., amino acids 25 to 560 or amino acids 25 to 580 of SEQ ID NO: 1), but does not bind to an N-terminal fragment of human GPC3 (amino acids 25 to 358 of SEQ ID NO: 1) or to a C-terminal fragment of human GPC3 (amino acids 359 to 560 or amino acids 359 to 580 of SEQ ID NO: 1);
  k) binds to an epitope within amino acids 420 to 470 of human GPC3;
  l) binds to an epitope within amino acids 470 to 509 of human GPC3;
  m) competes for binding to human GPC3 with antibody 7H1;
  n) competes for binding to human GPC3 with antibody 4G7;
  o) competes for binding to human GPC3 with antibody 15G1; and/or
  p) competes for binding to human GPC3 with antibody 4A11.

In some embodiments, human GPC3 comprises the sequence of SEQ ID NO: 1 (full-length GPC3 precursor) or comprises amino acids 25 to 580 of SEQ ID NOP: 1 (full-length mature GPC3).

In some embodiments, an isolated antibody that binds human GPC3 is provided, wherein the antibody binds to an epitope selected from:
  q) an epitope within amino acids 25 to 137 of human GPC3;
  r) an epitope spanning the furin cleavage site at amino acids R358/S359 of human GPC3;
  s) an epitope within amino acids 420 to 470 of human GPC3; and
  t) an epitope within amino acids 470 to 509 of human GPC3.

In some embodiments, an isolated antibody that binds human GPC3 is provided, wherein the antibody binds to an epitope within amino acids 25 to 137 of human GPC3. In some embodiments, the antibody binds to GPC3 from at least one species selected from cynomolgus monkey, mouse, and rat. In some embodiments, the antibody binds to GPC3 from cynomolgus monkey, mouse, and rat. In some embodiments, the antibody comprises HVR-H3 comprising the amino acid sequence of SEQ ID NO: 6, HVR-L3 comprising the amino acid sequence of SEQ ID NO: 9, and HVR-H2 comprising the amino acid sequence of SEQ ID NO: 5. In some embodiments, the antibody comprises HVR-H1 comprising the amino acid sequence of SEQ ID NO: 4, HVR-H2 comprising the amino acid sequence of SEQ ID NO: 5, and HVR-H3 comprising the amino acid sequence of SEQ ID NO: 6. In some embodiments, the antibody comprises HVR-L1 comprising the amino acid sequence of SEQ ID NO: 7, HVR-L2 comprising the amino acid sequence of SEQ ID NO: 8, and HVR-L3 comprising the amino acid sequence of SEQ ID NO: 9. In some embodiments, the antibody comprises (a) a VH sequence having at least 95% sequence identity to the amino acid sequence of SEQ ID NO: 2; (b) a VL sequence having at least 95% sequence identity to the amino acid sequence of SEQ ID NO: 3; or (c) a VH as in (a) and a VL as in (b). In some embodiments, the antibody comprises (a) a VH sequence having the amino acid sequence of SEQ ID NO: 2; (b) a VL sequence having the amino acid sequence of SEQ ID NO: 3; (c) a humanized VH based on the amino acid sequence of SEQ ID NO: 2; (d) a humanized VL sequence based on the amino acid sequence of SEQ ID NO: 3; or (e) a VH as in (a) or (c) and a VL as in (b) or (d).

In some embodiments, an isolated antibody that binds human GPC3 is provided, wherein the antibody binds to an epitope spanning the furin cleavage site at amino acids R358/S359 of human GPC3. In some embodiments, an isolated antibody that binds human GPC3 is provided, wherein the antibody binds to full-length mature human GPC3 but does not bind to an N-terminal fragment of human GPC3 consisting of amino acids 25 to 358 of SEQ ID NO: 1, and does not bind to a C-terminal fragment of human GPC3 consisting of amino acids 359 to 560 or amino acids 359 to 580 of SEQ ID NO: 1. In some embodiments, the antibody comprises HVR-H3 comprising the amino acid sequence of SEQ ID NO: 30, HVR-L3 comprising the amino acid sequence of SEQ ID NO: 33, and HVR-H2 comprising the amino acid sequence of SEQ ID NO: 29. In some embodiments, the antibody comprises HVR-H1 comprising the amino acid sequence of SEQ ID NO: 28, HVR-H2 comprising the amino acid sequence of SEQ ID NO: 29, and HVR-H3 comprising the amino acid sequence of SEQ ID NO: 30. In some embodiments, the antibody comprises HVR-L1 comprising the amino acid sequence of SEQ ID NO: 31, HVR-L2 comprising the amino acid sequence of SEQ ID NO: 32, and HVR-L3 comprising the amino acid sequence of SEQ ID NO: 33. In some embodiments, the antibody comprises: (a) a VH sequence having at least 95% sequence identity to the amino acid sequence of SEQ ID NO: 26; (b) a VL sequence having at least 95% sequence identity to the amino acid sequence of SEQ ID NO: 27; or (c) a VH as in (a) and a VL as in (b). In some embodiments, the antibody comprises: (a) a VH sequence having the amino acid sequence of SEQ ID NO: 26; (b) a VL sequence having the amino acid sequence of SEQ ID NO: 27; (c) a humanized VH based on the amino acid sequence of SEQ ID NO: 26; (d) a humanized VL sequence based on the amino acid sequence of SEQ ID NO: 27; or (e) a VH as in (a) or (c) and a VL as in (b) or (d).

In some embodiments, an isolated antibody that binds human GPC3 is provided, wherein the antibody binds to an epitope within amino acids 420 to 470 of human GPC3. In some embodiments, the antibody binds to GPC3 from at least one species selected from cynomolgus monkey, rhesus macaque, mouse, and rat. In some embodiments, the antibody binds to GPC3 from cynomolgus monkey, rhesus macaque, mouse, and rat. In some embodiments, the antibody comprises HVR-H3 comprising the amino acid sequence of SEQ ID NO: 22, HVR-L3 comprising the amino acid sequence of SEQ ID NO: 25, and HVR-H2 comprising the amino acid sequence of SEQ ID NO: 21. In some embodiments, the antibody comprises HVR-H1 comprising the amino acid sequence of SEQ ID NO: 20, HVR-H2 comprising the amino acid sequence of SEQ ID NO: 21, and HVR-H3 comprising the amino acid sequence of SEQ ID NO: 22. In some embodiments, the antibody comprises HVR-L1 comprising the amino acid sequence of SEQ ID NO: 23, HVR-L2 comprising the amino acid sequence of SEQ ID NO: 24, and HVR-L3 comprising the amino acid sequence of SEQ ID NO: 25. In some embodiments, the antibody comprises: (a) a VH sequence having at least 95% sequence identity to the amino acid sequence of SEQ ID NO: 18; (b) a VL sequence having at least 95% sequence identity to the amino acid sequence of SEQ ID NO: 19; or (c) a VH as in (a) and a VL as in (b). In some embodiments, the antibody comprises: (a) a VH sequence having the amino acid sequence of SEQ ID NO: 18; (b) a VL sequence having the amino acid sequence of SEQ ID NO: 19; (c) a humanized VH based on the amino acid sequence of SEQ ID NO: 18; (d) a humanized VL sequence based on the amino acid sequence of SEQ ID NO: 19; or (e) a VH as in (a) or (c) and a VL as in (b) or (d).

In some embodiments, an isolated antibody that binds human GPC3 is provided, wherein the antibody binds to an epitope within amino acids 470 to 509 of human GPC3. In some embodiments, the antibody binds to cynomolgus monkey GPC3. In some embodiments, the antibody does not bind to rat GPC3. In some embodiments, the antibody comprises HVR-H3 comprising the amino acid sequence of SEQ ID NO: 14, HVR-L3 comprising the amino acid sequence of SEQ ID NO: 17, and HVR-H2 comprising the amino acid sequence of SEQ ID NO: 13. In some embodiments, the antibody comprises HVR-H1 comprising the amino acid sequence of SEQ ID NO: 12, HVR-H2 comprising the amino acid sequence of SEQ ID NO: 13, and HVR-H3 comprising the amino acid sequence of SEQ ID NO: 14. In some embodiments, the antibody comprises HVR-L1 comprising the amino acid sequence of SEQ ID NO: 15, HVR-L2 comprising the amino acid sequence of SEQ ID NO: 16, and HVR-L3 comprising the amino acid sequence of SEQ ID NO: 17. In some embodiments, the antibody comprises: (a) a VH sequence having at least 95% sequence identity to the amino acid sequence of SEQ ID NO: 10; (b) a VL sequence having at least 95% sequence identity to the amino acid sequence of SEQ ID NO: 11; or (c) a VH as in (a) and a VL as in (b). In some embodiments, the antibody comprises: (a) a VH sequence having the amino acid sequence of SEQ ID NO: 10; (b) a VL sequence having the amino acid sequence of SEQ ID NO: 11; (c) a humanized VH based on the amino acid sequence of SEQ ID NO: 10; (d) a humanized VL sequence based on the amino acid sequence of SEQ ID NO: 11; or (e) a VH as in (a) or (c) and a VL as in (b) or (d).

In some embodiments, an isolated antibody that binds to GPC3 is provided, wherein the antibody comprises (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9.

In some embodiments, an isolated antibody that binds to GPC3 is provided, wherein the antibody comprises (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17.

In some embodiments, an isolated antibody that binds to GPC3 is provided, wherein the antibody comprises (a) HVR-H1 comprising the amino acid sequence of SEQ ID NO: 20; (b) HVR-H2 comprising the amino acid sequence of SEQ ID NO: 21; (c) HVR-H3 comprising the amino acid sequence of SEQ ID NO: 22; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25.

In some embodiments, an isolated antibody that binds to GPC3 is provided, wherein the antibody comprises (a) HVR-H1 comprising the amino acid sequence of SEQ ID NO: 28; (b) HVR-H2 comprising the amino acid sequence of SEQ ID NO: 29; (c) HVR-H3 comprising the amino acid sequence of SEQ ID NO: 30; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33.

In any of the embodiments described herein, the antibody may be a monoclonal antibody. In any of the embodiments described herein, the antibody may be a human, humanized, or chimeric antibody. In any of the embodiments described herein, the antibody may be an antibody fragment that binds GPC3. In any of the embodiments described herein, the antibody may be an IgG1, IgG2a or IgG2b antibody.

In any of the embodiments described herein, GPC3 may be human GPC3 comprising amino acids 25 to 580 of SEQ ID NO: 1.

In some embodiments, an isolated nucleic acid encoding an antibody described herein is provided. In some embodiments, a host cell comprising a nucleic acid encoding an antibody described herein is provided. In some embodiments, a method of producing an antibody is provided comprising culturing a host cell comprising a nucleic acid encoding an antibody described herein such that the antibody is produced.

In some embodiments, an immunoconjugate is provided, comprising the antibody described herein and a cytotoxic agent. In some embodiments, the immunoconjugate has the formula Ab-(L-D)p, wherein: (a) Ab is the antibody descirbed herein; (b) L is a linker; (c) D is a cytotoxic agent; and (d) p ranges from 1-8. In some embodiments, p ranges from 2-5. In some embodiments, the cytotoxic agent is selected from a maytansinoid, a calicheamicin, a pyrrolobenzodiazepine, and a nemorubicin derivative.

In some embodiments, D is a pyrrolobenzodiazepine of Formula A:

A wherein the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{3-8}$ heterocyclyl and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms and/or aromatic rings that are optionally substituted; and X and X' are independently selected from O, S and N(H).

In some embodiments, D has the structure:

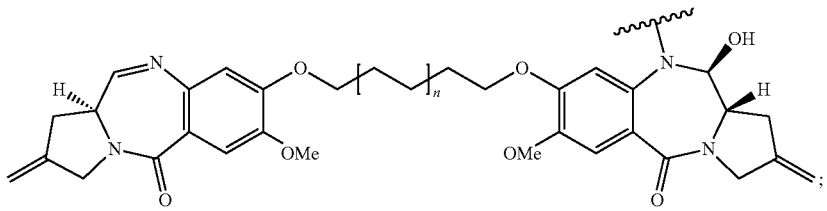

wherein n is 0 or 1.

In some embodiments, D is a nemorubicin derivative. In some embodiments, D has a structure selected from:

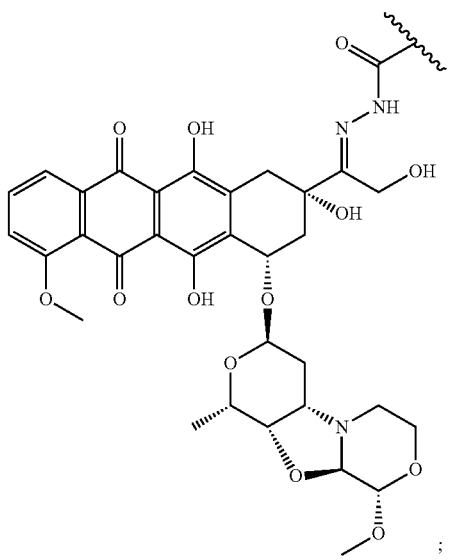

; and

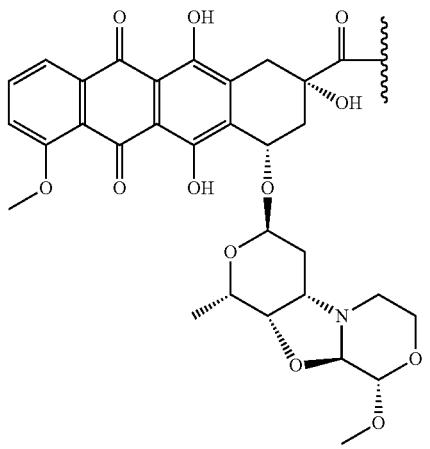

In some embodiments, an immunoconjugate comprising an antibody described herein is provided wherein the linker is cleavable by a protease. In some embodiments, the linker is acid-labile. In some embodiments, the linker comprises hydrazone.

In some embodiments, an immunoconjugate comprising an antibody described herein is provided, wherein the immunoconjugate has a formula selected from:

effective amount of an antibody described herein or an immunoconjugate described herein under conditions permissive for binding of the antibody or immunoconjugate to GPC3 on the surface of the cell, thereby inhibiting proliferation of the cell. In some embodiments, the cell is a liver cancer cell.

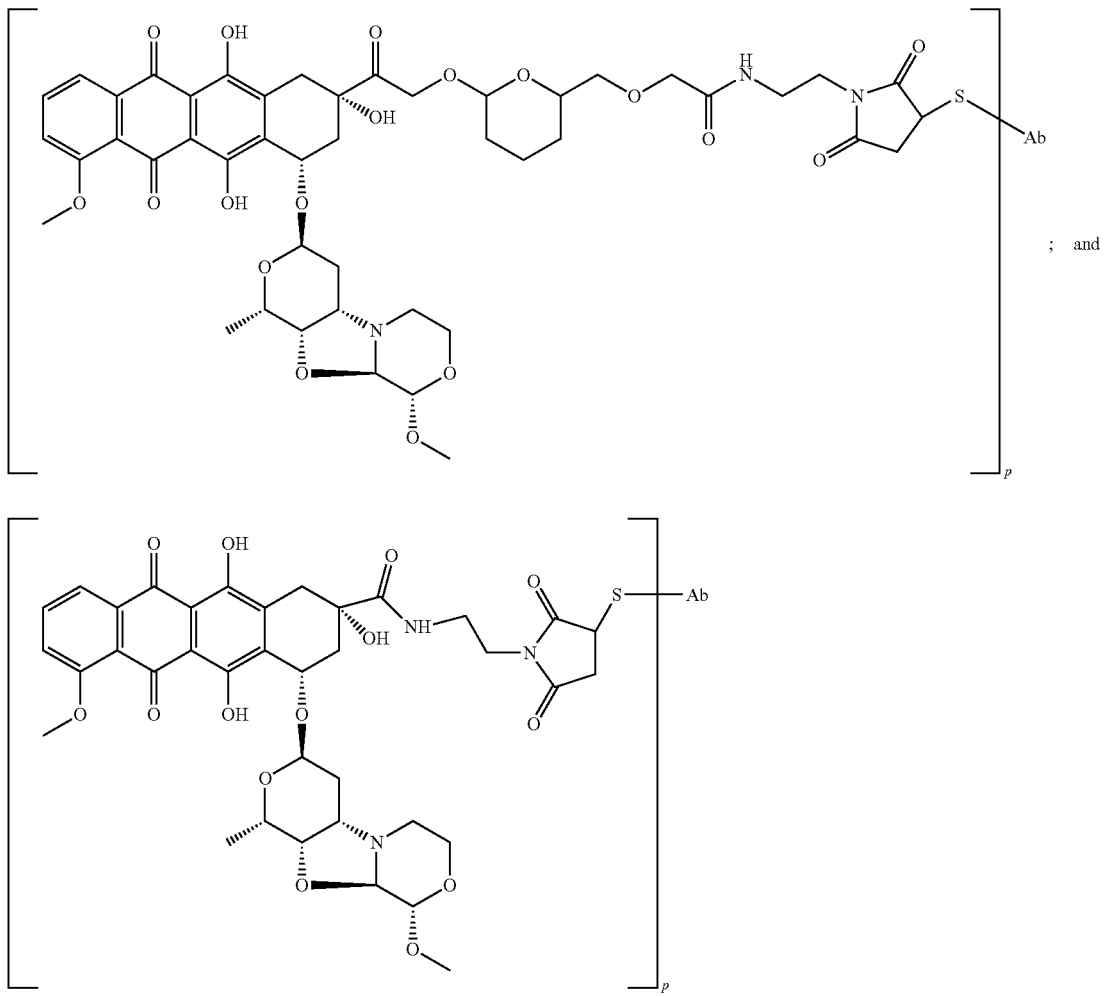

In some embodiments, a pharmaceutical formulation is provided, comprising an immunoconjugate described herein and a pharmaceutically acceptable carrier. In some embodiments, a pharmaceutical formulation is provided comprising an antibody described herein and a pharmaceutically acceptable carrier. In some embodiments, the pharmaceutical formulation further comprises an additional therapeutic agent.

In some embodiments, methods of treating an individual having a GPC3-positive cancer are provided. In some embodiments, a method comprises administering to the individual an effective amount of an antibody described herein, an immunoconjugate described herein, or a pharmaceutical formulation described herein. In some embodiments, the GPC3-positive cancer is liver cancer. In some embodiments, a method further comprises administering an additional therapeutic agent to the individual.

In some embodiments, methods of inhibiting proliferation of a GPC3-positive cell are provided. In some embodiments, a method comprises administering to the individual an In some embodiments, an antibody described herein is conjugated to a label. In some embodiments, the label is a positron emitter. In some embodiments, the positron emitter is $^{89}$Zr.

In some embodiments, methods of detecting human GPC3 in a biological sample are provided. In some embodiments, a method comprises contacting the biological sample with an anti-GPC3 antibody described herein under conditions permissive for binding of the anti-GPC3 antibody to a naturally occurring human GPC3, and detecting whether a complex is formed between the anti-GPC3 antibody and a naturally occurring human GPC3 in the biological sample. In some embodiments, the biological sample is a liver cancer sample. In some embodiments, methods for detecting a GPC3-positive cancer are provided. In some embodiments, a method comprises (i) administering a labeled anti-GPC3 antibody to a subject having or suspected of having a GPC3-positive cancer, wherein the labeled anti-GPC3 antibody comprises an anti-GPC3 antibody described herein, and (ii) detecting the labeled anti-GPC3 antibody in the subject, wherein detection of the labeled anti-GPC3 antibody indicates a GPC3-positive cancer in the subject. In some embodiments, the labeled anti-GPC3 antibody comprises an anti-GPC3 antibody conjugated to a positron emitter. In some embodiments, the positron emitter is $^{89}$Zr.

BRIEF DESCRIPTION OF THE FIGURES

FIG. 4A-B shows alignment of the (A) light chain variable region sequences and (B) heavy chain variable region sequences of anti-GPC3 antibodies 7H1, 4A11, 15G1, and 4G7.

FIG. 11 shows an alignment of GPC3 from human, cynomolgus monkey, rhesus macaque, mouse, and rat, as described in Example 2.

FIG. 12A-B shows (A) the structure of maleimide acetal PNU-159682 antibody-drug conjugate and (B) the structure of monomethyl disulfide N10-linked PBD antibody-drug conjugate, as discussed in Example 5.

FIG. 13A-B show expression of GPC3 on the surface of (A) HepG2 X1 cells and (B) isolated HepG2 X1 xenograft tumor cells, detecting using antibodies 4G7, 7H1, and 4A11 by FACS, as described in Example 6.

DETAILED DESCRIPTION

I. Definitions

Figure 1:
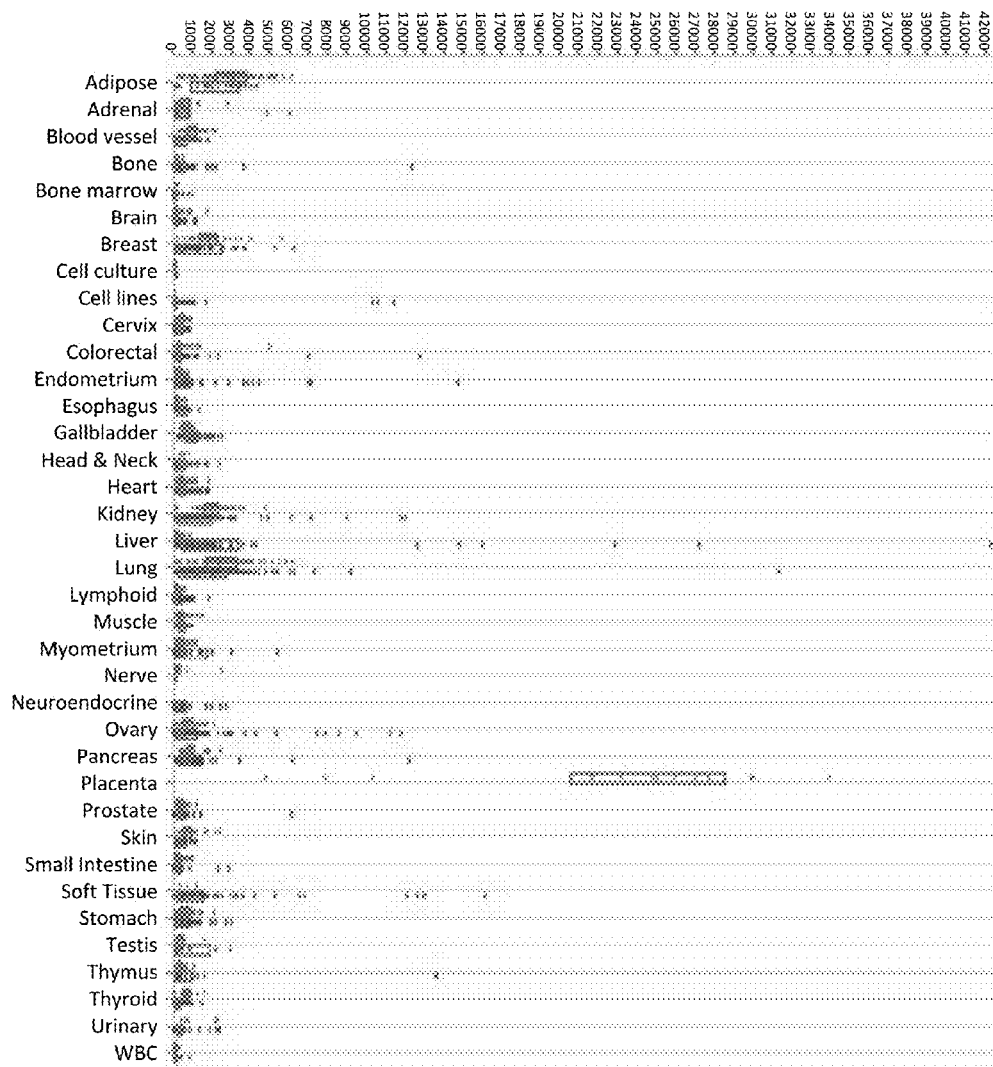
FIG. 1 shows expression of GPC3 in normal and diseased and tumor tissues, as described in Example 1.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-GPC3 antibody" and "an antibody that binds to GPC3" refer to an antibody that is capable of binding GPC3 with sufficient affinity such that the antibody is useful as a diagnostic and/or therapeutic agent in targeting GPC3. In one embodiment, the extent of binding of an anti-GPC3 antibody to an unrelated, non-GPC3 protein is less than about 10% of the binding of the antibody to GPC3 as measured, e.g., by a radioimmunoassay (RIA). In certain embodiments, an antibody that binds to GPC3 has a dissociation constant (Kd) of ≤1 µM, ≤100 nM, ≤10 nM, ≤5 nm, ≤4 nM, ≤3 nM, ≤2 nM, ≤1 nM, ≤0.1 nM, ≤0.01 nM, or ≤0.001 nM (e.g., 10$^{-8}$ M or less, e.g. from 10$^{-8}$ M to 10$^{-13}$ M, e.g., from 10$^{-9}$ M to 10$^{-13}$ M). In certain embodiments, an anti-GPC3 antibody binds to an epitope of GPC3 that is conserved among GPC3 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to an epitope" within a defined region of a protein is an antibody that requires the presence of one or more of the amino acids within that region for binding to the protein. In certain embodiments, an "antibody that binds to an epitope" within a defined region of a protein is identified by deletion or mutation analysis, in which amino acids of the protein are deleted or mutated, and binding of the antibody to the resulting altered protein (e.g., an altered protein comprising the epitope) is determined to be at least 20% of the binding to unaltered protein. In some embodiments, an "antibody that binds to an epitope" within a defined region of a protein is identified by deletion or mutation analysis, in which amino acids of the protein are deleted or mutated, and binding of the antibody to the resulting altered protein (e.g., an altered protein comprising the epitope) is determined to be at least 30%, at least 40%, at least 50%, at least 60%, at least 70%, at least 80%, or at least 90% of the binding to unaltered protein. Exemplary deletion (truncation) analyses are described in Example 2. In certain embodiments, binding of the antibody is determined by FACS, as described in Example 2, or by a suitable binding assay such as ELISA or surface plasmon resonance assay.

An "antibody that competes for binding to a polypeptide, e.g., GPC3, with a reference antibody refers to an antibody that blocks binding of the reference antibody to the polypeptide in a competition assay by 50% or more, and conversely, the reference antibody blocks binding of the antibody to the polypeptide in a competition assay by 50% or more. An exemplary competition assay is an epitope binning assay as provided herein in Example 2. In some embodiments, competition may be assessed using a surface plasmon resonance assay.

An "epitope spanning the furin cleavage site at amino acids R358/S359" refers to an epitope that comprises one or more GPC3 amino acid residues that are N-terminal to S359 and one or more amino acid residues that are C-terminal to R358. In certain embodiments, binding of an antibody to such an epitope can be determined by deletion or mutation analysis, in which one or more GPC3 amino acid residues that are N-terminal to S359 and/or one or more amino acid residues that are C-terminal to R358 are deleted or mutated, and binding of the antibody to the resulting altered protein (e.g., an altered protein comprising the epitope) is determined to be at least 20% of the binding to unaltered protein. In certain embodiments, binding of an antibody to such an epitope can be determined by deletion or mutation analysis, in which one or more GPC3 amino acid residues that are N-terminal to S359 and/or one or more amino acid residues that are C-terminal to R358 are deleted or mutated, and binding of the antibody to the resulting altered protein (e.g., an altered protein comprising the epitope) is determined to be at least 30%, at least 40%, at least 50%, at least 60%, at least 70%, at least 80%, or at least 90% of the binding to unaltered protein. In some embodiments, an antibody that binds to an epitope spanning the furin cleavage site at amino acids R358/S359 binds to full-length GPC3, but does not bind to an N-terminal fragment of GPC3 ending with amino acid residue R358 (e.g., amino acids 25 to 358 of human GPC3) and does not bind to a C-terminal fragment of GPC3 beginning with amino acids residue S359 (e.g., amino acids 359 to 560 or 359 to 580 of human GPC3).

The terms "cancer" and "cancerous" refer to or describe the physiological condition in mammals that is typically characterized by unregulated cell growth/proliferation. Examples of cancer include, but are not limited to, carcinoma, liver cancer, hepatocellular cancer, pancreatic cancer, lung cancer, colon cancer, breast cancer, prostate cancer, lymphoma (e.g., Hodgkin's and non-Hodgkin's lymphoma), blastoma, sarcoma, and leukemia.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-GPC3 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "GPC3," as used herein, refers to any native, mature GPC3 which results from processing of a GPC3 precursor protein in a cell. The term includes GPC3 from any vertebrate source, including mammals such as primates (e.g. humans and cynomolgus monkeys) and rodents (e.g., mice and rats), unless otherwise indicated. The term also includes naturally occurring variants of GPC3, e.g., splice variants or allelic variants. The amino acid sequence of an exemplary human GPC3 precursor protein, with signal sequence (with signal sequence, amino acids 1-24) is shown in SEQ ID NO:1. The amino acid sequence of an exemplary mature human GPC3 is amino acids 25-580 of SEQ ID NO: 1. The amino acid sequence of nonlimiting exemplary cynomolgus monkey, rhesus macaque, mouse, and rat GPC3 precursor proteins, with signal sequences, are shown in SEQ ID NOs: 37 to 41, respectively.

The term "GPC3-positive cancer" refers to a cancer comprising cells that express GPC3 on their surface. In some embodiments, expression of GPC3 on the cell surface is determined, for example, using antibodies to GPC3 in a method such as immunohistochemistry, FACS, etc. Alternatively, GPC3 mRNA expression is considered to correlate to GPC3 expression on the cell surface and can be determined by a method selected from in situ hybridization and RT-PCR (including quantitative RT-PCR).

The term "GPC3-positive cell" refers to a cell that expresses GPC3 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n-propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—$OCH_3$) and ethoxy (—$OCH_2CH_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

A "$C_1$-$C_{10}$ alkylene" is a straight chain, saturated hydrocarbon group of the formula —($CH_2$)$_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—CH$_2$C≡C—), and 4-pentynyl (—CH$_2$CH$_2$CH$_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

A "C$_5$-C$_{20}$ aryl" is an aryl group with 5 to 20 carbon atoms in the carbocyclic aromatic rings. Examples of C$_5$-C$_{20}$ aryl groups include, but are not limited to, phenyl, naphthyl and anthracenyl. A C$_5$-C$_{20}$ aryl group can be substituted or unsubstituted as described above for aryl groups. A "C$_5$-C$_{14}$ aryl" is an aryl group with 5 to 14 carbon atoms in the carbocyclic aromatic rings. Examples of C$_5$-C$_{14}$ aryl groups include, but are not limited to, phenyl, naphthyl and anthracenyl. A C$_5$-C$_{14}$ aryl group can be substituted or unsubstituted as described above for aryl groups.

An "arylene" is an aryl group which has two covalent bonds and can be in the ortho, meta, or para configurations as shown in the following structures:

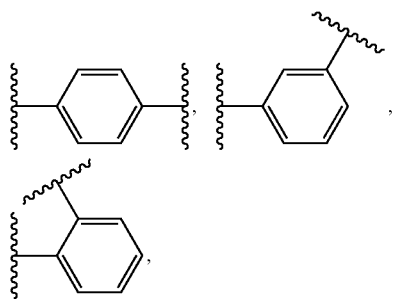

in which the phenyl group can be unsubstituted or substituted with up to four groups including, but not limited to, —C$_1$-C$_8$ alkyl, —O—(C$_1$-C$_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —C$_1$-C$_8$ alkyl and aryl.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or sp$^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$^-_3$, —PO$_3$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently —H, C$_2$-C$_{18}$ alkyl, C$_6$-C$_{20}$ aryl, C$_3$-C$_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W.A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_3$-$C_{20}$ heterocycle" refers to an aromatic or non-aromatic $C_3$-$C_8$ carbocycle in which one to four of the ring carbon atoms are independently replaced with a heteroatom from the group consisting of O, S and N. A $C_3$-$C_{20}$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_{20}$ heterocyclo" refers to a $C_3$-$C_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —(CR$_2$)$_n$O(CR$_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to GPC3 and immunoconjugates comprising such antibodies. Antibodies and immunoconjugates of the invention are useful, e.g., for the diagnosis or treatment of GPC3-positive cancers.

A. Exemplary Anti-GPC3 Antibodies

Provided herein are isolated antibodies that bind to GPC3. An exemplary naturally occurring human GPC3 precursor protein sequence, with signal sequence (amino acids 1-24) is provided in SEQ ID NO: 1, and the corresponding mature GPC3 protein sequence corresponding to amino acids 25-580 of SEQ ID NO: 1.

In certain embodiments, an anti-GPC3 antibody has at least one or more of the following characteristics, in any combination:
a) binds to recombinant human GPC3;
b) binds to recombinant cynomolgus monkey GPC3;
c) binds to endogenous GPC3 on the surface of HepG2 cells;
d) binds to cynomolgus monkey GPC3 expressed on the surface of 293 cells;
e) binds to endogenous GPC3 on the surface of a cancer cell;
f) binds to endogenous GPC3 on the surface of hepatocellular carcinoma cell;
g) binds to endogenous GPC3 on the surface of cells of a cell line selected from HepG2, Hep3B, Huh7, and JHH-7;
h) binds to an epitope within amino acids 25 to 137 of human GPC3;
i) binds to an epitope spanning the furin cleavage site at amino acids R358/S359 of human GPC3;
j) binds to full-length mature human GPC3 (e.g., amino acids 25 to 560 or amino acids 25 to 580 of SEQ ID NO: 1), but does not bind to an N-terminal fragment of human GPC3 (amino acids 25 to 358 of SEQ ID NO: 1) or to a C-terminal fragment of human GPC3 (amino acids 359 to 560 (without GPI link) or amino acids 359 to 580 (with GPI link) of SEQ ID NO: 1)
k) binds to an epitope within amino acids 420 to 470 of human GPC3;
l) binds to an epitope within amino acids 470 to 509 of human GPC3;
m) competes for binding to human GPC3 with antibody 7H1;
n) competes for binding to human GPC3 with antibody 4G7;
o) competes for binding to human GPC3 with antibody 15G1; and/or
p) competes for binding to human GPC3 with antibody 4A11.

In some embodiments, the characteristics of the antibody are determined as described herein, e.g., in the Examples below. In some embodiments, epitope binding is determined using deletion (truncation) analyses, e.g., as described in Example 2. In some embodiments, epitope binding is determined by FACS, e.g., as described in Example 2, or by a suitable binding assay such as ELISA or surface plasmon resonance assay. As a nonlimiting example, in some embodiments, full-length GPC3 or a GPC3 fragment is expressed on the surface of cells (such as 293 cells) and antibody binding to the GPC3 on the surface of the cells is detected by FACS.

Antibody 7H1 and Other Embodiments

Certain embodiments provided herein are based, in part, on the development of antibody 7H1, which binds to an epitope within amino acids 25 to 137 of human GPC3. In some embodiments, an antibody provided herein binds to an epitope within amino acids 25 to 137 of human GPC3. In some such embodiments, an antibody provided herein comprises one or more HVR sequences of antibody 7H1.

In some embodiments, the invention provides an anti-GPC3 antibody comprising at least one, two, three, four, five, or six HVRs selected from (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9.

In one aspect, the invention provides an antibody comprising at least one, at least two, or all three VH HVR sequences selected from (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO: 6. In one embodiment, the antibody comprises HVR-H3 comprising the amino acid sequence of SEQ ID NO: 6. In another embodiment, the antibody comprises HVR-H3 comprising the amino acid sequence of SEQ ID NO: 6 and HVR-L3 comprising the amino acid sequence of SEQ ID NO: 9. In a further embodiment, the antibody comprises HVR-H3 comprising the amino acid sequence of SEQ ID NO: 6, HVR-L3 comprising the amino acid sequence of SEQ ID NO: 9, and HVR-H2 comprising the amino acid sequence of SEQ ID NO: 5. In a further embodiment, the antibody comprises (a) HVR-H1 comprising the amino acid sequence of SEQ ID NO: 4; (b) HVR-H2 comprising the amino acid sequence of SEQ ID NO: 5; and (c) HVR-H3 comprising the amino acid sequence of SEQ ID NO: 6.

In another aspect, the invention provides an antibody comprising at least one, at least two, or all three VL HVR sequences selected from (a) HVR-L1 comprising the amino acid sequence of SEQ ID NO: 7; (b) HVR-L2 comprising the amino acid sequence of SEQ ID NO: 8; and (c) HVR-L3 comprising the amino acid sequence of SEQ ID NO: 9. In one embodiment, the antibody comprises (a) HVR-L1 comprising the amino acid sequence of SEQ ID NO: 7; (b) HVR-L2 comprising the amino acid sequence of SEQ ID NO: 8; and (c) HVR-L3 comprising the amino acid sequence of SEQ ID NO: 9.

In another aspect, an antibody of the invention comprises (a) a VH domain comprising at least one, at least two, or all three VH HVR sequences selected from (i) HVR-H1 comprising the amino acid sequence of SEQ ID NO: 4, (ii) HVR-H2 comprising the amino acid sequence of SEQ ID NO: 5, and (iii) HVR-H3 comprising an amino acid sequence selected from SEQ ID NO: 6; and (b) a VL domain comprising at least one, at least two, or all three VL HVR sequences selected from (i) HVR-L1 comprising the amino acid sequence of SEQ ID NO: 7, (ii) HVR-L2 comprising the amino acid sequence of SEQ ID NO: 8, and (c) HVR-L3 comprising the amino acid sequence of SEQ ID NO: 9.

In another aspect, the invention provides an antibody comprising (a) HVR-H1 comprising the amino acid sequence of SEQ ID NO: 4; (b) HVR-H2 comprising the amino acid sequence of SEQ ID NO: 5; (c) HVR-H3 comprising the amino acid sequence of SEQ ID NO: 6; (d) HVR-L1 comprising the amino acid sequence of SEQ ID NO: 7; (e) HVR-L2 comprising the amino acid sequence of SEQ ID NO: 8; and (f) HVR-L3 comprising the amino acid sequence of SEQ ID NO: 9.

In any of the above embodiments, an anti-GPC3 antibody is humanized. In one embodiment, an anti-GPC3 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-GPC3 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 2. In certain embodiments, a VH sequence having at least 90%, 91%, 92%, 93%, 94%, 95%, 96%, 97%, 98%, or 99% identity to the amino acid sequence of SEQ ID NO: 2 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 2. In certain embodiments, a total of 1 to 5 amino acids have been substituted, inserted and/or deleted in SEQ ID NO: 2. In certain embodiments, substitutions, insertions, or deletions occur in regions outside the HVRs (i.e., in the FRs). Optionally, the anti-GPC3 antibody comprises the VH sequence of SEQ ID NO: 2, including post-translational modifications of that sequence. In a particular embodiment, the VH comprises one, two or three HVRs selected from: (a) HVR-H1 comprising the amino acid sequence of SEQ ID NO: 4, (b) HVR-H2 comprising the amino acid sequence of SEQ ID NO: 5, and (c) HVR-H3 comprising the amino acid sequence of SEQ ID NO: 6.

In another aspect, an anti-GPC3 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 3. In certain embodiments, a VL sequence having at least 90%, 91%, 92%, 93%, 94%, 95%, 96%, 97%, 98%, or 99% identity to the amino acid sequence of SEQ ID NO: 3 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 3. In certain embodiments, a total of 1 to 5 amino acids have been substituted, inserted and/or deleted in SEQ ID NO: 3. In certain embodiments, the substitutions, insertions, or deletions occur in regions outside the HVRs (i.e., in the FRs). Optionally, the anti-GPC3 antibody comprises the VL sequence of SEQ ID NO: 3, including post-translational modifications of that sequence. In a particular embodiment, the VL comprises one, two or three HVRs selected from (a) HVR-L1 comprising the amino acid sequence of SEQ ID NO: 7; (b) HVR-L2 comprising the amino acid sequence of SEQ ID NO: 8; and (c) HVR-L3 comprising the amino acid sequence of SEQ ID NO: 9.

In another aspect, an anti-GPC3 antibody is provided, wherein the antibody comprises a VH as in any of the embodiments provided above, and a VL as in any of the embodiments provided above. In one embodiment, the antibody comprises the VH and VL sequences in SEQ ID NO: 2 and SEQ ID NO: 3, respectively, including post-translational modifications of those sequences. In another embodiment, an anti-GPC3 antibody comprises a humanized form of an antibody comprising the VH and VL sequences in SEQ ID NO: 2 and SEQ ID NO: 3, respectively.

In a further aspect, provided are herein are antibodies that bind to the same epitope as an anti-GPC3 antibody provided herein. For example, in certain embodiments, an antibody is provided that binds to the same epitope as an anti-GPC3 antibody comprising a VH sequence of SEQ ID NO: 2 and a VL sequence of SEQ ID NO: 3, respectively.

Provided herein are antibodies comprising a light chain variable domain comprising the HVR1-LC, HVR2-LC and HVR3-LC sequence according to Kabat numbering as depicted in FIG. 4B and a heavy chain variable domain comprising the HVR1-HC, HVR2-HC and HVR3-HC sequence according to Kabat numbering as depicted in FIG. 4A. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 4B. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 4A.

In a further aspect of the invention, an anti-GPC3 antibody according to any of the above embodiments is a monoclonal antibody, including a human antibody. In one embodiment, an anti-GPC3 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-GPC3 antibody according to any of the above embodiments may incorporate any of the features, singly or in combination, as described below.

Antibody 4A11 and Other Embodiments

Certain embodiments provided herein are based, in part, on the development of antibody 4A11, which binds to an epitope within amino acids 470 to 509 of human GPC3. In some embodiments, an antibody provided herein binds to an epitope within amino acids 470 to 509 of human GPC3. In some such embodiments, an antibody provided herein comprises one or more HVR sequences of antibody 4A11.

In some embodiments, the invention provides an anti-GPC3 antibody comprising at least one, two, three, four, five, or six HVRs selected from (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17.

In one aspect, the invention provides an antibody comprising at least one, at least two, or all three VH HVR sequences selected from (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14. In one embodiment, the antibody comprises HVR-H3 comprising the amino acid sequence of SEQ ID NO: 14. In another embodiment, the antibody comprises HVR-H3 comprising the amino acid sequence of SEQ ID NO: 14 and HVR-L3 comprising the amino acid sequence of SEQ ID NO: 17. In a further embodiment, the antibody comprises HVR-H3 comprising the amino acid sequence of SEQ ID NO: 14, HVR-L3 comprising the amino acid sequence of SEQ ID NO: 17, and HVR-H2 comprising the amino acid sequence of SEQ ID NO: 13. In a further embodiment, the antibody comprises (a) HVR-H1 comprising the amino acid sequence of SEQ ID NO: 12; (b) HVR-H2 comprising the amino acid sequence of SEQ ID NO: 13; and (c) HVR-H3 comprising the amino acid sequence of SEQ ID NO: 14.

In another aspect, the invention provides an antibody comprising at least one, at least two, or all three VL HVR sequences selected from (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17. In one embodiment, the antibody comprises (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17.

In another aspect, an antibody of the invention comprises (a) a VH domain comprising at least one, at least two, or all three VH HVR sequences selected from (i) HVR-H1 comprising the amino acid sequence of SEQ ID NO: 12, (ii) HVR-H2 comprising the amino acid sequence of SEQ ID NO: 13, and (iii) HVR-H3 comprising an amino acid sequence selected from SEQ ID NO: 14; and (b) a VL domain comprising at least one, at least two, or all three VL HVR sequences selected from (i) HVR-L1 comprising the amino acid sequence of SEQ ID NO: 15, (ii) HVR-L2 comprising the amino acid sequence of SEQ ID NO: 16, and (c) HVR-L3 comprising the amino acid sequence of SEQ ID NO: 17.

In another aspect, the invention provides an antibody comprising (a) HVR-H1 comprising the amino acid sequence of SEQ ID NO: 12; (b) HVR-H2 comprising the amino acid sequence of SEQ ID NO: 13; (c) HVR-H3 comprising the amino acid sequence of SEQ ID NO: 14; (d) HVR-L1 comprising the amino acid sequence of SEQ ID NO: 15; (e) HVR-L2 comprising the amino acid sequence of SEQ ID NO: 16; and (f) HVR-L3 comprising the amino acid sequence of SEQ ID NO: 17.

In any of the above embodiments, an anti-GPC3 antibody is humanized. In one embodiment, an anti-GPC3 antibody comprises HVRs as in any of the above embodiments, and further comprises a human acceptor framework, e.g. a human immunoglobulin framework or a human consensus framework. In certain embodiments, the human acceptor framework is the human VL kappa I consensus (VL$_{KI}$) framework and/or the VH framework VH$_1$. In certain embodiments, the human acceptor framework is the human VL kappa I consensus (VL$_{KI}$) framework and/or the VH framework VH$_1$ comprising any one of the following mutations.

In another aspect, an anti-GPC3 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10. In certain embodiments, a VH sequence having at least 90%, 91%, 92%, 93%, 94%, 95%, 96%, 97%, 98%, or 99% identity to the amino acid sequence of SEQ ID NO: 10 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 10. In certain embodiments, a total of 1 to 5 amino acids have been substituted, inserted and/or deleted in SEQ ID NO: 10. In certain embodiments, substitutions, insertions, or deletions occur in regions outside the HVRs (i.e., in the FRs). Optionally, the anti-GPC3 antibody comprises the VH sequence of SEQ ID NO: 10, including post-translational modifications of that sequence. In a particular embodiment, the VH comprises one, two or three HVRs selected from: (a) HVR-H1 comprising the amino acid sequence of SEQ ID NO: 12, (b) HVR-H2 comprising the amino acid sequence of SEQ ID NO: 13, and (c) HVR-H3 comprising the amino acid sequence of SEQ ID NO: 14.

In another aspect, an anti-GPC3 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 11. In certain embodiments, a VL sequence having at least 90%, 91%, 92%, 93%, 94%, 95%, 96%, 97%, 98%, or 99% identity to the amino acid sequence of SEQ ID NO: 11 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 11. In certain embodiments, a total of 1 to 5 amino acids have been substituted, inserted and/or deleted in SEQ ID NO: 11. In certain embodiments, the substitutions, insertions, or deletions occur in regions outside the HVRs (i.e., in the FRs). Optionally, the anti-GPC3 antibody comprises the VL sequence of SEQ ID NO: 11, including post-translational modifications of that sequence. In a particular embodiment, the VL comprises one, two or three HVRs selected from (a) HVR-L1 comprising the amino acid sequence of SEQ ID NO: 15; (b) HVR-L2 comprising the amino acid sequence of SEQ ID NO: 16; and (c) HVR-L3 comprising the amino acid sequence of SEQ ID NO: 17.

In another aspect, an anti-GPC3 antibody is provided, wherein the antibody comprises a VH as in any of the embodiments provided above, and a VL as in any of the embodiments provided above. In one embodiment, the antibody comprises the VH and VL sequences in SEQ ID NO: 10 and SEQ ID NO: 11, respectively, including post-translational modifications of those sequences. In another embodiment, an anti-GPC3 antibody comprises a humanized form of an antibody comprising the VH and VL sequences in SEQ ID NO: 10 and SEQ ID NO: 11, respectively.

In a further aspect, provided are herein are antibodies that bind to the same epitope as an anti-GPC3 antibody provided herein. For example, in certain embodiments, an antibody is provided that binds to the same epitope as an anti-GPC3 antibody comprising a VH sequence of SEQ ID NO: 10 and a VL sequence of SEQ ID NO: 11, respectively.

Provided herein are antibodies comprising a light chain variable domain comprising the HVR1-LC, HVR2-LC and HVR3-LC sequence according to Kabat numbering as depicted in FIG. 4B and a heavy chain variable domain comprising the HVR1-HC, HVR2-HC and HVR3-HC sequence according to Kabat numbering as depicted in FIG. 4A. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 4B. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 4A.

In a further aspect of the invention, an anti-GPC3 antibody according to any of the above embodiments is a monoclonal antibody, including a human antibody. In one embodiment, an anti-GPC3 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-GPC3 antibody according to any of the above embodiments may incorporate any of the features, singly or in combination, as described below.

Antibody 15G1 and Other Embodiments

Certain embodiments provided herein are based, in part, on the development of antibody 15G1, which binds to an epitope within amino acids 420 to 470 of human GPC3. In some embodiments, an antibody provided herein binds to an epitope within amino acids 420 to 470 of human GPC3. In some such embodiments, an antibody provided herein comprises one or more HVR sequences of antibody 15G1.

In some embodiments, the invention provides an anti-GPC3 antibody comprising at least one, two, three, four, five, or six HVRs selected from (a) HVR-H1 comprising the amino acid sequence of SEQ ID NO: 28; (b) HVR-H2 comprising the amino acid sequence of SEQ ID NO: 29; (c) HVR-H3 comprising the amino acid sequence of SEQ ID NO: 30; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33.

In one aspect, the invention provides an antibody comprising at least one, at least two, or all three VH HVR sequences selected from (a) HVR-H1 comprising the amino acid sequence of SEQ ID NO: 28; (b) HVR-H2 comprising the amino acid sequence of SEQ ID NO: 29; and (c) HVR-H3 comprising the amino acid sequence of SEQ ID NO: 30. In one embodiment, the antibody comprises HVR-H3 comprising the amino acid sequence of SEQ ID NO: 30. In another embodiment, the antibody comprises HVR-H3 comprising the amino acid sequence of SEQ ID NO: 30 and HVR-L3 comprising the amino acid sequence of SEQ ID NO: 33. In a further embodiment, the antibody comprises HVR-H3 comprising the amino acid sequence of SEQ ID NO: 30, HVR-L3 comprising the amino acid sequence of SEQ ID NO: 33, and HVR-H2 comprising the amino acid sequence of SEQ ID NO: 29. In a further embodiment, the antibody comprises (a) HVR-H1 comprising the amino acid sequence of SEQ ID NO: 28; (b) HVR-H2 comprising the amino acid sequence of SEQ ID NO: 29; and (c) HVR-H3 comprising the amino acid sequence of SEQ ID NO: 30.

In another aspect, the invention provides an antibody comprising at least one, at least two, or all three VL HVR sequences selected from (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33. In one embodiment, the antibody comprises (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33.

In another aspect, an antibody of the invention comprises (a) a VH domain comprising at least one, at least two, or all three VH HVR sequences selected from (i) HVR-H1 comprising the amino acid sequence of SEQ ID NO: 28, (ii) HVR-H2 comprising the amino acid sequence of SEQ ID NO: 29, and (iii) HVR-H3 comprising an amino acid sequence selected from SEQ ID NO: 30; and (b) a VL domain comprising at least one, at least two, or all three VL HVR sequences selected from (i) HVR-L1 comprising the amino acid sequence of SEQ ID NO: 31, (ii) HVR-L2 comprising the amino acid sequence of SEQ ID NO: 32, and (c) HVR-L3 comprising the amino acid sequence of SEQ ID NO: 33.

In another aspect, the invention provides an antibody comprising (a) HVR-H1 comprising the amino acid sequence of SEQ ID NO: 28; (b) HVR-H2 comprising the amino acid sequence of SEQ ID NO: 29; (c) HVR-H3 comprising the amino acid sequence of SEQ ID NO: 30; (d) HVR-L1 comprising the amino acid sequence of SEQ ID NO: 31; (e) HVR-L2 comprising the amino acid sequence of SEQ ID NO: 32; and (f) HVR-L3 comprising the amino acid sequence of SEQ ID NO: 33.

In any of the above embodiments, an anti-GPC3 antibody is humanized. In one embodiment, an anti-GPC3 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-GPC3 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 26. In certain embodiments, a VH sequence having at least 90%, 91%, 92%, 93%, 94%, 95%, 96%, 97%, 98%, or 99% identity to the amino acid sequence of SEQ ID NO: 26 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 26. In certain embodiments, a total of 1 to 5 amino acids have been substituted, inserted and/or deleted in SEQ ID NO: 26. In certain embodiments, substitutions, insertions, or deletions occur in regions outside the HVRs (i.e., in the FRs). Optionally, the anti-GPC3 antibody comprises the VH sequence of SEQ ID NO: 26, including post-translational modifications of that sequence. In a particular embodiment, the VH comprises one, two or three HVRs selected from: (a) HVR-H1 comprising the amino acid sequence of SEQ ID NO: 28, (b) HVR-H2 comprising the amino acid sequence of SEQ ID NO: 29, and (c) HVR-H3 comprising the amino acid sequence of SEQ ID NO: 30.

In another aspect, an anti-GPC3 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 27. In certain embodiments, a VL sequence having at least 90%, 91%, 92%, 93%, 94%, 95%, 96%, 97%, 98%, or 99% identity to the amino acid sequence of SEQ ID NO: 27 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 27. In certain embodiments, a total of 1 to 5 amino acids have been substituted, inserted and/or deleted in SEQ ID NO: 27. In certain embodiments, the substitutions, insertions, or deletions occur in regions outside the HVRs (i.e., in the FRs). Optionally, the anti-GPC3 antibody comprises the VL sequence of SEQ ID NO: 27, including post-translational modifications of that sequence. In a particular embodiment, the VL comprises one, two or three HVRs selected from (a) HVR-L1 comprising the amino acid sequence of SEQ ID NO: 31; (b) HVR-L2 comprising the amino acid sequence of SEQ ID NO: 32; and (c) HVR-L3 comprising the amino acid sequence of SEQ ID NO: 33.

In another aspect, an anti-GPC3 antibody is provided, wherein the antibody comprises a VH as in any of the embodiments provided above, and a VL as in any of the embodiments provided above. In one embodiment, the antibody comprises the VH and VL sequences in SEQ ID NO: 26 and SEQ ID NO: 27, respectively, including post-translational modifications of those sequences. In another embodiment, an anti-GPC3 antibody comprises a humanized form of an antibody comprising the VH and VL sequences in SEQ ID NO: 26 and SEQ ID NO: 27, respectively.

In a further aspect, provided are herein are antibodies that bind to the same epitope as an anti-GPC3 antibody provided herein. For example, in certain embodiments, an antibody is provided that binds to the same epitope as an anti-GPC3 antibody comprising a VH sequence of SEQ ID NO: 26 and a VL sequence of SEQ ID NO: 27, respectively.

Provided herein are antibodies comprising a light chain variable domain comprising the HVR1-LC, HVR2-LC and HVR3-LC sequence according to Kabat numbering as depicted in FIG. 4B and a heavy chain variable domain comprising the HVR1-HC, HVR2-HC and HVR3-HC sequence according to Kabat numbering as depicted in FIG. 4A. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 4B. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 4A.

In a further aspect of the invention, an anti-GPC3 antibody according to any of the above embodiments is a monoclonal antibody, including a human antibody. In one embodiment, an anti-GPC3 antibody is an antibody fragment, e.g., a Fv, Fab, Fab', scFv, diabody, or F(ab')₂ fragment. In another embodiment, the antibody is a substantially full length antibody, e.g., an IgG1 antibody, IgG2a antibody or other antibody class or isotype as defined herein.

In a further aspect, an anti-GPC3 antibody according to any of the above embodiments may incorporate any of the features, singly or in combination, as described below.

Antibody 4G7 and Other Embodiments

Certain embodiments provided herein are based, in part, on the development of antibody 4G7, which binds to full-length human GPC3, but not to an N-terminal fragment or a C-terminal fragment of human GPC3, suggesting that it binds to an epitope spanning the furin cleavage site at amino acids R358/S359 of human GPC3. In some embodiments, an antibody provided herein binds to fill-length mature human GPC3 but does not bind to an N-terminal fragment of human GPC3 (amino acids 25 to 358 of SEQ ID NO: 1) and does not bind to a C-terminal fragment of human GPC3 (amino acids 359 to 560 (without GPI link) or amino acids 359 to 580 (with GPI link) of SEQ ID NO: 1). In some embodiments, an antibody provided herein binds to an epitope spanning the furin cleavage site at amino acids R358/S359 of human GPC3. In some such embodiments, an antibody provided herein comprises one or more HVR sequences of antibody 4G7.

In some embodiments, the invention provides an anti-GPC3 antibody comprising at least one, two, three, four, five, or six HVRs selected from (a) HVR-H1 comprising the amino acid sequence of SEQ ID NO: 20; (b) HVR-H2 comprising the amino acid sequence of SEQ ID NO: 21; (c) HVR-H3 comprising the amino acid sequence of SEQ ID NO: 22; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25.

In one aspect, the invention provides an antibody comprising at least one, at least two, or all three VH HVR sequences selected from (a) HVR-H1 comprising the amino acid sequence of SEQ ID NO: 20; (b) HVR-H2 comprising the amino acid sequence of SEQ ID NO: 21; and (c) HVR-H3 comprising the amino acid sequence of SEQ ID NO: 22. In one embodiment, the antibody comprises HVR-H3 comprising the amino acid sequence of SEQ ID NO: 22. In another embodiment, the antibody comprises HVR-H3 comprising the amino acid sequence of SEQ ID NO: 22 and HVR-L3 comprising the amino acid sequence of SEQ ID NO: 25. In a further embodiment, the antibody comprises HVR-H3 comprising the amino acid sequence of SEQ ID NO: 22, HVR-L3 comprising the amino acid sequence of SEQ ID NO: 25, and HVR-H2 comprising the amino acid sequence of SEQ ID NO: 21. In a further embodiment, the antibody comprises (a) HVR-H1 comprising the amino acid sequence of SEQ ID NO: 20; (b) HVR-H2 comprising the amino acid sequence of SEQ ID NO: 21; and (c) HVR-H3 comprising the amino acid sequence of SEQ ID NO: 22.

In another aspect, the invention provides an antibody comprising at least one, at least two, or all three VL HVR sequences selected from (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25. In one embodiment, the antibody comprises (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25.

In another aspect, an antibody of the invention comprises (a) a VH domain comprising at least one, at least two, or all three VH HVR sequences selected from (i) HVR-H1 comprising the amino acid sequence of SEQ ID NO: 20, (ii) HVR-H2 comprising the amino acid sequence of SEQ ID NO: 21, and (iii) HVR-H3 comprising an amino acid sequence selected from SEQ ID NO: 22; and (b) a VL domain comprising at least one, at least two, or all three VL HVR sequences selected from (i) HVR-L1 comprising the amino acid sequence of SEQ ID NO: 23, (ii) HVR-L2 comprising the amino acid sequence of SEQ ID NO: 24, and (c) HVR-L3 comprising the amino acid sequence of SEQ ID NO: 25.

In another aspect, the invention provides an antibody comprising (a) HVR-H1 comprising the amino acid sequence of SEQ ID NO: 20; (b) HVR-H2 comprising the amino acid sequence of SEQ ID NO: 21; (c) HVR-H3 comprising the amino acid sequence of SEQ ID NO: 22; (d) HVR-L1 comprising the amino acid sequence of SEQ ID NO: 23; (e) HVR-L2 comprising the amino acid sequence of SEQ ID NO: 24; and (f) HVR-L3 comprising the amino acid sequence of SEQ ID NO: 25.

In any of the above embodiments, an anti-GPC3 antibody is humanized. In one embodiment, an anti-GPC3 antibody comprises HVRs as in any of the above embodiments, and further comprises a human acceptor framework, e.g. a human immunoglobulin framework or a human consensus framework. In certain embodiments, the human acceptor framework is the human VL kappa I consensus ($VL_{KI}$) framework and/or the VH framework $VH_1$. In certain embodiments, the human acceptor framework is the human VL kappa I consensus ($VL_{KI}$) framework and/or the VH framework $VH_1$ comprising any one of the following mutations.

In another aspect, an anti-GPC3 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18. In certain embodiments, a VH sequence having at least 90%, 91%, 92%, 93%, 94%, 95%, 96%, 97%, 98%, or 99% identity to the amino acid sequence of SEQ ID NO: 18 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 18. In certain embodiments, a total of 1 to 5 amino acids have been substituted, inserted and/or deleted in SEQ ID NO: 18. In certain embodiments, substitutions, insertions, or deletions occur in regions outside the HVRs (i.e., in the FRs). Optionally, the anti-GPC3 antibody comprises the VH sequence of SEQ ID NO: 18, including post-translational modifications of that sequence. In a particular embodiment, the VH comprises one, two or three HVRs selected from: (a) HVR-H1 comprising the amino acid sequence of SEQ ID NO: 20, (b) HVR-H2 comprising the amino acid sequence of SEQ ID NO: 21, and (c) HVR-H3 comprising the amino acid sequence of SEQ ID NO: 22.

In another aspect, an anti-GPC3 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 19. In certain embodiments, a VL sequence having at least 90%, 91%, 92%, 93%, 94%, 95%, 96%, 97%, 98%, or 99% identity to the amino acid sequence of SEQ ID NO: 19 contains substitutions (e.g., conservative substitutions), insertions, or deletions relative to the reference sequence, but an anti-GPC3 antibody comprising that sequence retains the ability to bind to GPC3. In certain embodiments, a total of 1 to 10 amino acids have been substituted, inserted and/or deleted in SEQ ID NO: 19. In certain embodiments, a total of 1 to 5 amino acids have been substituted, inserted and/or deleted in SEQ ID NO: 19. In certain embodiments, the substitutions, insertions, or deletions occur in regions outside the HVRs (i.e., in the FRs). Optionally, the anti-GPC3 antibody comprises the VL sequence of SEQ ID NO: 19, including post-translational modifications of that sequence. In a particular embodiment, the VL comprises one, two or three HVRs selected from (a) HVR-L1 comprising the amino acid sequence of SEQ ID NO: 23; (b) HVR-L2 comprising the amino acid sequence of SEQ ID NO: 24; and (c) HVR-L3 comprising the amino acid sequence of SEQ ID NO: 25.

In another aspect, an anti-GPC3 antibody is provided, wherein the antibody comprises a VH as in any of the embodiments provided above, and a VL as in any of the embodiments provided above. In one embodiment, the antibody comprises the VH and VL sequences in SEQ ID NO: 18 and SEQ ID NO: 19, respectively, including post-translational modifications of those sequences. In another embodiment, an anti-GPC3 antibody comprises a humanized form of an antibody comprising the VH and VL sequences in SEQ ID NO: 18 and SEQ ID NO: 19, respectively.

In a further aspect, provided are herein are antibodies that bind to the same epitope as an anti-GPC3 antibody provided herein. For example, in certain embodiments, an antibody is provided that binds to the same epitope as an anti-GPC3 antibody comprising a VH sequence of SEQ ID NO: 18 and a VL sequence of SEQ ID NO: 19, respectively.

Provided herein are antibodies comprising a light chain variable domain comprising the HVR1-LC, HVR2-LC and HVR3-LC sequence according to Kabat numbering as depicted in FIG. 4B and a heavy chain variable domain comprising the HVR1-HC, HVR2-HC and HVR3-HC sequence according to Kabat numbering as depicted in FIG. 4A. In some embodiments, the antibody comprises a light chain variable domain comprising the HVR1-LC, HVR2-LC and/or HVR3-LC sequence, and the FR1-LC, FR2-LC, FR3-LC and/or FR4-LC sequence as depicted in FIG. 4B. In some embodiments, the antibody comprises a heavy chain variable domain comprising the HVR1-HC, HVR2-HC and/or HVR3-HC sequence, and the FR1-HC, FR2-HC, FR3-HC and/or FR4-HC sequence as depicted in FIG. 4A.

In a further aspect of the invention, an anti-GPC3 antibody according to any of the above embodiments is a monoclonal antibody, including a human antibody. In one embodiment, an anti-GPC3 antibody is an antibody fragment, e.g., a Fv, Fab, Fab', scFv, diabody, or F(ab')$_2$ fragment. In another embodiment, the antibody is a substantially full length antibody, e.g., an IgG1 antibody, IgG2a antibody or other antibody class or isotype as defined herein.

In a further aspect, an anti-GPC3 antibody according to any of the above embodiments may incorporate any of the features, singly or in combination, as described below.

1. Antibody Affinity

In certain embodiments, an antibody provided herein has a dissociation constant (Kd) of ≤1 µM, ≤100 nM, ≤50 nM, ≤10 nM, ≤5 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for GPC3 and the other is for any other antigen. In certain embodiments, one of the binding specificities is for GPC3 and the other is for CD3. See, e.g., U.S. Pat. No. 5,821,337. In certain embodiments, bispecific antibodies may bind to two different epitopes of GPC3. Bispecific antibodies may also be used to localize cytotoxic agents to cells which express GPC3. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to GPC3 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.,* 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al.,

*Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-GPC3 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-GPC3 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-GPC3 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-GPC3 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to GPC3. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized GPC3 is incubated in a solution comprising a first labeled antibody that binds to GPC3 (e.g., any of the antibodies described herein) and a second unlabeled antibody that is being tested for its ability to compete with the first antibody for binding to GPC3. The second antibody may be present in a hybridoma supernatant. As a control, immobilized GPC3 is incubated in a solution comprising the first labeled antibody but not the second unlabeled antibody. After incubation under conditions permissive for binding of the first antibody to GPC3, excess unbound antibody is removed, and the amount of label associated with immobilized GPC3 is measured. If the amount of label associated with immobilized GPC3 is substantially reduced in the test sample relative to the control sample, then that indicates that the second antibody is competing with the first antibody for binding to GPC3. See Harlow and Lane (1988) *Antibodies: A Laboratory Manual* ch. 14 (Cold Spring Harbor Laboratory, Cold Spring Harbor, N.Y.).

D. Immunoconjugates

The invention also provides immunoconjugates comprising an anti-GPC3 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

Ab-(L-D)$_p$      I where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), p-aminobenzyloxycarbonyl (a "PAB"), N-Succinimidyl 4-(2-pyridylthio)pentanoate ("SPP"), and 4-(N-maleimidomethyl)cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In some embodiments, a linker component comprises a "stretcher unit" that links an antibody to another linker component or to a drug moiety. Nonlimiting exemplary stretcher units are shown below (wherein the wavy line indicates sites of covalent attachment to an antibody, drug, or additional linker components):

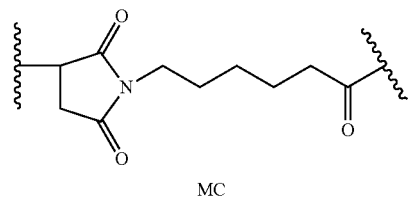

MC

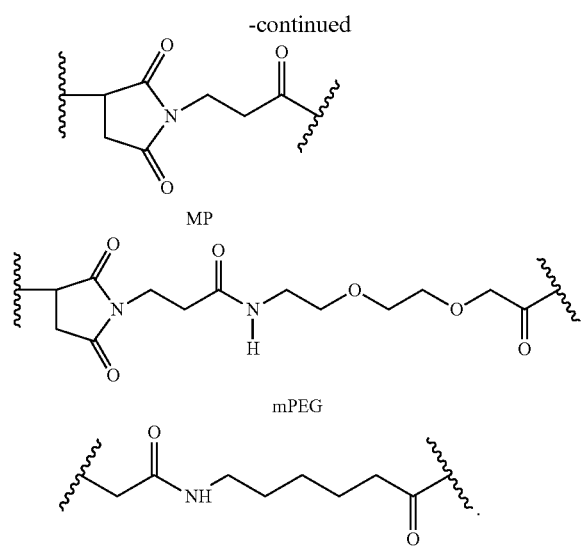

MP mPEG

In some embodiments, a linker component comprises a "spacer" unit that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) Expert Opin. Ther. Patents (2005) 15:1087-1103). In some embodiments, the spacer unit is p-aminobenzyloxycarbonyl (PAB). In some embodiments, an ADC comprising a self-immolative linker has the structure:

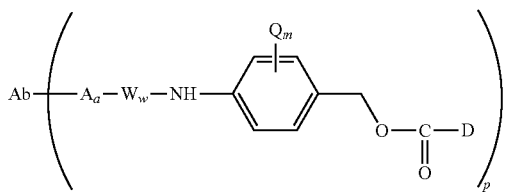

wherein Q is —$C_1$-$C_8$ alkyl, —O—($C_1$-$C_8$ alkyl), -halogen, -nitro, or -cyno; m is an integer ranging from 0 to 4; and p ranges from 1 to about 20. In some embodiments, p ranges from 1 to 10, 1 to 7, 1 to 5, or 1 to 4.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Linkage of a drug to the α-carbon of a glycine residue is another example of a self-immolative spacer that may be useful in ADC (Kingsbury et al (1984) J. Med. Chem. 27:1447).

In some embodiments, linker L may be a dendritic type linker for covalent attachment of more than one drug moiety to an antibody through a branching, multifunctional linker moiety (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I. In some such embodiments, the antibody comprises more than one (linker portion) a substituents, such that more than one drug is coupled to the antibody in the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy)succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido)propionate (SBAP), succinimidyl iodoacetate (SIA), succinimidyl (4-iodoacetyl) aminobenzoate (SIAB), N-succinimidyl-3-(2-pyridyldithio) propionate (SPDP), N-succinimidyl-4-(2-pyridylthio) pentanoate (SPP), succinimidyl 4-(N-maleimidomethyl) cyclohexane-1-carboxylate (SMCC), succinimidyl 4-(p-maleimidophenyl)butyrate (SMPB), succinimidyl 6-[(beta-maleimidopropionamido)hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone)benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

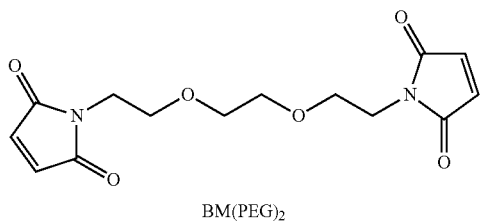

BM(PEG)$_2$

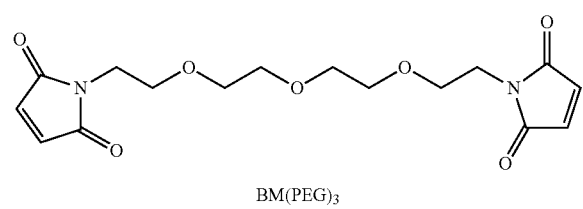

BM(PEG)$_3$

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Dubowchik, et al. (1997) Tetrahedron Letters, 38:5257-60; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties (1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) PNAS 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424,219) (prepared, for example, by the reaction of maytansinol with H$_2$S or P$_2$S$_5$); C-14-alkoxymethyl(demethoxy/CH$_2$OR) (U.S. Pat. No. 4,331,598); C-14-hydroxymethyl or acyloxymethyl (CH$_2$OH or CH$_2$OAc) (U.S. Pat. No. 4,450,254) (prepared, for example, from Nocardia); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

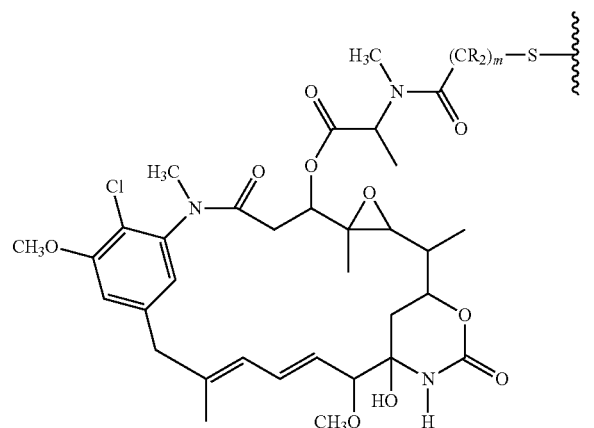

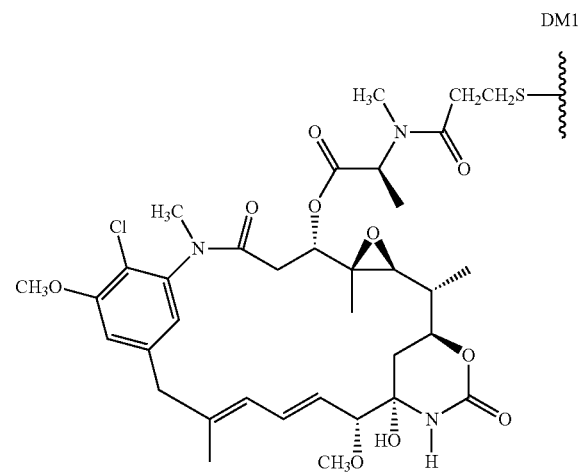

DM1 where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; Liu et al (1996) *Proc. Natl. Acad. Sci USA* 93:8618-8623).

All stereoisomers of the maytansinoid drug moiety are contemplated for the ADC of the invention, i.e. any combination of R and S configurations at the chiral carbons (U.S. Pat. No. 7,276,497; U.S. Pat. No. 6,913,748; U.S. Pat. No. 6,441,163; U.S. Pat. No. 633,410 (RE39151); U.S. Pat. No. 5,208,020; Widdison et al (2006) J. Med. Chem. 49:4392-4408, which are incorporated by reference in their entirety). In some embodiments, the maytansinoid drug moiety has the following stereochemistry:

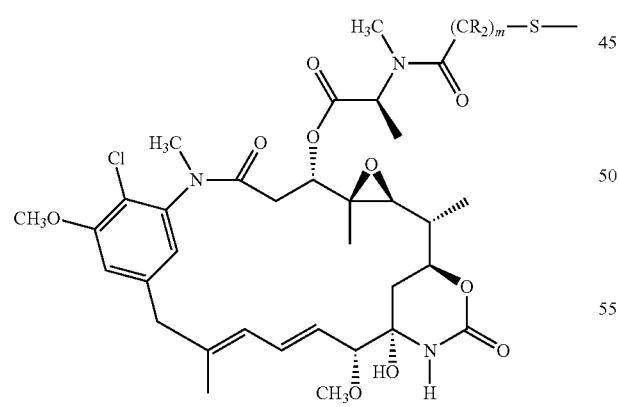

Exemplary embodiments of maytansinoid drug moieties include, but are not limited to, DM1; DM3; and DM4, having the structures:

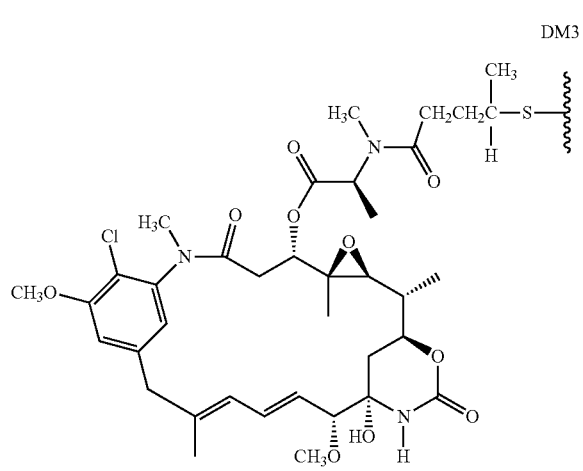

DM3

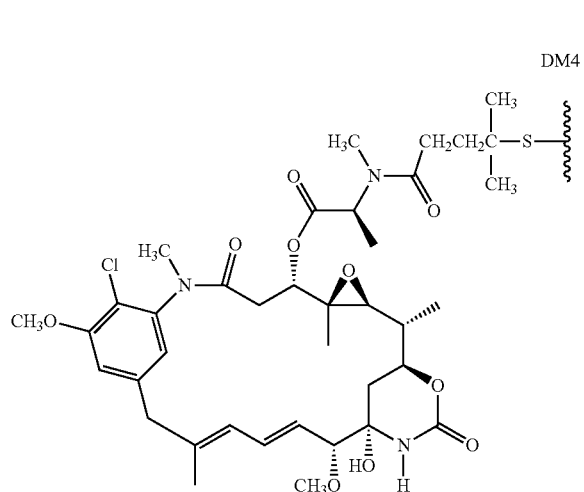

DM4 wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

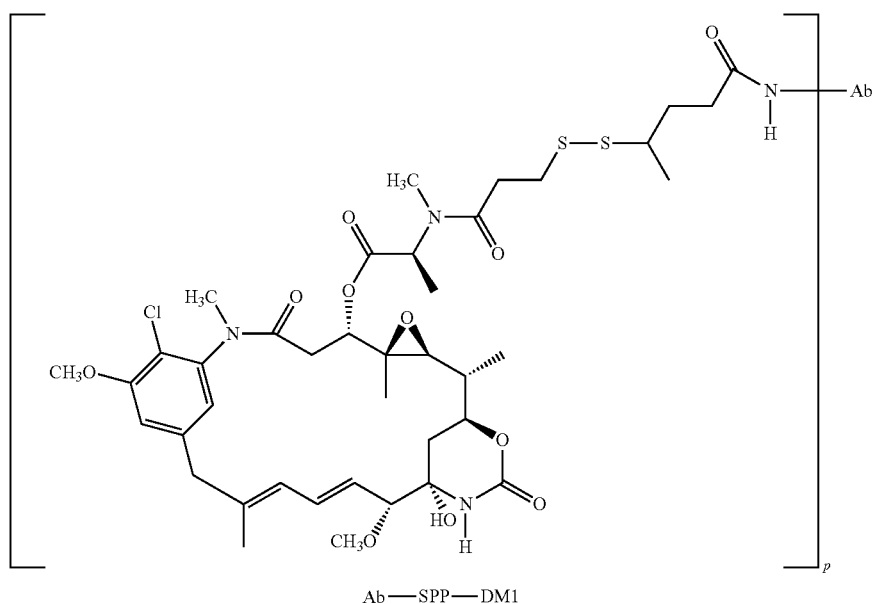
Ab—SPP—DM1
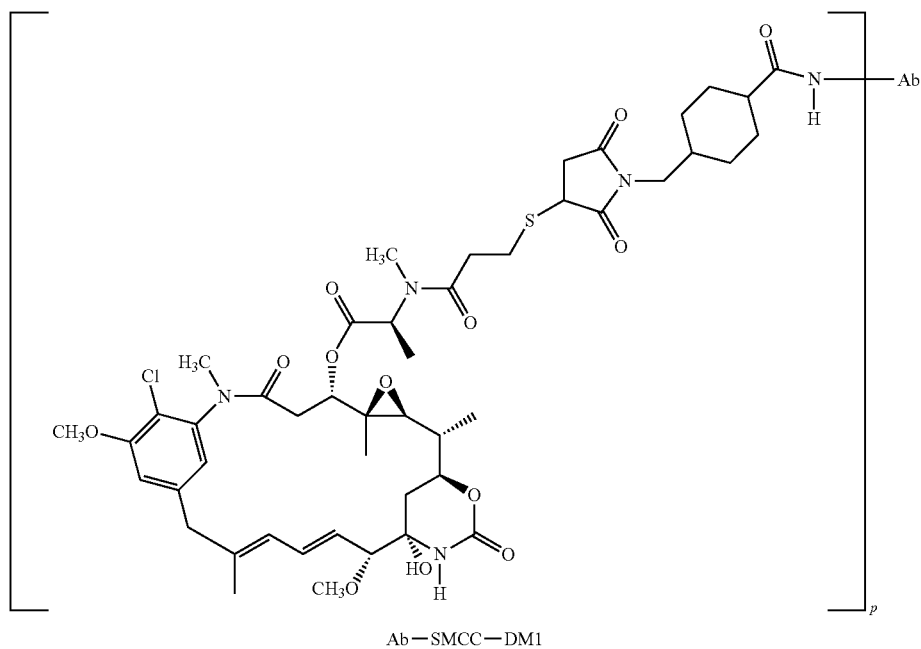
Ab—SMCC—DM1
Exemplary antibody-drug conjugates where DM1 is linked through a BMPEO linker to a thiol group of the antibody have the structure and abbreviation:

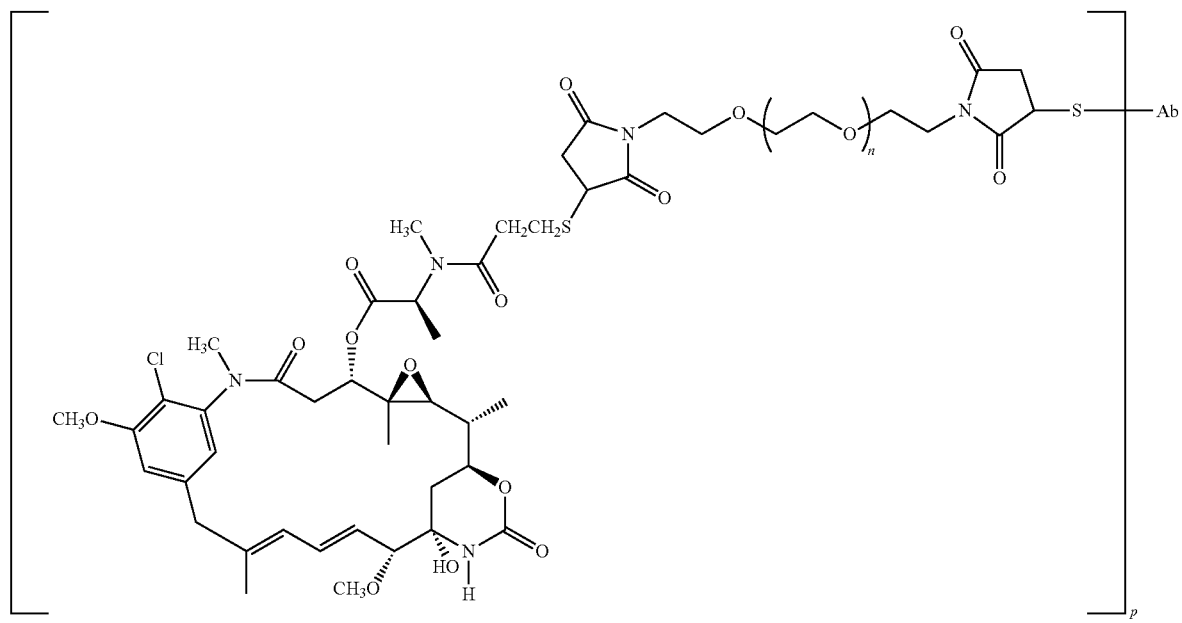

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by reference. See also Liu et al. *Proc. Natl. Acad. Sci. USA* 93:8618-8623 (1996); and Chari et al. *Cancer Research* 52:127-131 (1992).

In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) *Cancer Research* 53:3336-3342; Lode et al., (1998) *Cancer Research* 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. No. 5,712, 374; U.S. Pat. No. 5,714,586; U.S. Pat. No. 5,739,116; and U.S. Pat. No. 5,767,285.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965) *J. Am. Chem. Soc.,* 87:5793-5795; Leimgruber, et al., (1965) *J. Am. Chem. Soc.,* 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. No. 6,884, 799; U.S. Pat. No. 7,049,311; U.S. Pat. No. 7,067,511; U.S. Pat. No. 7,265,105; U.S. Pat. No. 7,511,032; U.S. Pat. No. 7,528,126; U.S. Pat. No. 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) *Acc. Chem. Res.,* 19:230-237). Dimeric PBD compounds bearing C2 aryl substituents have been shown to be useful as cytotoxic agents (Hartley et al (2010) *Cancer Res.* 70(17):6849-6858; Antonow (2010) *J. Med. Chem.* 53(7):2927-2941; Howard et al (2009) *Bioorganic and Med. Chem. Letters* 19(22):6463-6466).

In some embodiments, PBD compounds can be employed as prodrugs by protecting them at the N10 position with a nitrogen protecting group which is removable in vivo (WO 00/12507; WO 2005/023814).

PBD dimers have been conjugated to antibodies and the resulting ADC shown to have anti-cancer properties (US 2010/0203007). Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

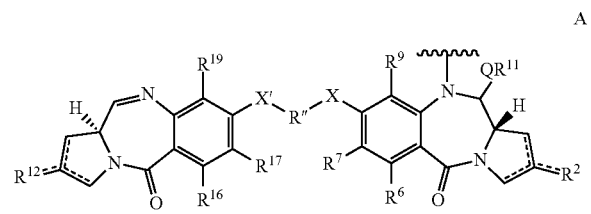

and salts and solvates thereof, wherein:

the wavy line indicates the covalent attachment site to the linker;

the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{1-12}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted C$_{1-12}$ alkyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.

In some embodiments, $R^6$ and $R^{16}$ are H.

In some embodiments, $R^7$ are $R^{17}$ are both OR$^{7A}$, where R$^{7A}$ is optionally substituted C$_{1-4}$ alkyl. In some embodiments, R$^{7A}$ is Me. In some embodiments, R$^{7A}$ is Ch$_2$Ph, where Ph is a phenyl group.

In some embodiments, X is O.

In some embodiments, $R^{11}$ is H.

In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted C$_{5-20}$ aryl or C$_{5-7}$ aryl or C$_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =CH$_2$, =CH—R$^D$, and =C(R$^D$)$_2$. In some embodiments, $R^2$ and $R^{12}$ are each =CH$_2$. In some embodiments, $R^2$ and $R^{12}$ are each H. In some embodiments, $R^2$ and $R^{12}$ are each =O. In some embodiments, $R^2$ and $R^{12}$ are each =CF$_2$. In some embodiments, $R^2$ and/or $R^{12}$ are independently =C(R$^D$)$_2$. In some embodiments, $R^2$ and/or $R^{12}$ are independently =CH—R$^D$.

In some embodiments, when $R^2$ and/or $R^{12}$ is =CH—R$^D$, each group may independently have either configuration shown below:

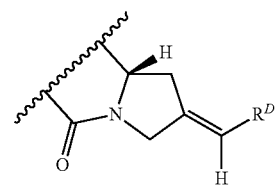

(I)

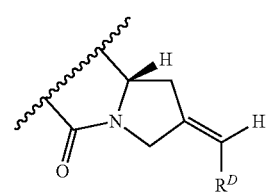

(II)

In some embodiments, a =CH—R$^D$ is in configuration (I).

In some embodiments, R" is a C$_3$ alkylene group or a C$_5$ alkylene group.

In some embodiments, an exemplary PBD dimer component of an ADC has the structure of Formula A(I):

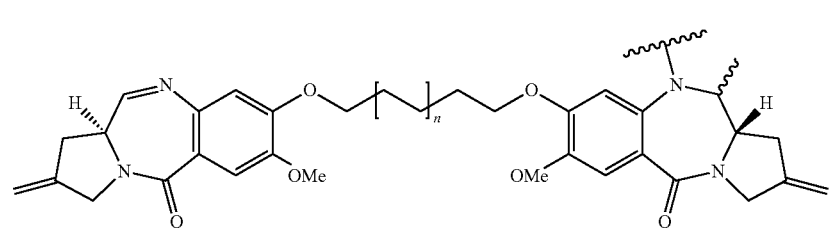

wherein n is 0 or 1.

In some embodiments, an exemplary PBD dimer component of an ADC has the structure of Formula A(II):

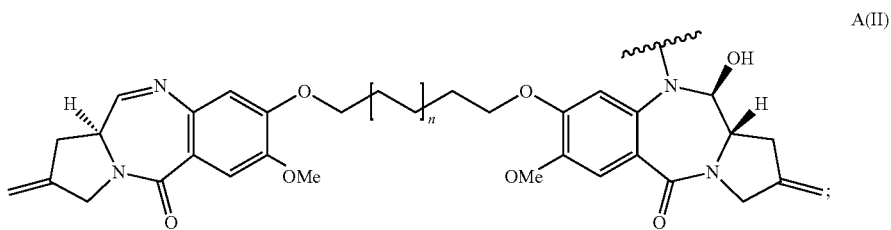

A(II)

wherein n is 0 or 1.

In some embodiments, an exemplary PBD dimer component of an ADC has the structure of Formula A(III):

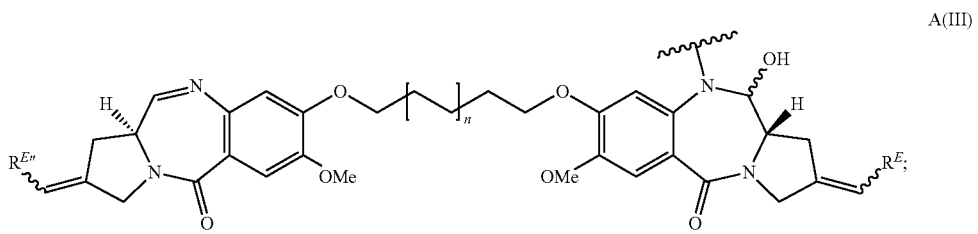

A(III)

wherein $R^E$ and $R^{E'}$ are each independently selected from H or $R^D$, wherein $R^D$ is defined as above; and
wherein n is 0 or 1.

In some embodiments, n is 0. In some embodiments, n is 1. In some embodiments, $R^E$ and/or $R^{E'}$ is H. In some embodiments, $R^E$ and $R^{E'}$ are H. In some embodiments, $R^E$ and/or $R^{E'}$ is $R^D$, wherein $R^D$ is optionally substituted $C_{1-12}$ alkyl. In some embodiments, $R^E$ and/or $R^{E'}$ is $R^D$, wherein $R^D$ is methyl.

In some embodiments, an exemplary PBD dimer component of an ADC has the structure of Formula A(IV):

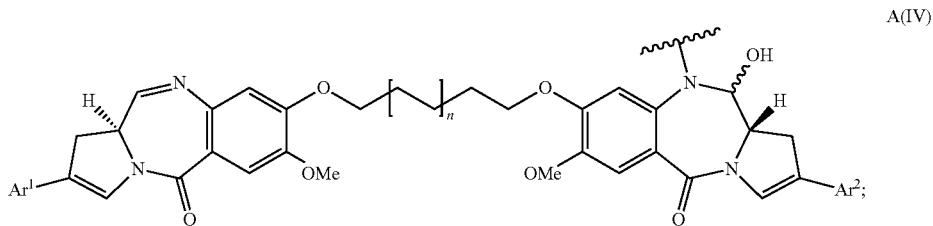

A(IV)

wherein $Ar^1$ and $Ar^2$ are each independently optionally substituted $C_{5-20}$ aryl; wherein $Ar^1$ and $Ar^2$ may be the same or different; and
wherein n is 0 or 1.

In some embodiments, an exemplary PBD dimer component of an ADC has the structure of Formula A(V):

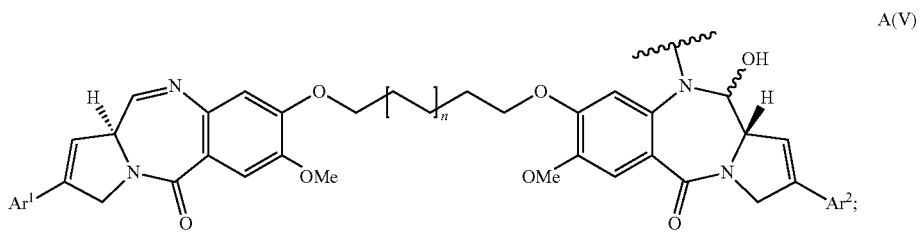

A(V)

wherein $Ar^1$ and $Ar^2$ are each independently optionally substituted $C_{5-20}$ aryl; wherein $Ar^1$ and $Ar^2$ may be the same or different; and wherein n is 0 or 1.

In some embodiments, $Ar^1$ and $Ar^2$ are each independently selected from optionally substituted phenyl, furanyl, thiophenyl and pyridyl. In some embodiments, $Ar^1$ and $Ar^2$ are each independently optionally substituted phenyl. In some embodiments, $Ar^1$ and $Ar^2$ are each independently optionally substituted thien-2-yl or thien-3-yl. In some embodiments, $Ar^1$ and $Ar^2$ are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

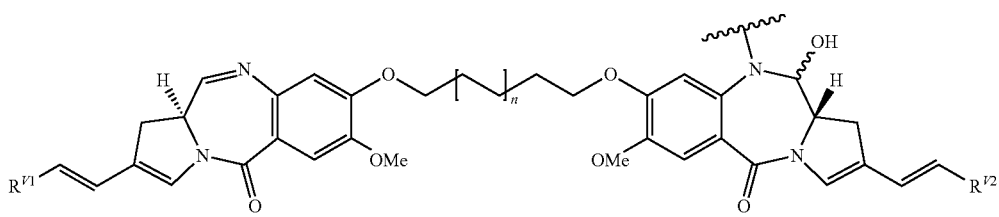

B and salts and solvates thereof, wherein:
the wavy line indicates the covalent attachment site to the linker;
the wavy line connected to the OH indicates the S or R configuration;
$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

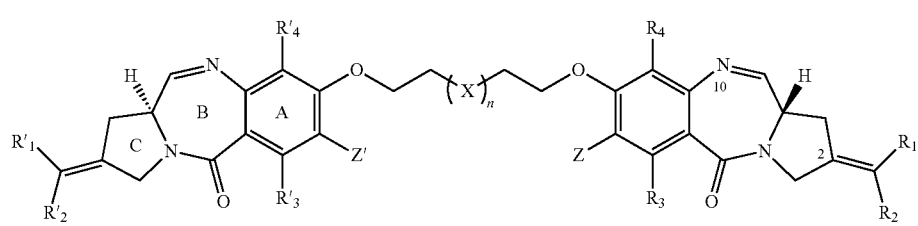

C(I)

-continued

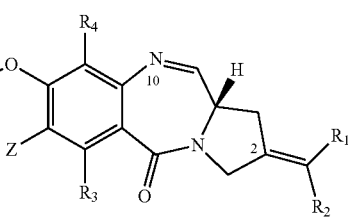

C(II)

Formulas C(I) and C(II) are shown in their N10-C11 imine form. Exemplary PBD drug moieties also include the carbinolamine and protected carbinolamine forms as well, as shown in the table below:

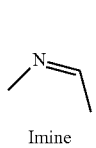
Imine

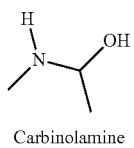
Carbinolamine

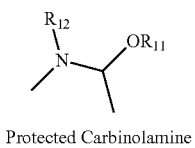
Protected Carbinolamine wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R'_1$, $R_2$ and $R'_2$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, $-NH_2$, $-NHMe$, $-OH$, and $-SH$, where, in some embodiments, alkyl, alkenyl and alkynyl chains comprise up to 5 carbon atoms;

$R_3$ and $R'_3$ are independently selected from H, OR, NHR, and $NR_2$, where R is a primary, secondary or tertiary alkyl chain containing 1 to 5 carbon atoms;

$R_4$ and $R'_4$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is H, $C_1$-$C_8$ alkyl, or a protecting group;

wherein a hydrogen of one of $R_1$, $R'_1$, $R_2$, $R'_2$, $R_5$, or $R_{12}$ or a hydrogen of the $-OCH_2CH_2(X)_nCH_2CH_2O-$ spacer between the A rings is replaced with a bond connected to the linker of the ADC.

Exemplary PDB dimer portions of ADC include, but are not limited to (the wavy line indicates the site of covalent attachment to the linker):

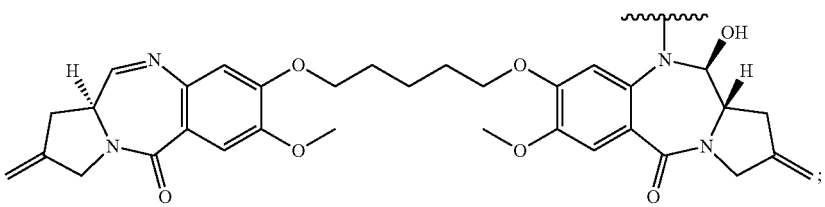
PBD dimer

A further non-limiting exemplary ADC comprising a PBD dimer may be made by conjugating a monomethyl disulfide N10-linked PBD (shown below) to an antibody:

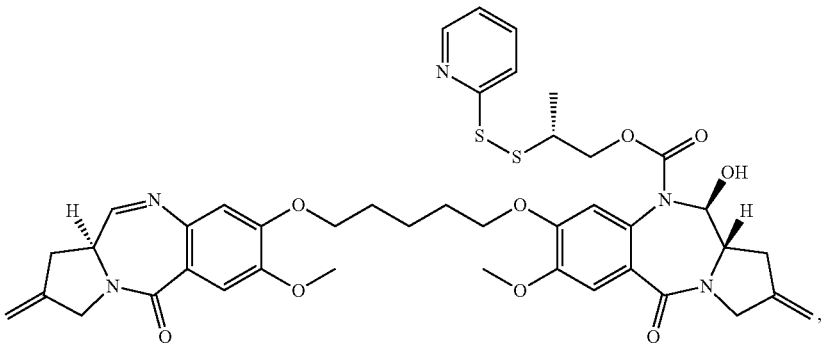

to produce a monomethyl disulfide N10-linked PBD antibody-drug conjugate:

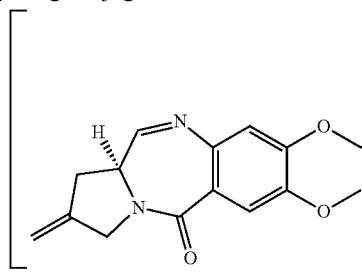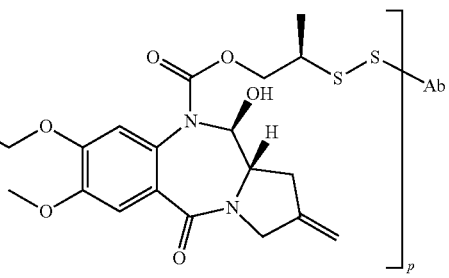

The linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598.

(5) Anthracyclines

In some embodiments, an ADC comprises an anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703;), including phase II/III trials for hepatocellular carcinoma (Sun et al (2003) *Proceedings of the American Society for Clinical Oncology* 22, Abs1448; Quintieri (2003) *Proceedings of the American Association of Cancer Research*, 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

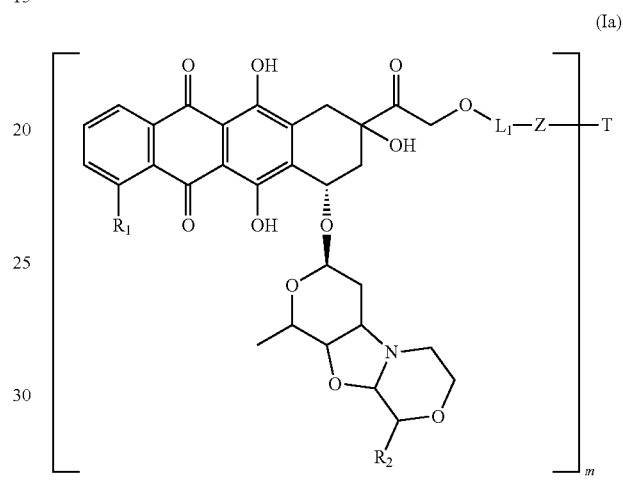

(Ia)

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

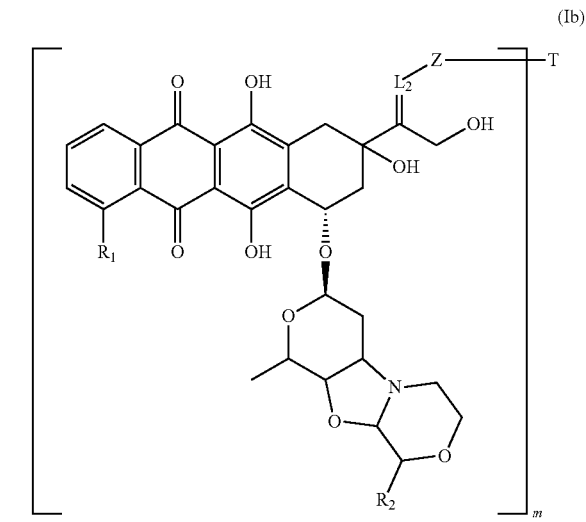

(Ib)

wherein R₁ is hydrogen atom, hydroxy or methoxy group and R₂ is a C₁-C₅ alkoxy group, or a pharmaceutically acceptable salt thereof;

L₂ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, R₁ and R₂ are both methoxy (—OMe).

In some embodiments, the nemorubicin component of a nemorubicin-containing ADC is PNU-159682. In some such embodiments, the drug portion of the ADC may have one of the following structures:

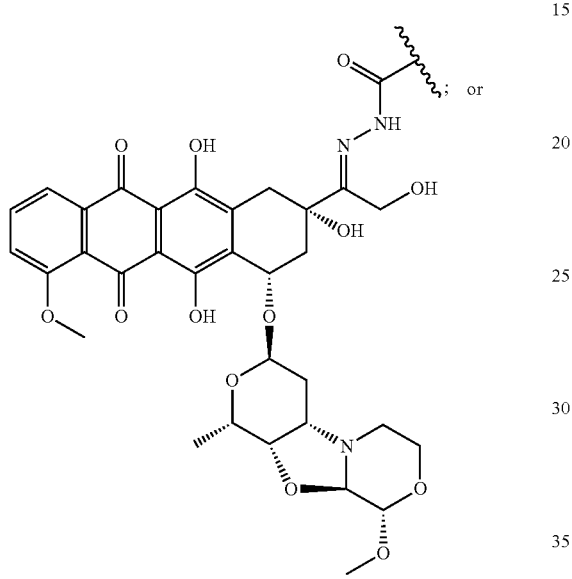

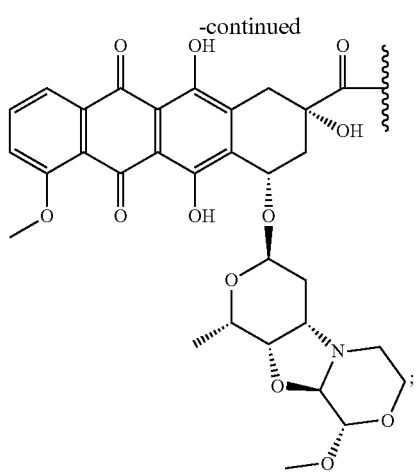

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

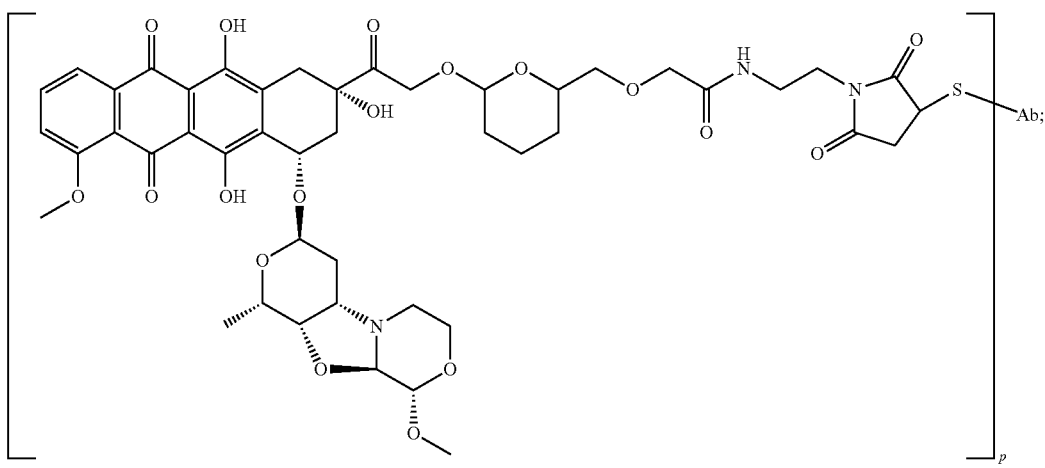

PNU-159682 maleimide acetal-Ab

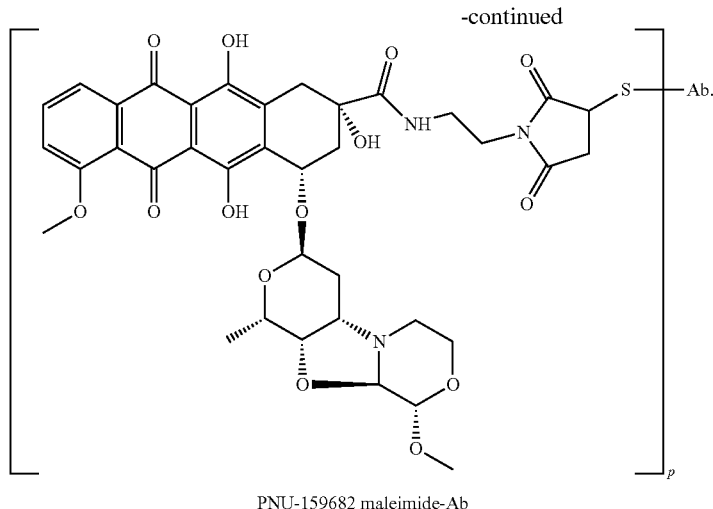

PNU-159682 maleimide-Ab

The linker of PNU-159682 maleimide acetal-Ab is acid-labile.

(6) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. In some embodiments, when an immunoconjugate is used for detection, it may comprise a radioactive atom for scintigraphic studies, for example $Tc^{99}$ or $I^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as $Tc^{99}$, $I^{123}$, $Re^{186}$, $Re^{188}$ and $In^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine-123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), which are useful for converting peptide-containing prodrugs into free drugs; D-alanyl-carboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Methods and Compositions for Diagnostics and Detection

In certain embodiments, any of the anti-GPC3 antibodies provided herein is useful for detecting the presence of GPC3 in a biological sample. The term "detecting" as used herein encompasses quantitative or qualitative detection. A "biological sample" comprises, e.g., a cell or tissue (e.g., biopsy material, including cancerous or potentially cancerous lymphoid tissue, such as lymphocytes, lymphoblasts, monocytes, myelomonocytes, and mixtures thereof).

In one embodiment, an anti-GPC3 antibody for use in a method of diagnosis or detection is provided. In a further aspect, a method of detecting the presence of GPC3 in a biological sample is provided. In certain embodiments, the method comprises contacting the biological sample with an anti-GPC3 antibody as described herein under conditions permissive for binding of the anti-GPC3 antibody to GPC3, and detecting whether a complex is formed between the anti-GPC3 antibody and GPC3 in the biological sample. Such method may be an in vitro or in vivo method. In one embodiment, an anti-GPC3 antibody is used to select subjects eligible for therapy with an anti-GPC3 antibody, e.g., where GPC3 is a biomarker for selection of patients. In a further embodiment, the biological sample is a cell or tissue.

In a further embodiment, an anti-GPC3 antibody is used in vivo to detect, e.g., by in vivo imaging, a GPC3-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting a GPC3-positive cancer in a subject, the method comprising administering a labeled anti-GPC3 antibody to a subject having or suspected of having a GPC3-positive cancer, and detecting the labeled anti-GPC3 antibody in the subject, wherein detection of the labeled anti-GPC3 antibody indicates a GPC3-positive cancer in the subject. In certain of such embodiments, the labeled anti-GPC3 antibody comprises an anti-GPC3 antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr.

In further embodiments, a method of diagnosis or detection comprises contacting a first anti-GPC3 antibody immobilized to a substrate with a biological sample to be tested for the presence of GPC3, exposing the substrate to a second anti-GPC3 antibody, and detecting whether the second anti-GPC3 is bound to a complex between the first anti-GPC3 antibody and GPC3 in the biological sample. A substrate may be any supportive medium, e.g., glass, metal, ceramic, polymeric beads, slides, chips, and other substrates. In certain embodiments, a biological sample comprises a cell or tissue. In certain embodiments, the first or second anti-GPC3 antibody is any of the antibodies described herein.

Exemplary disorders that may be diagnosed or detected according to any of the above embodiments include, but are not limited to, GPC3-positive cancers, such as GPC3-positive liver cancer, GPC3-positive hepatocellular carcinoma, GPC3-positive pancreatic cancer, GPC3-positive lung cancer, GPC3-positive colon cancer, GPC3-positive breast cancer, GPC3-positive prostate cancer, GPC3-positive leukemia, and GPC3-positive lymphoma. In some embodiments, a GPC-positive cancer is liver cancer. In some embodiments, a GPC-positive cancer is hepatocellular carcinoma. In some embodiments, a GPC3-positive cancer is a cancer that receives an anti-GPC3 immunohistochemistry (IHC) or in situ hybridization (ISH) score greater than "0," which corresponds to very weak or no staining in >90% of tumor cells. In another embodiment, a GPC3-positive cancer expresses GPC3 at a 1+, 2+ or 3+ level. In some embodiments, a GPC3-positive cancer is a cancer that expresses GPC3 according to a reverse-transcriptase PCR (RT-PCR) assay that detects GPC3 mRNA. In some embodiments, the RT-PCR is quantitative RT-PCR.

In certain embodiments, labeled anti-GPC3 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-GPC3 antibody or immunoconjugate as described herein are prepared by mixing such antibody or immunoconjugate having the desired degree of purity with one or more optional pharmaceutically acceptable carriers (*Remington's Pharmaceutical Sciences*

16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-GPC3 antibodies or immunoconjugates provided herein may be used in methods, e.g., therapeutic methods.

In one aspect, an anti-GPC3 antibody or immunoconjugate provided herein is used in a method of inhibiting proliferation of a GPC3-positive cell, the method comprising exposing the cell to the anti-GPC3 antibody or immunoconjugate under conditions permissive for binding of the anti-GPC3 antibody or immunoconjugate to GPC3 on the surface of the cell, thereby inhibiting the proliferation of the cell. In certain embodiments, the method is an in vitro or an in vivo method. In further embodiments, the cell is a lymphocyte, lymphoblast, monocyte, or myelomonocyte cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-GPC3 antibody or immunoconjugate for use as a medicament is provided. In further aspects, an anti-GPC3 antibody or immunoconjugate for use in a method of treatment is provided. In certain embodiments, an anti-GPC3 antibody or immunoconjugate for use in treating GPC3-positive cancer is provided. In certain embodiments, the invention provides an anti-GPC3 antibody or immunoconjugate for use in a method of treating an individual having a GPC3-positive cancer, the method comprising administering to the individual an effective amount of the anti-GPC3 antibody or immunoconjugate. In one such embodiment, the method further comprises administering to the individual an effective amount of at least one additional therapeutic agent, e.g., as described below.

In a further aspect, the invention provides for the use of an anti-GPC3 antibody or immunoconjugate in the manufacture or preparation of a medicament. In one embodiment, the medicament is for treatment of GPC3-positive cancer. In a further embodiment, the medicament is for use in a method of treating GPC3-positive cancer, the method comprising administering to an individual having GPC3-positive cancer an effective amount of the medicament. In one such embodiment, the method further comprises administering to the individual an effective amount of at least one additional therapeutic agent, e.g., as described below.

In a further aspect, the invention provides a method for treating GPC3-positive cancer. In one embodiment, the method comprises administering to an individual having such GPC3-positive cancer an effective amount of an anti-GPC3 antibody or immunoconjugate. In one such embodiment, the method further comprises administering to the individual an effective amount of at least one additional therapeutic agent, as described below.

A GPC3-positive cancer according to any of the above embodiments may be, e.g., GPC3-positive liver cancer, GPC3-positive hepatocellular carcinoma, GPC-positive pancreatic cancer, GPC-positive lung cancer, GPC-positive colon cancer, GPC-positive breast cancer, GPC-positive prostate cancer, GPC-positive leukemia, or GPC-positive lymphoma. In some embodiments, a GPC3-positive cancer is a cancer that receives an anti-GPC3 immunohistochemistry (IHC) or in situ hybridization (ISH) score greater than "0," which corresponds to very weak or no staining in >90% of tumor cells. In another embodiment, a GPC3-positive cancer expresses GPC3 at a 1+, 2+ or 3+ level. In some embodiments, a GPC3-positive cancer is a cancer that expresses GPC3 according to a reverse-transcriptase PCR (RT-PCR) assay that detects GPC3 mRNA. In some embodiments, the RT-PCR is quantitative RT-PCR.

An "individual" according to any of the above embodiments may be a human.

In a further aspect, the invention provides pharmaceutical formulations comprising any of the anti-GPC3 antibodies or immunoconjugate provided herein, e.g., for use in any of the above therapeutic methods. In one embodiment, a pharmaceutical formulation comprises any of the anti-GPC3 antibodies or immunoconjugates provided herein and a pharmaceutically acceptable carrier. In another embodiment, a pharmaceutical formulation comprises any of the anti-GPC3 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-GPC3 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

Example 1: Human GPC3 Expression

Human GPC3 gene expression was analyzed using a proprietary database containing gene expression information (GeneExpress®, Gene Logic Inc., Gaithersburg, Md.). Graphical analysis of the GeneExpress® database was conducted using a microarray profile viewer. FIG. 1 is a graphic representation of human GPC3 gene expression in various tissues. The scale on the y-axis indicates gene expression levels based on hybridization signal intensity. Dots appear both to the left and to the right of the line extending from the name of each listed tissue. The dots appearing to the left of the line represent gene expression in normal tissue, and the dots appearing to the right of the line represent gene expression in tumor and diseased tissue. FIG. 1 shows increased GPC3 gene expression in certain tumor or diseased tissues relative to their normal counterparts. For example, GPC3 is substantially overexpressed in liver tumor and diseased tissue.

Figure 2:
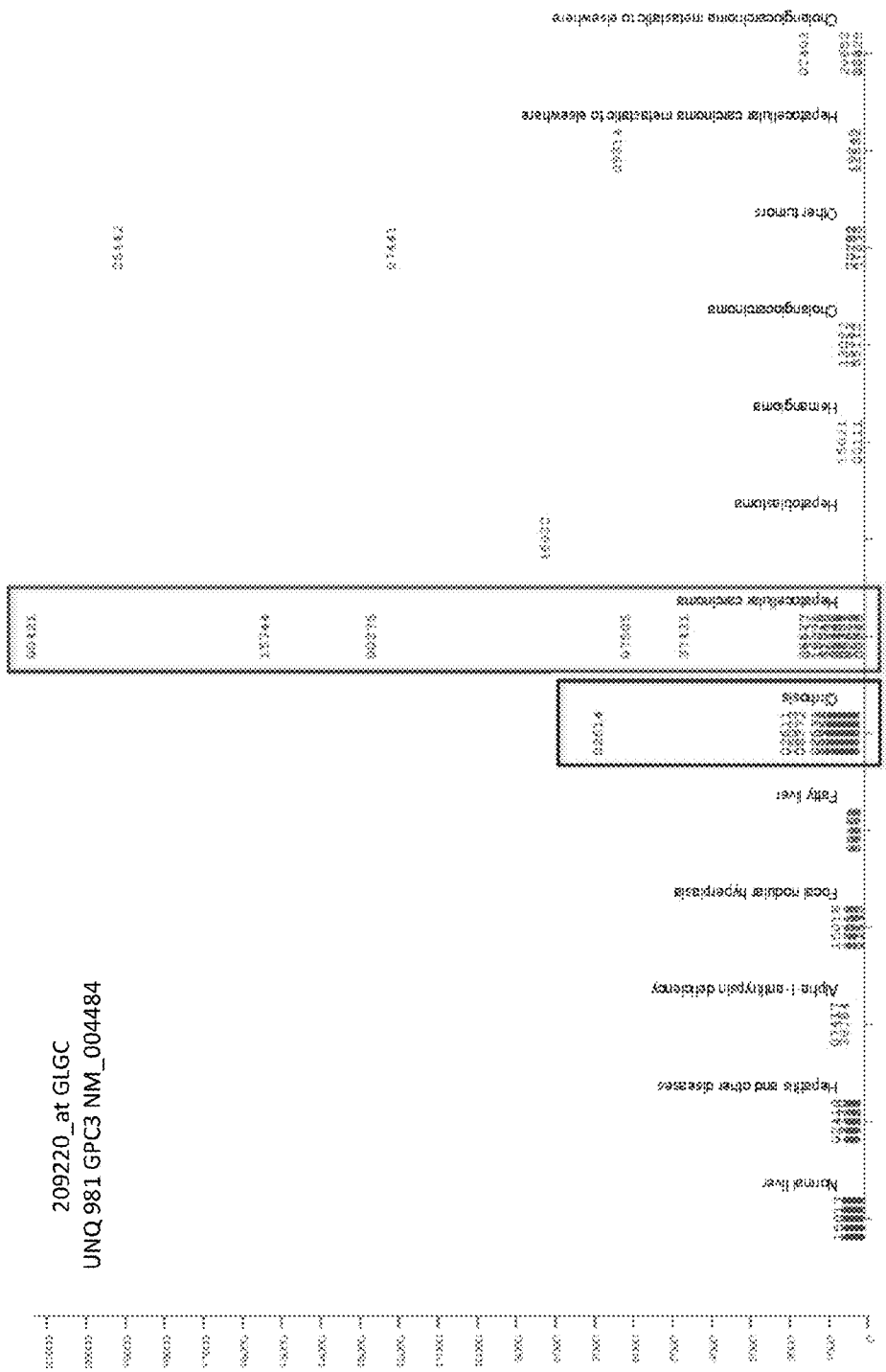
FIG. 2 shows expression of GPC3 in normal liver, liver cancers, and diseased liver, as described in Example 1.

FIG. 2 shows that GPC3 is substantially overexpressed in hepatocellular carcinoma, and somewhat overexpressed in cirrhosis. GPC3 is not overexpressed in normal liver nor in various other liver diseases.

Figure 3:
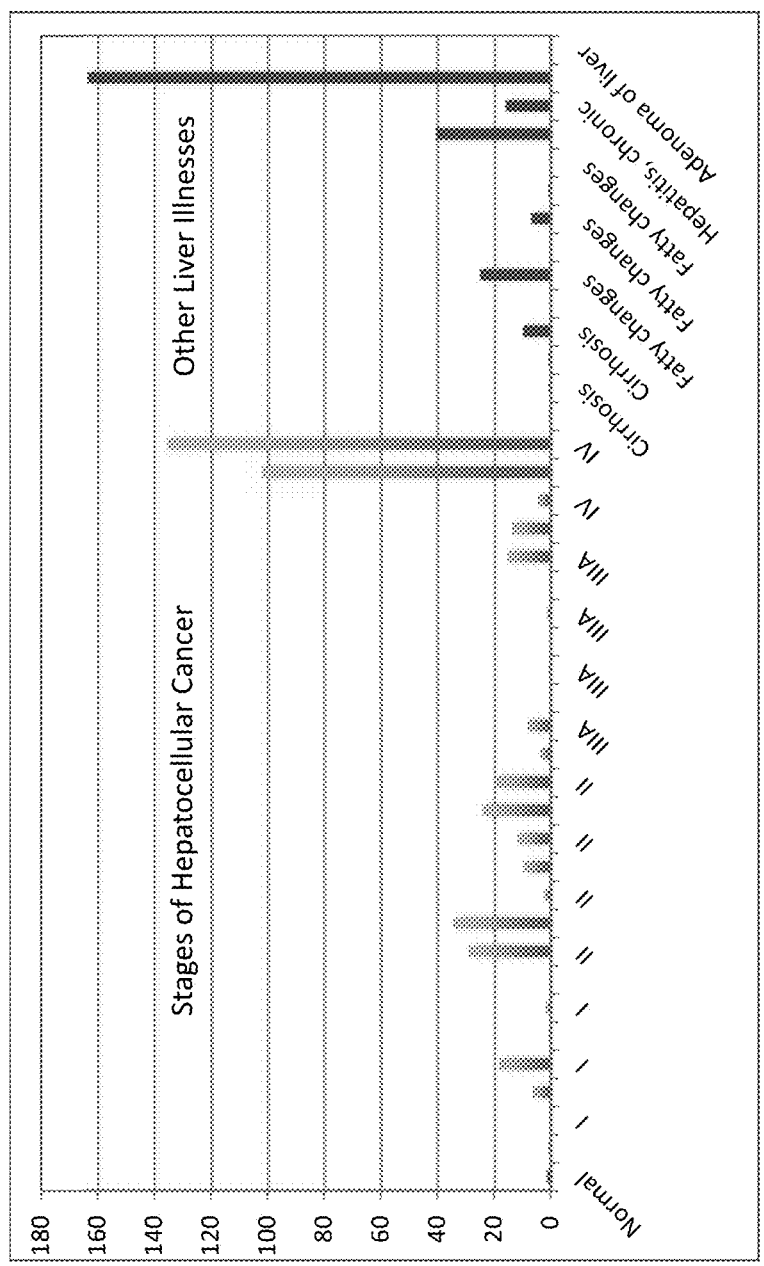
FIG. 3 shows expression of GPC3 in various stages of hepatocellular carcinoma and other liver diseases, as described in Example 1.

Expression of GPC3 was also determined by qPCR in cDNA samples from different stages of hepatocellular carcinoma, and in samples from other liver diseases, including cirrhosis, fatty changes, hepatitis, chronic hepatitis, and adenoma of the liver (OriGene, Rockville, Md.). GPC3 expression was normalized to RPL19. As shown in FIG. 3, GPC3 was highly expressed in stage IV hepatocellular carcinoma samples. GPC3 was also highly expressed in one chronic hepatitis sample. No significant GPC3 expression was detected using this assay in a variety of normal human tissues, including adrenal gland, brain, cervix, colon, epididymis, esophagus, fat, heart, small intestine, intracranial artery, kidney, liver, lung, lymph node, lymphocytes, mammary gland, muscle, nasal mucosa, optic nerve, ovary, oviduct, pancreas, pericardium, pituitary, placenta, prostate, rectum, retina, seminal vesicles, skin, spinal cord, spleen, stomach, testis, thymus, thyroid, tongue, tonsil, trachea, ureter, urinary bladder, uterus, uvula, vagina, and vena cava.

Example 2: Monoclonal Antibody Generation

A. GPC3 Extracellular Domain Immunization and Antibody Characterization

Monoclonal antibodies against human (hu) GPC3 were generated using the following procedures by immunizing five Balb/c mice with recombinant huGPC3 extracellular domain (ECD, amino acids of 1-547) fused to a C-terminal Flag (RADYKDDDDK) expressed in a mammalian expression system.

Positive clones were expanded and re-screened for binding to huGPC3, cynoGPC3, and HepG2 cells by ELISA, FACS, and immunohistochemistry (IHC). Thirteen antibodies were selected and purified, including antibodies 7H1 and 4G7. The heavy and light chain variable region sequences of antibody 7H1 are shown in SEQ ID NOs: 2 and 3, respectively. The heavy and light chain variable region sequences of antibody 4G7 are shown in SEQ ID NOs: 26 and 27, respectively. See FIG. 4A-B.

Figure 5:
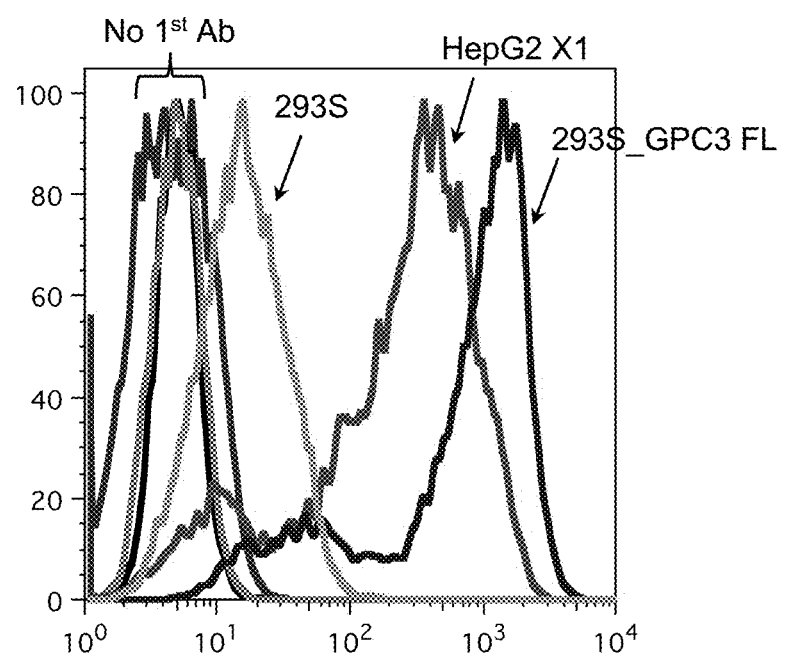
FIG. 5 shows binding of antibody 7H1 to 293S cells, HepG2 X1 cells, and 293S cells expressing GPC3 (293S_GPC3 FL), measured by FACS, as described in Example 2.

Antibody 7H1 was found to react strongly with hepatic cancer tissue microarray, JHH cells, HepG2 cells, and cells stably transfected with GPC3 by IHC, and antibodies 7H1 and 4G7 both react strongly with HepG2 X1 cells and 293S cells expressing GPC3 by FACS. FIG. 5 shows exemplary FACS data for antibody 7H1. Antibody 7H1 also detects human, cynomolgus monkey, rat, and mouse GPC3 by Western blot.

Epitope binning of anti-GPC3 antibodies was performed using a competition assay. Using the Octet RED384 instrument (ForteBio), biotinylated GPC3 was captured onto Streptavidin biosensors at 10 μg/ml for 600 seconds. Binding of the first antibody to saturation was achieved by adding 10 μg/ml for 600 seconds. The same biosensors were dipped into the competing antibodies at 5 μg/ml and binding was measured for 600 seconds. The failure of the second antibody to bind in the presence of saturating quantities of the first antibody indicates the two antibodies were in the same epitope bin; the success of the second antibody to bind in the presence of the saturating quantities of the first antibody indicates the two antibodies were in different epitope bins. Antibody 7H1 was used as the first saturating antibody. A subsequent experiment was performed using antibody 4G7 as the first saturating antibody. Antibodies 7H1 and 4G7 were found to be in different epitope bins.

Figure 6:
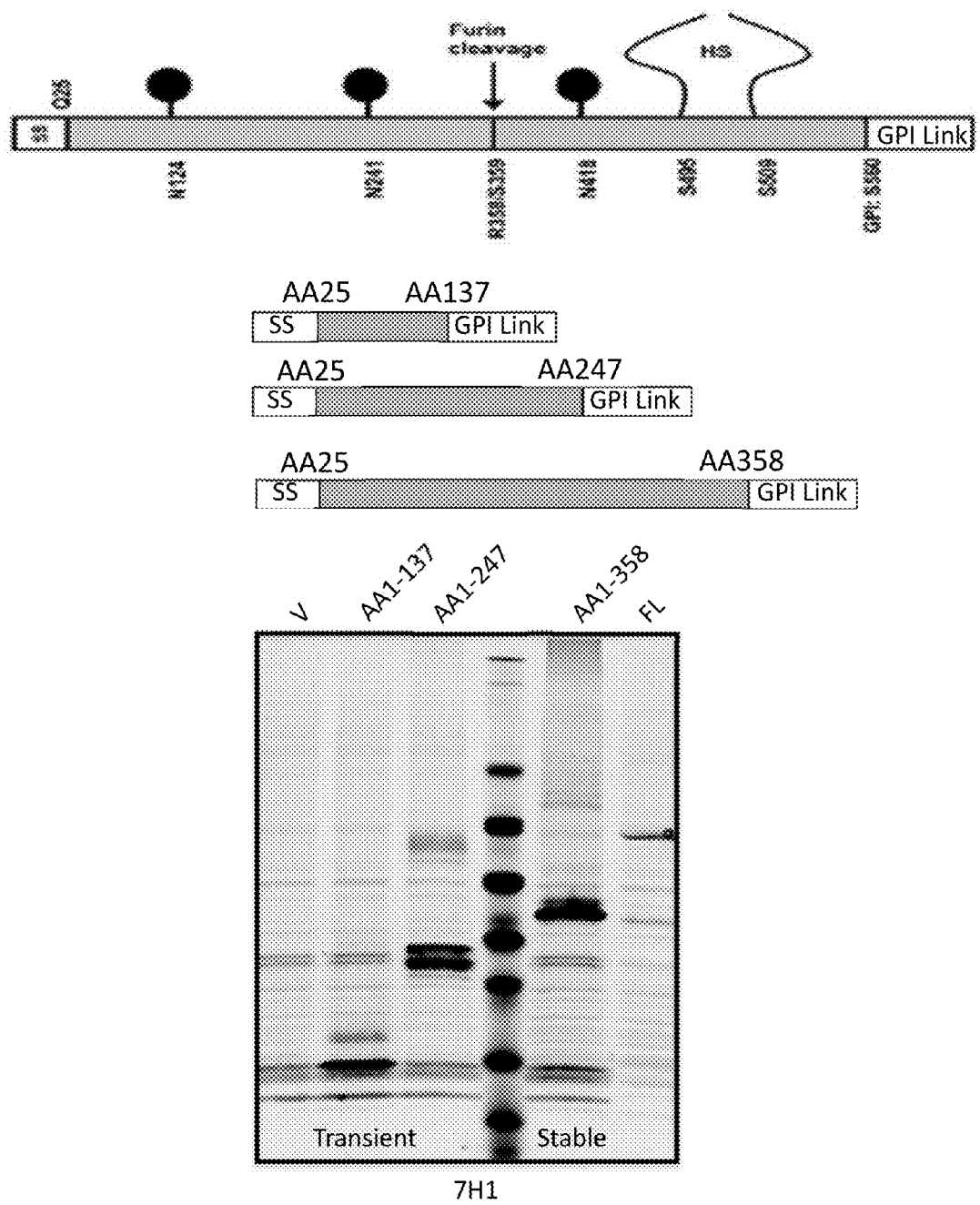
FIG. 6 shows a schematic diagram of certain features of human GPC3 protein sequence, three fragments of human GPC3, and a Western blot showing binding of antibody 7H1 to the GPC3 fragments, as described in Example 2.
Figure 7:
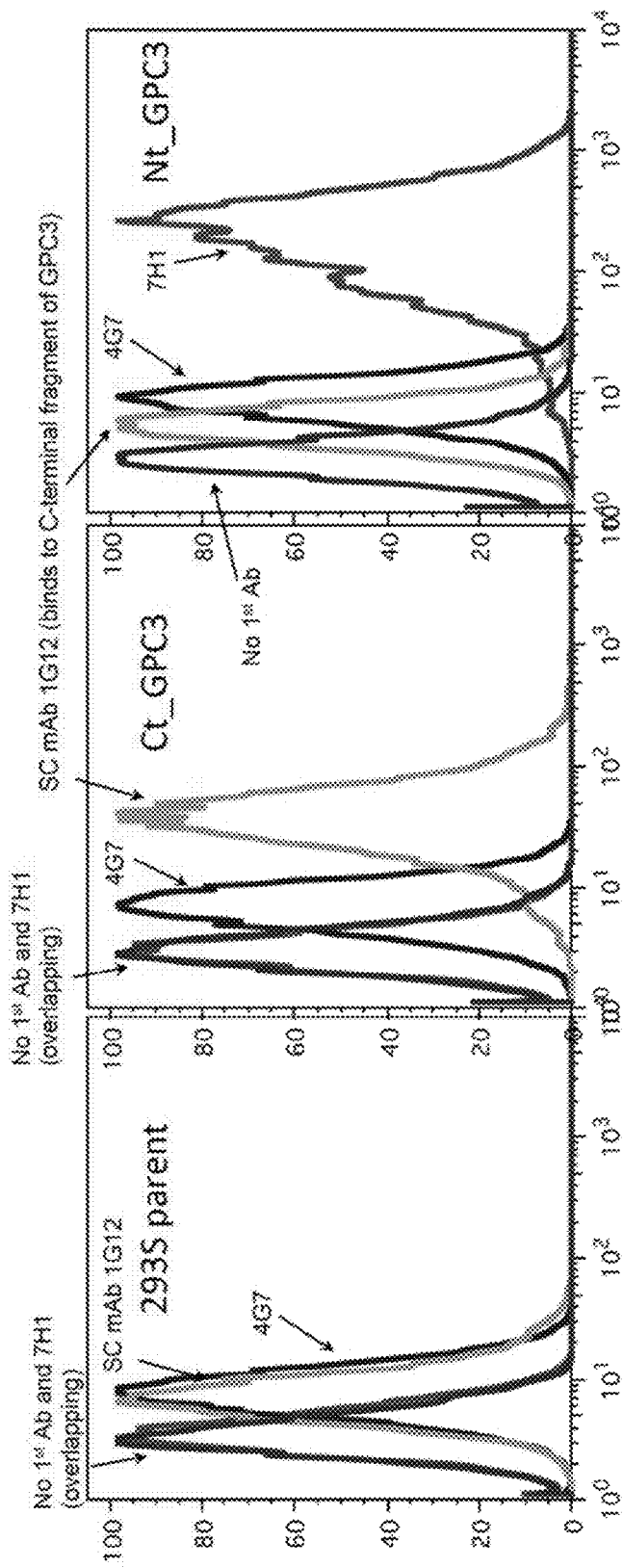
FIG. 7 shows binding of antibodies 7H1 and 4G7, as well as a control antibody 1G12 (Santa Cruz Biotechnology) to 293S cells, 293S cells expressing a C-terminal fragment of GPC3 (Ct_GPC3) and 293S cells expressing an N-terminal fragment of GPC3 (Nt_GPC3), measured by FACS, as described in Example 2.

C-terminal truncation constructs of human GPC3 were made to further refine the epitopes for antibodies 7H1 and 4G7. Three different C-terminal truncations were made, comprising amino acids 25 to 137 of human GPC3, amino acids 25 to 247 of human GPC3, and amino acids 25 to 358 of human GPC3. The three C-terminal truncations each comprised the GPC N-terminal signal sequence (SS) and C-terminal glycophosphatidylinositol anchor (GPI link). See FIG. 6. Antibody 7H1 was found to bind to all three constructs transiently expressed on the surface of 293S cells by FACS, and also to all three constructs by Western blot. See FIG. 6. Antibody 4G7 did not show significant binding to either N-terminal (amino acids 25-358) or C-terminal (amino acids 359-560) fragments of human GPC3 by FACS, suggesting that the epitope for 4G7 may span the furin cleavage site at amino acids R358/S359 of human GPC3. See FIG. 7 (Santa Cruz Biotechnology antibody 1G12, which was raised to amino acids 511-580 of human GPC3, was used as a positive control for C-terminal fragment binding). Antibody 7H1 was reformatted as a chimeric antibody with human A118C cysteine-engineered IgG1 and Igκ constant regions (SEQ ID NOs: 42 and 43).

B. GPC3 Truncated Extracellular Domain Immunization and Antibody Characterization Monoclonal antibodies against a C-terminal portion of the extracellular domain of human GPC3 were generated by immunizing five Balb/c mice with DNA encoding huGPC3 amino acids 359 to 560 with the GPC N-terminal signal sequence (SS) and C-terminal glycophosphatidylinositol anchor (GPI link). Mice were immunized with 50 μg of DNA and 2.5 μg of mouse GM-CSF via hydrodynamic tail vein (HTV) injection once per week for 7 weeks. Sera were screened by FACS for binding to 293 cells expressing the same huGPC(aa359-560) construct used for immunization. Following fusion, ten hybridomas expressed antibodies that bound human GPC3 extracellular domain (amino acids 1 to 560) by ELISA, and hybridomas expressed antibodies that bound huGPC(aa359-560) expressed on 293 cells by FACS. Three antibodies were cloned with human IgG1 A118C cysteine engineered heavy chain and Igκ light chain constant regions, including antibodies 4A11 and 15G1. The heavy and light chain variable region sequences of antibody 4A11 are shown in SEQ ID NOs: 10 and 11, respectively. The heavy and light chain variable region sequences of antibody 15G1 are shown in SEQ ID NOs: 18 and 19, respectively. See FIG. 4A-B.

Figure 8:
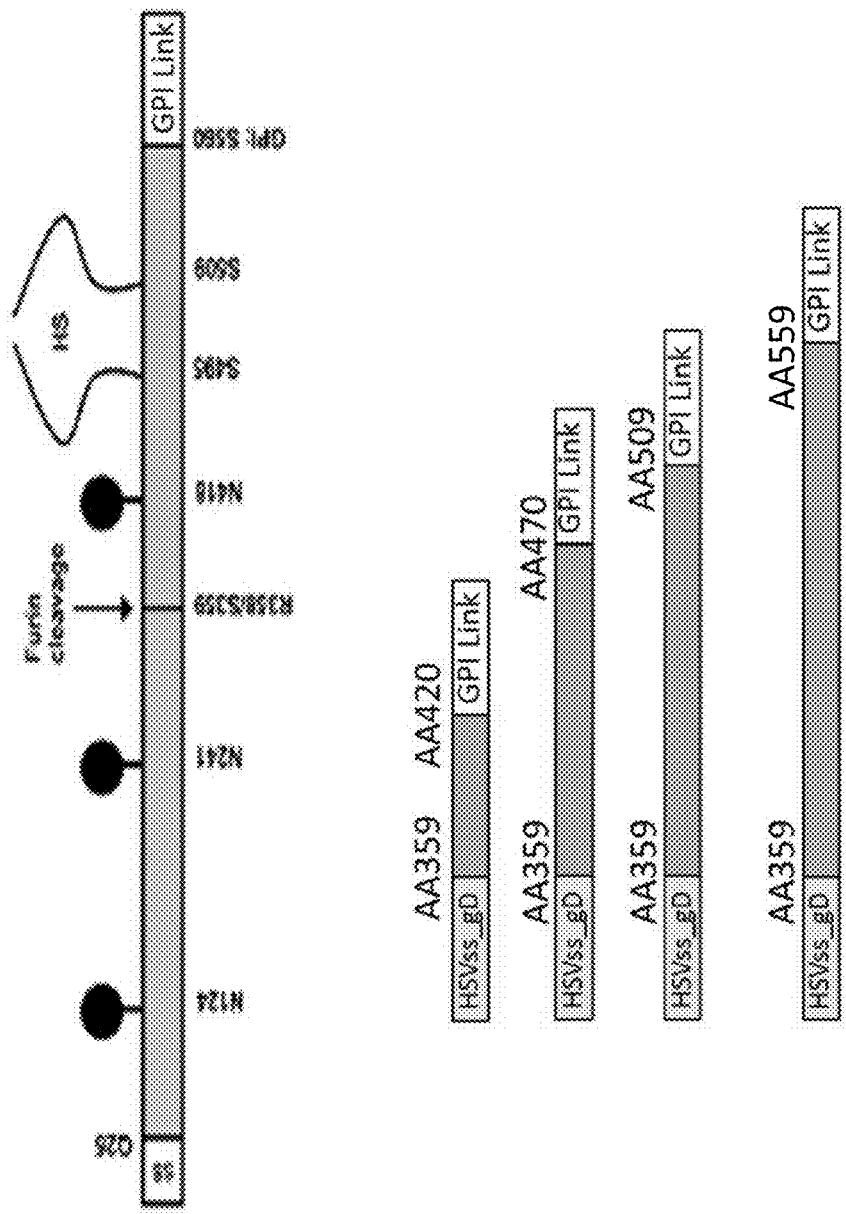
FIG. 8 shows a schematic diagram of certain features of human GPC3 protein sequence and four fragments of human GPC3, as described in Example 2.
Figure 9:
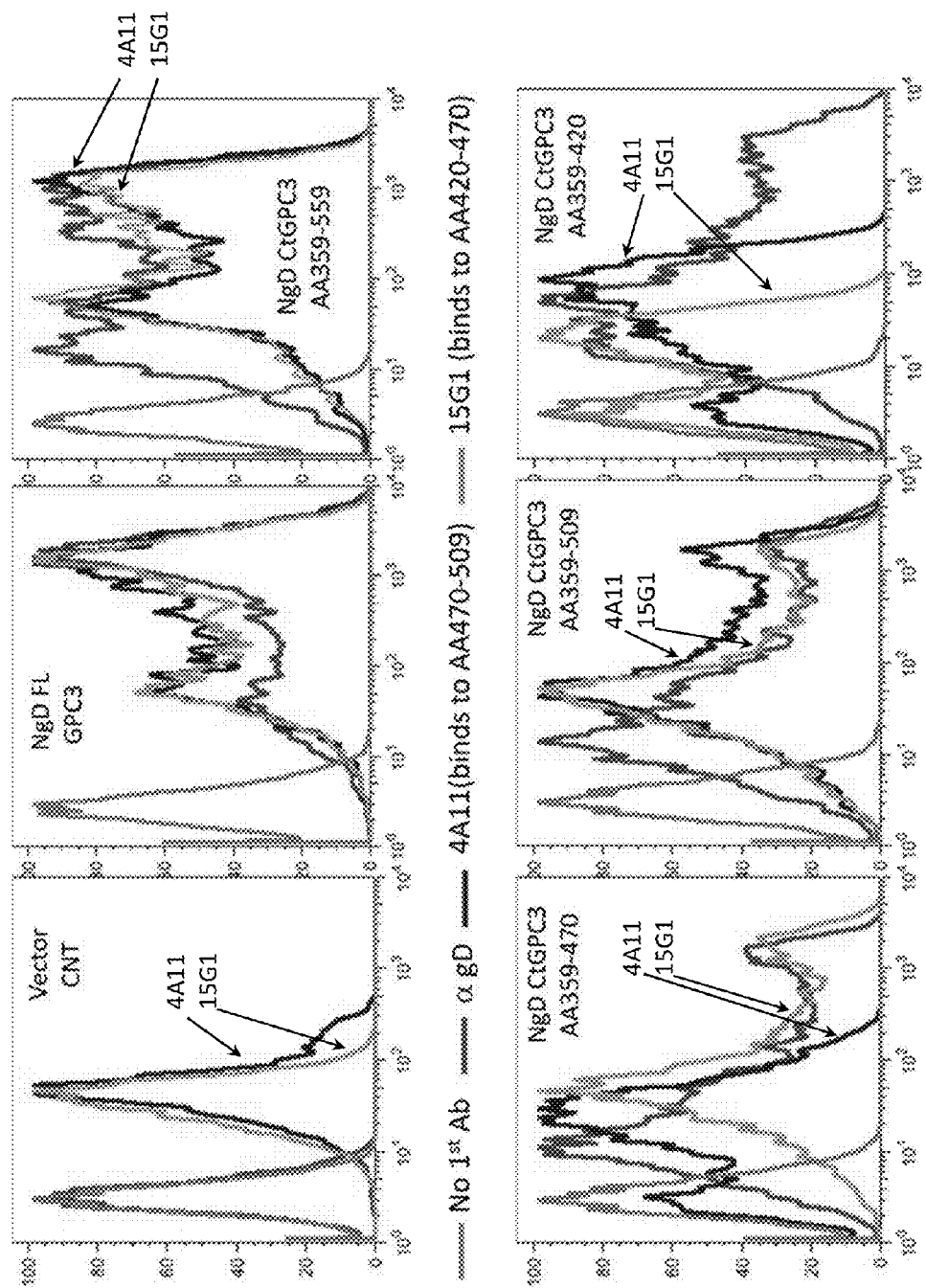
FIG. 9 shows binding of antibodies 4A11 and 15G1 to full-length FPC3 and three of the fragments in FIG. 8 expressed in 293S cells, measured by FACS, as described in Example 2.

C-terminal truncation constructs of huGPC(aa359-589) were made to further refine the epitopes for antibodies 4A11 and 15G1. Three different N-terminal truncations were made, comprising amino acids 359 to 420 of human GPC3, amino acids 359 to 470 of human GPC3, and amino acids 359 to 509 of human GPC3. The three C-terminal truncations each comprised an HSV N-terminal signal sequence (SS) and gD sequence (SEQ ID NO: 41) and C-terminal glycophosphatidylinositol anchor (GPI link). See FIG. 8. The huGPC truncation constructs were expressed on the surface of 293 cells and antibody binding was determined by FACS. An anti-gD was used as a positive control. Vector-transfected 293 cells were used as a negative control. Antibody 4A11 bound to huGPC(aa359-559) and huGPC (aa359-509), but not to huGPC(aa359-470) or huGPC (aa359-420), indicating that it binds to an epitope within amino acids 470 to 509 of human GPC. See FIG. 9. Antibody 15G1 bound to huGPC(aa359-559), huGPC (aa359-509), and huGPC(aa359-470), but not to huGPC (aa359-420), indicating that it binds to an epitope within amino acids 420 to 470 of human GPC. See FIG. 9.

Figure 10:
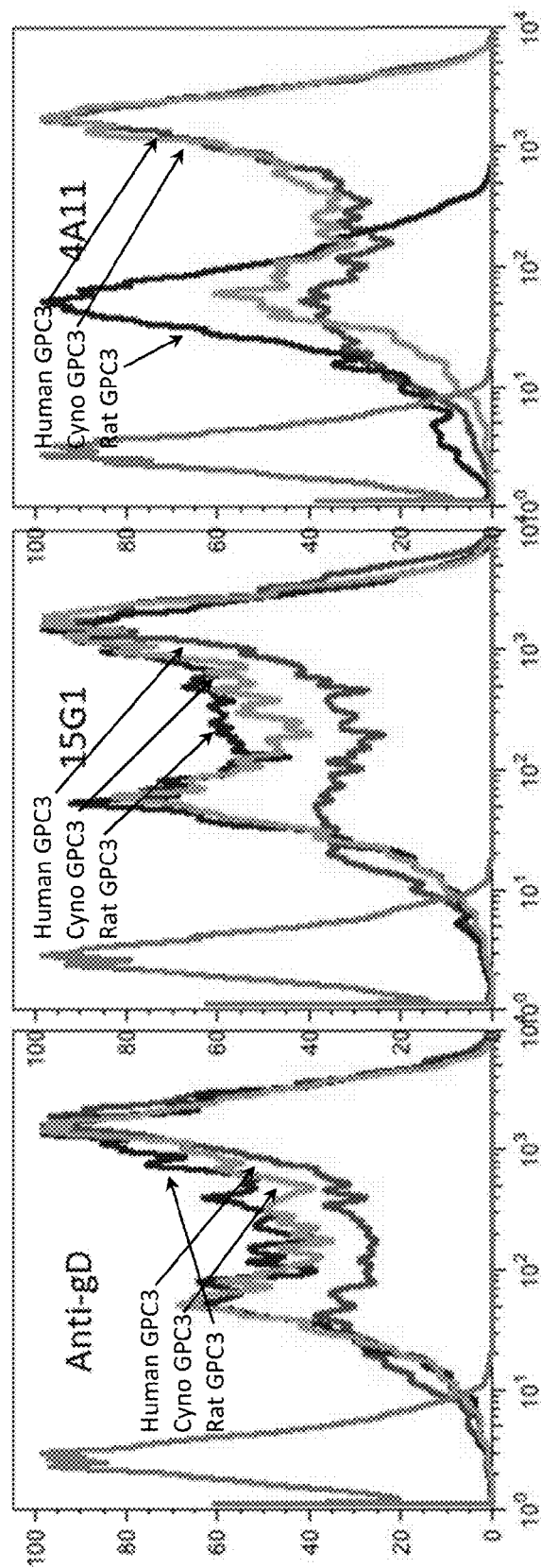
FIG. 10 shows binding of antibodies 15G1 and 4A11 to GPC3 from various species, as described in Example 2.

Antibodies 15G1 and 4A11 were tested for binding to full-length N-terminal gD-tagged cynomolgus monkey GPC3 and full-length N-terminal gD-tagged rat GPC3 expressed on the surface of 293 cells by FACS. Both antibodies bound to cynomolgus monkey GPC3. 15G1, but not 4A11, also bound to rat GPC3. See FIG. 10. As shown in FIG. 11, the 15G1 epitope is highly conserved between human, cynomolgus monkey, rhesus macaque, mouse, and rat GPC3, while the 4A11 epitope contains some sequence variations, particularly between primate and rodent GPC3. The 7H1 epitope is also highly conserved between human, cynomolgus monkey, rhesus macaque, mouse, and rat GPC3, and as discussed above, antibody 7H1 detects human, cynomolgus monkey, rat, and mouse GPC3 by Western blot.

Example 3: Internalization of Monoclonal Antibodies

Antibodies 7H1, 4G7, 15G1, and 4A11 were assayed for internalization in Hep3B.2.1-7, HepG2, and JHH7 cells. Antibody internalization was measured at 2 hours and at 20 hours at 37° C. Cells were incubated with antibody at 4 µg/ml for 2 or 20 hours at 37° C., or at 4° C. for one hour. Cells were then washed with PBS, fixed with 4% paraformaldehyde, and permeabilized with 0.05% saponin for 5 minutes at 37° C. Cells were then incubated with anti-LAMPI antibody (Sigma Aldrich) as a lysosome marker for one hour at room temperature, washed, then incubated with anti-human-Cy3 and anti-rabbit-Alexa 488 for one hour at room temperature. The cells were washed and then mounted with mounting media. Staining was visually quantitated based on intensity.

Very little internalization of the antibodies was observed at the 2 hour time point. The extent of internalization of the antibodies into lysosomes at the 20 hour time point in each cell line is summarized in Table 2.

TABLE 2

| Antibody internalization into lysosomes | | | | |
|---|---|---|---|---|
| Cell line | 7H1 | 4A11 | 15G1 | 4G7 |
| HepG2 | +/− | + | + | ++++ |
| JHH7 | + | +++ | +++ | +/− |
| Hep3B.2.1-7 | − | − | − | − |

At 20 hours, the N-terminal binding antibody 7H1 showed different internalization characteristics than C-terminal binding antibodies 4A11 and 15G1. Antibody 4G7, which is predicted bind to an epitope spanning the furin cleavage site at amino acids R358/S359, showed different internalization characteristics from the other antibodies.

Example 4: Sensitivities of GPC3-Expressing Cell Lines to Free Nemorubicin Derivative and Free Pyrrolobenzodiazepine Various GPC3-expressing cell lines were tested for sensitivity to free nemorubicin derivative, PNU-159682, which has the structure:

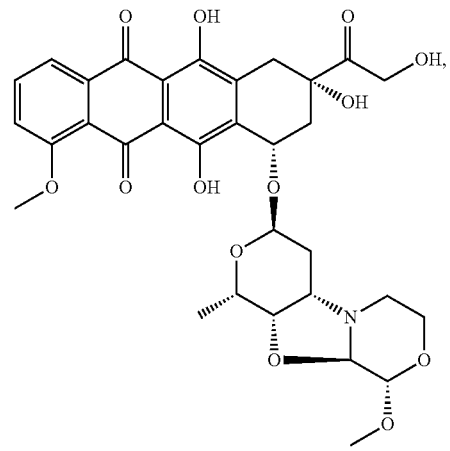 [SMILES: COc1cccc2c1C(=O)c1c(O)c3c(c(O)c1C2=O)C[C@@](O)(C(=O)CO)C[C@@H]3O[C@H]1C[C@H]2[C@H](O[C@@H]3[C@@H](OC)OCCN32)[C@H](C)O1]

or a free pyrrolobenzodiazepine, SG-2057, which has the structure:

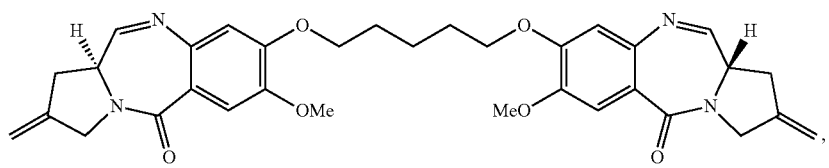

as follows. Proliferation in the presence of PNU-159682 or SG-2057 were assessed using cells plated at 1000 cells per well in 50 μl of normal growth medium in 96-well clear-bottom plates (PerkinElmer Life Sciences). Twenty-four hours later, an additional 50 μl of culture medium with serial dilutions of the drug was added to triplicate wells. Three or 5 days later, cell numbers were determined using CellTiter-GloII (Promega Corp.) and with an EnVision 2101 multilabel reader (PerkinElmer). The results of that experiment are summarized in Table 3.

TABLE 3

Cell line sensitivity to PNU-159682 and SG-2057

| Cell line | PNU-159682 EC50 | SG-2057 EC50 |
|---|---|---|
| 293S | 22 pM | 56 pM |
| 293_GPC3 | 19 pM | 34 pM |
| PC3 | 51 pM | 122 pM |
| Hep3B.2.1-7 | 42 pM | 474 pM |
| Huh7 | 29 pM | 147 pM |
| HepG2 | 29 pM | 29 pM |
| JHH7 | 38 pM | 135 pM |
| JHH5 | 31 pM | 105 pM |

As shown in Table 3, all of the cell lines tested are sensitive to both drugs.

Example 5: Production of Anti-GPC3 Antibody Drug Conjugates

For larger scale antibody production, antibodies were produced in CHO cells. Vectors coding for VL and VH were transfected into CHO cells and IgG was purified from cell culture media by protein A affinity chromatography.

Anti-GPC3 antibody-drug conjugates (ADCs) were produced by conjugating chimeric 7H1, 4A11, or 15G1 (human IgG1/kappa) with a heavy chain A118C mutation (7H1 thio-HC A118C, 4A11 thio-HC A118C, 15G1 thio-HC A118C) to the drug-linker moiety maleimide acetal PNU-159682 (see FIG. 12A) or monomethyl disulfide N10-linked PBD (see FIG. 12B). As initially isolated, the engineered cysteine residues in the antibodies exist as mixed disulfides with cellular thiols (e.g., glutathione) and are thus unavailable for conjugation. Partial reduction of these antibodies (e.g., with DTT), purification, and reoxidation with dehydroascorbic acid (DHAA) gives antibodies with free cysteine sulfhydryl groups available for conjugation, as previously described, e.g., in Junutula et al. (2008) Nat. Biotechnol. 26:925-932 and US 2011/0301334. Briefly, the antibodies were combined with the drug-linker moiety to allow conjugation of the drug-linker moiety to the free cysteine residues of the antibody. After several hours, the ADCs were purified. The drug load (average number of drug moieties per antibody) for each ADC was determined and was between 1.4-1.8 for the PBD conjugates and 1.4-1.8 for the PNU conjugates.

Example 6: Efficacy of Anti-GPC3 Antibody Drug Conjugates in HepG2 X1 Cell Line Xenograft Model The efficacy of the anti-GPC3 ADCs was investigated using a human HepG2 X1 xenograft model. Female C.B-17 SCID mice (Charles River Laboratories; Hollister, Calif.) were each inoculated subcutaneously in the flank area with ten million cells of HepG2 X1. When the xenograft tumors reached an average tumor volume of 100-300 mm$^3$ (referred to as Day 0), animals were randomized into groups of 7-10 mice each and received a single intravenous injection of the ADCs at the dose indicated in FIG. 13. Tumors and body weights of mice were measured 1-2 times a week throughout the study. Mice were promptly euthanized when body weight loss was >20% of their starting weight. All animals were euthanized before tumors reached 3000 mm$^3$ or showed signs of impending ulceration. The presence of the antibodies was confirmed by PK bleeds at 1, 7 and 14 days post injection. Expression of GPC3 on the surface of the HepG2 X1 cells and a HepG2 X1 tumor isolated from a xenograft mouse was confirmed by FACS, using antibodies 4G7, 7H1, and 4A11. See FIG. 13A-B.

Figure 14:
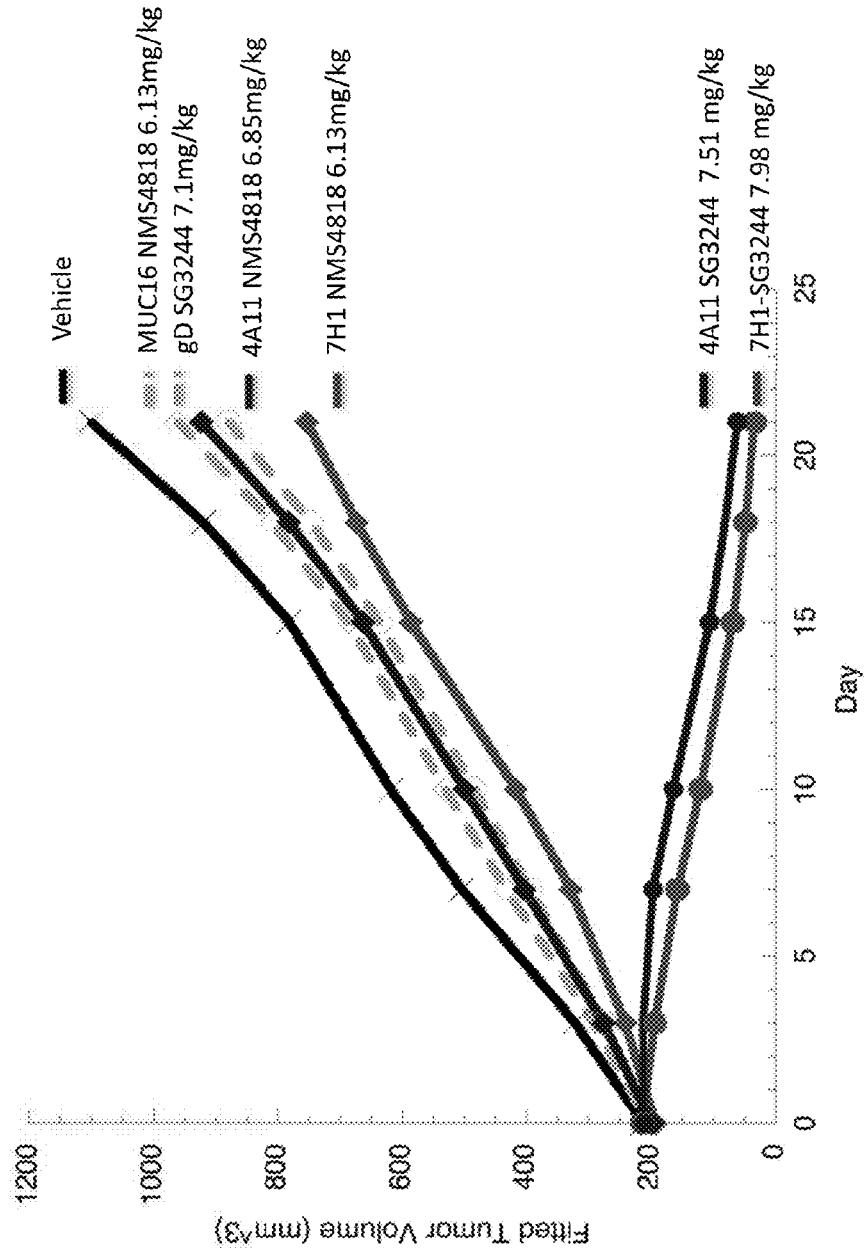
FIG. 14 shows change in tumor volume (mm$^3$) over time in a HepG2 X1 xenograft model upon treatment with various antibody-drug conjugates, as described in Example 6.

As shown in FIG. 14, substantial tumor growth inhibition was achieved with both 7H1-disulfide-PBD (7.98 mg/kg) and 4A11 disulfide-PBD (7.51 mg/kg). The PNU conjugates (7H1-acetal-PNU and 4A11-acetal-PNU) were less efficacious in this experiment.

Figure 15A:
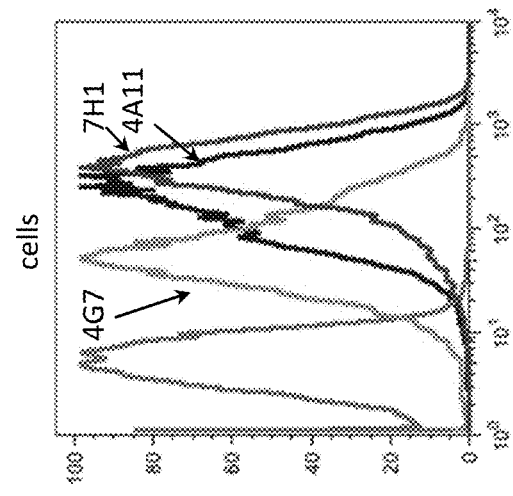
FIG. 15A-B show expression of GPC3 on the surface of (A) JHH7 cells and (B) isolated JHH7 X1 xenograft tumor cells, detecting using antibodies 4G7, 7H1, and 4A11 by FACS, as described in Example 7.
Figure 15B:
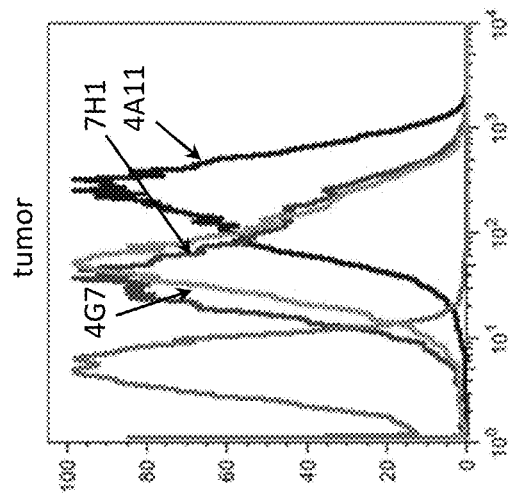

Example 7: Efficacy of Anti-GPC3 Antibody Drug Conjugates in JHH7 Cell Line Xenograft Model The efficacy of the anti-GPC3 ADCs was investigated using a human JHH7 xenograft model. Female NCR.nude mice (Taconic; Cambridge City, Ind.) were each inoculated subcutaneously in the flank area with three million cells of JHH7. When the xenograft tumors reached an average tumor volume of 100-300 mm$^3$ (referred to as Day 0), animals were randomized into groups of 7-10 mice each and received a single intravenous injection of the ADCs at the dose indicated in FIG. 13. Tumors and body weights of mice were measured 1-2 times a week throughout the study. Mice were promptly euthanized when body weight loss was >20% of their starting weight. All animals were euthanized before tumors reached 3000 mm$^3$ or showed signs of impending ulceration. The presence of the antibodies was confirmed by PK bleeds at 1, 4 and 14 days post injection. Expression of GPC3 on the surface of the JHH7 cells and a JHH7 tumor isolated from a xenograft mouse was confirmed by FACS, using antibodies 4G7, 7H1, and 4A11. See FIG. 15A-B.

Figure 16:
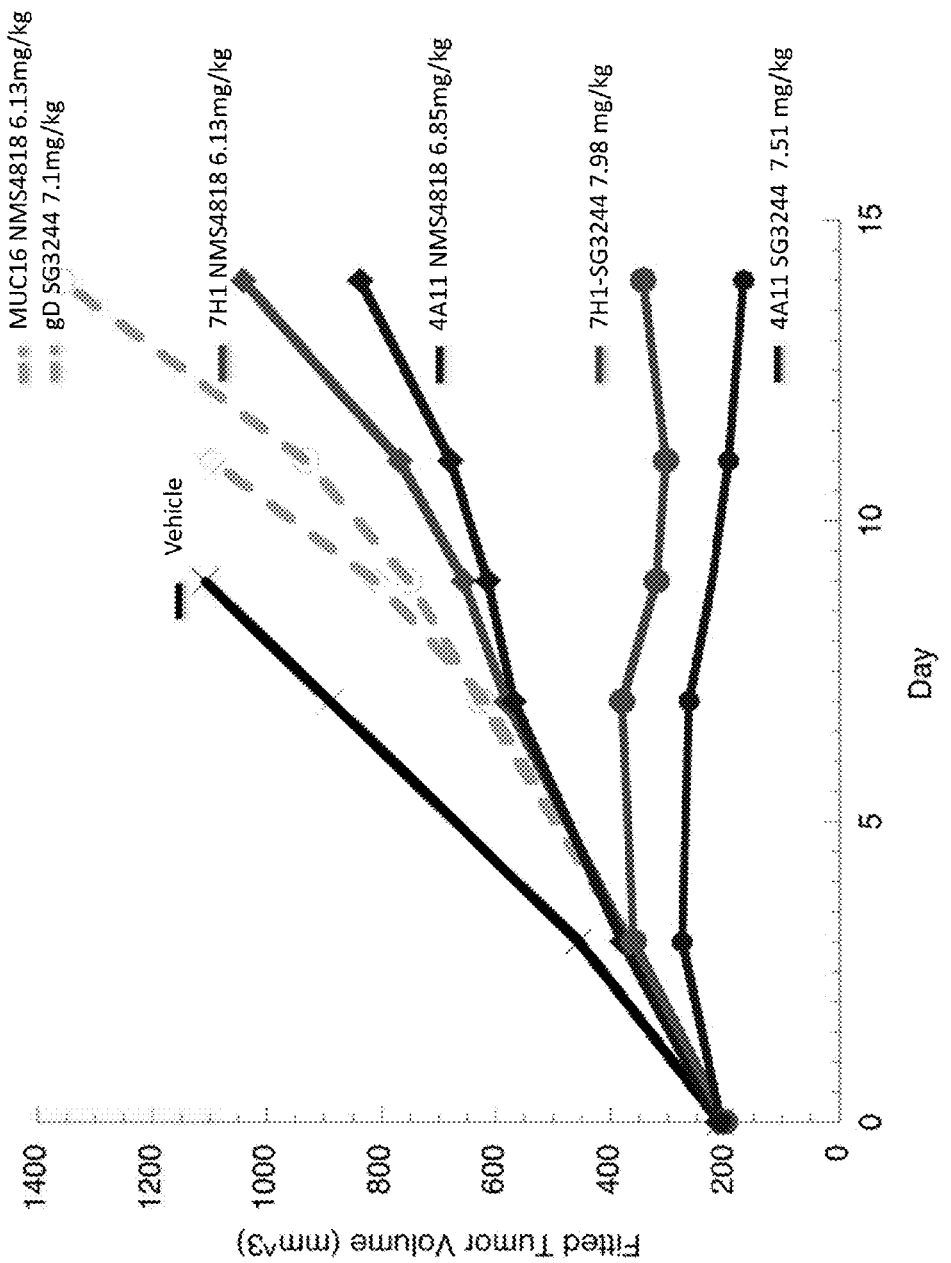
FIG. 16 shows change in tumor volume (mm$^3$) over time in a JHH7 xenograft model upon treatment with various antibody-drug conjugates, as described in Example 7.

As shown in FIG. 16, substantial tumor growth inhibition was achieved with both 7H1-disulfide-PBD (7.98 mg/kg) and 4A11 disulfide-PBD (7.51 mg/kg). The PNU conjugates (7H1-acetal-PNU and 4A11-acetal-PNU) were less efficacious in this experiment.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| NAME | SEQUENCE | SEQ ID NO |
|---|---|---|
| Human GPC3 (UniProt No. P51654) | MAGTVRTACL VVAMLLSLDF PGQAQPPPPP PDATCHQVRS FFQRLQPGLK WVPETPVPGS DLQVCLPKGP TCCSRKMEEK YQLTARLNME QLLQSASMEL KFLIIQNAAV FQEAFEIVVR HAKNYTNAMF KNNYPSLTPQ AFEFVGEFFT DVSLYILGSD INVDDMVNEL FDSLFPVIYT QLMNPGLPDS ALDINECLRG ARRDLKVFGN FPKLIMTQVS KSLQVTRIFL QALNLGIEVI NTTDHLKFSK DCGRMLTRMW YCSYCQGLMM VKPCGGYCNV VMQGCMAGVV EIDKYWREYI LSLEELVNGM YRIYDMENVL LGLFSTIHDS IQYVQKNAGK LTTTIGKLCA HSQQRQYRSA YYPEDLFIDK KVLKVAHVEH EETLSSRRRE LIQKLKSFIS FYSALPGYIC SHSPVAENDT LCWNGQELVE RYSQKAARNG MKNQFNLHEL KMKGPEPVVS QIIDKLKHIN QLLRTMSMPK GRVLDKNLDE EGFESGDCGD DEDECIGGSG DGMIKVKNQL RFLAELAYDL DVDDAPGNSQ QATPKDNEIS TFHNLGNVHS PLKLLTSMAI SVVCFFFLVH | 1 |
| 7H1 heavy chain variable region (VH) | QVQLQQSGPE LVKPGASVKI SCKASGYTFT DYYINWVKQK PGQGLEWIGW IYPGSGHTEC NETFKGKATL TVDTSSSTAY MQLSSLTSED TAVYFCTRGY YAPMGYFDYW GQGTTLTVSS | 2 |
| 7H1 light chain variable region (VL) | DIQMTQSPSS LSASLGERVS LTCRASQEIS GYLSWLQQKP DGTIKRLIYA ASTLDSGVPK RFSGSRSGSD YSLTISGLES EDFADYYCLQ YASYPYTFGG GTKLEIK | 3 |
| 7H1 HVR-H1 | DYYIN | 4 |
| 7H1 HVR-H2 | WIYPGSGHTECNETFKG | 5 |
| 7H1 HVR-H3 | GYYAPMGYFDY | 6 |
| 7H1 HVR-L1 | RASQEISGYLS | 7 |
| 7H1 HVR-L2 | AASTLDS | 8 |
| 7H1 HVR-L3 | LQYASYPYT | 9 |
| 4A11 heavy chain variable region (VH) | EVQLQQSAAE LARPGASVRM SCRTSGYTFT TYTIHWMKQR PGQGLEWIGY INPNGGYTEY NQKFRDRTTL TADKSSSTAY MQLSSLTSED SAVYYCTRNF DYWGQGTTLT VSS | 10 |
| 4A11 light chain variable region (VL) | DIVMTQSPSS MYASLGERVT ITCKASQDIN SYLSWFQQKP GKSPKTLIYR VNRLVDGVPS RFSGSGSGQD YSLTISSLEY EDVGIYYCLQ YDEFPLTLGA GTKLELK | 11 |
| 4A11 HVR-H1 | TYTIH | 12 |
| 4A11 HVR-H2 | YINPNGGYTEYNQKFRD | 13 |
| 4A11 HVR-H3 | NFDY | 14 |
| 4A11 HVR-L1 | KASQDINSYLS | 15 |
| 4A11 HVR-L2 | RVNRLVD | 16 |
| 4A11 HVR-L3 | LQYDEFPLT | 17 |
| 15G1 heavy chain variable region (VH) | EVQLLETGGG LVQPGGSRGL SCEGSGFTFS GFWMSWVRQT PGKTLEWIGD INSDGSSINY APSIKDRFTI FRDNDKSILY LQMTNVRSED TGTYFCVTTY GDYWGQGTTL TVSS | 18 |
| 15G1 light chain variable region (VL) | DIVMTQSQKF MSTSVGDRVS VTCKASQNVG SHVGWYQQKS GQSPKALIYS ASNRYIGVPD RFTGSGSGTD FTLTISNVQS EDLAEYFCQQ YHIYPYTFGG GTRLEIK | 19 |
| 15G1 HVR-H1 | GFWMS | 20 |
| 15G1 HVR-H2 | DINSDGSSINYAPSIKD | 21 |
| 15G1 HVR-H3 | TYGDY | 22 |
| 15G1 HVR-L1 | KASQNVGSHVG | 23 |
| 15G1 HVR-L2 | SASNRYI | 24 |

Table of Sequences

| NAME | SEQUENCE | SEQ ID NO |
|---|---|---|
| 15G1 HVR-L3 | QQYHIYPYT | 25 |
| 4G7 heavy chain variable region (VH) | EVQLQQSGTV LARPGASVKM SCKASGYTFT SYWVHWVKQR PGQGLEWIGA IYPGNIDASY NQKFKGKAKL TAVTSTSTAY MELSSLTNED SAVYYCSYDY DAWFVYWGQG TLVTVSA | 26 |
| 4G7 light chain variable region (VL) | DIQMTQSHKF MSTSVGDRVS ITCKASQDVS TAVAWYQQKP GQSPTLLIYS ASYRYTGVPD RFTGSGSGTD FTFTISSVQA EDLAVYYCQQ HYFTPRTFGG GTKLELK | 27 |
| 4G7 HVR-H1 | SYWVH | 28 |
| 4G7 HVR-H2 | AIYPGNIDASYNQKFKG | 29 |
| 4G7 HVR-H3 | DYDAWFVY | 30 |
| 4G7 HVR-L1 | KASQDVSTAVA | 31 |
| 4G7 HVR-L2 | SASYRYT | 32 |
| 4G7 HVR-L3 | QQHYFTPRT | 33 |
| V205C cysteine engineered light chain constant region (Igk) | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPCTKS FNRGEC | 34 |
| A118C cysteine engineered heavy chain constant region (IgG1) | CSTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK | 35 |
| S400C cysteine engineered heavy chain constant region (IgG1) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDCDGSFFLY SKLTVDKSRW QQGNVFSCSV MHEALHNHYT QKSLSLSPGK | 36 |
| Cynomolgus monkey GPC3 precursor; with signal sequence (1-24) UniProtKB/ Swiss-Prot: A5A6P7.1 | MAGTVRTACL VVAMLLSLDF PGAQPPPPP PDATCHQVRS FFQRLQPGLK WVPETPVPGS DLQVCLPKGP TCCSRKMEEK YQLTARLNME QLLQSASMEL KFLIIQNAAV FQEAFEIVVR HAKNYTNAMF KNNYPSLTPQ AFEFVGEFFT DVSLYILGSD INVDDMVNEL FDSLFPVIYT QLMNPGLPDS ALDINECLRG ARRDLKVFGN FPKLIMTQVS KSLQVTRIFL QALNLGIEVI NTTDHLKFSK DCGRMLTRMW YCSYCQGLMM VKPCGGYCNV VMQGCMAGVV EIDKYWREYI LSLEELVNGM YRIYDMENVL LGLFSTIHDS IQYVQKNAGK LTTTIGKLCA HSQQRQYRSA YYPEDLFIDK KVLKVAHVEH EETLSSRRRE LIQKLKSFIS FYSALPGYIC SHSPVAENDT LCWNGQELVE RYSQKAARNG MKNQFNLHEL KMKGPEPVVS QIIDKLKHIN QLLRTMSVPK GRVLDKNLDE EGFESGDCGD DEDECIGGSG DGMMKVKNQL RFLAELAYDL DVDDVPGNNQ QATPKDNEIS TFHNLGNVHS PLKLLTSMAI SVVCFFFLVH | 37 |
| Rhesus macaque GPC3 precursor; with signal sequence | MAGTVRTACL VVAMLLSLDF PGAQPPPPP PDATCHQVRS FFQRLQPGLK WVPETPVPGS DLQVCLPKGP TCCSRKMEEK YQLTARLNME QLLQSASMEL KFLIIQNAAV FQEAFEIVVR HAKNYTNAMF KNNYPSLTPQ AFEFVGEFFT DVSLYILGSD INVDDMVNEL FDSLFPVIYT QLMNPGLPDS ALDINECLRG ARRDLKVFGN FPKLIMTQVS KSLQVTRIFL QALNLGIEVI NTTDHLKFSK DCGRMLTRMW YCSYCQGLMM VKPCGGYCNV VMQGCMAGVV EIDKYWREYI LSLEELVNGM YRIYDMENVL LGLFSTIHDS IQYVQKNAGK LTTTIGKLCA HSQQRQYRSA YYPEDLFIDK KVLKVAHVEH EETLSSRRRE LIQKLKSFIS FYSALPGYIC SHSPVAENDT LCWNGQELVE RYSQKAARNG MKNQFNLHEL KMKGPEPVVS QIIDKLKHIN QLLRTMSVPK GRVLDKNLDE EGFESGDCGD DEDECIGGSG DGMMKVKNQL RFLAELAYDL DVDDVPGNNQ QATPKDNEIS TFHNLGNVHS PLKLLTSMAI SVVCFFFLVH | 38 |

Table of Sequences

| NAME | SEQUENCE | SEQ ID NO |
|---|---|---|
| Mouse GPC3 precursor; with signal sequence (1-24) UniProtKB/ Swiss-Prot: Q8CFZ4.1 | MAGTVRTACL LVAMLLGLGC LGQAQPPPPP DATCHQVRSF FQRLQPGLKW VPETPVPGSD LQVCLPKGPT CCSRKMEEKY QLTARLNMEQ LLQSASMELK FLIIQNAAVF QEAFEIVVRH AKNYTNAMFK NNYPSLTPQA FEFVGEFFTD VSLYILGSDI NVDDMVNELF DSLFPVIYTQ MMNPGLPESV LDINECLRGA RRDLKVFGSF PKLIMTQVSK SLQVTRIFLQ ALNLGIEVIN TTDHLKFSKD CGRMLTRMWY CSYCQGLMMV KPCGGYCNVV MQGCMAGVVE IDKYWREYIL SLEELVNGMY RIYDMENVLL GLFSTIHDSI QYVQKNGGKL TTTIGKLCAH SQQRQYRSAY YPEDLFIDKK ILKVAHVEHE ETLSSRRREL IQKLKSFINF YSALPGYICS HSPVAENDTL CWNGQELVER YSQKAARNGM KNQFNLHELK MKGPEPVVSQ IIDKLKHINQ LLRRTMSVPKG KVLDKSLDEE GLESGDCGDD EDECIGSSGD GMVKVKNQLR FLAELAYDLD VDDAPGNKQH GNQKDNEITT SHSVGNMPSP LKILISVAIY VACFFFLVH | 39 |
| Rat GPC3 precursor; with signal sequence (1 to 24) | MAGTVRTACL LVAMLLGLGC LGQAQPPPPP DATCHQVRSF FQRLQPGLKW VPETPVPGSD LQVCLPKGPT CCSRKMEEKY QLTARLNMEQ LLQSASMELK FLIIQNAAVF QEAFEIVVRH AKNYTNAMFK NNYPSLTPQA FEFVGEFFTD VSLYILGSDI NVDDMVNELF DSLFPVIYTQ MMNPGLPESV LDINECLRGA RRDLKVFGSF PKLIMTQVSK SLQVTRIFLQ ALNLGIEVIN TTDHLKFSKD CGRMLTRMWY CSYCQGLMMV KPCGGYCNVV MQGCMAGVVE IDKYWREYIL SLEELVNGMY RIYDMENVLL GLFSTIHDSI QYVQKNGGKL TTTIGKLCAH SQQRQYRSAY YPEDLFIDKK VLKVARVEHE ETLSSRRREL IQKLKSFISF YSALPGYICS HSPVAENDTL CWNGQELVER YSQKAARNGM KNQFNLHELK MKGPEPVVSQ IIDKLKHINQ LLRTMSVPKG KVVDKSLDEE GLESGDCGDD EDECIGSSGD GMMKVKNQLR FLAELAYDLD VDDAPGNKQH GNQKDNEITT SHSVGNMPSP LKILISVAIY VACFFFLVH | 40 |
| HSV signal sequence gD (HSV ss gD) | MGGTAARLGA VILFVVIVGL HGVRGKYALA DASLKMADPN RFRGKDLPVL | 41 |
| 7H1 IgG1 heavy chain | QVQLQQSGPE LVKPGASVKI SCKASGYTFT DYYINWVKQK PGQGLEWIGW IYPGSGHTEC NETFKGKATL TVDTSSSTAY MQLSSLTSED TAVYFCTRGY YAPMGYFDYW GQGTTLTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK | 42 |
| 7H1 A118C IgG1 heavy chain | QVQLQQSGPE LVKPGASVKI SCKASGYTFT DYYINWVKQK PGQGLEWIGW IYPGSGHTEC NETFKGKATL TVDTSSSTAY MQLSSLTSED TAVYFCTRGY YAPMGYFDYW GQGTTLTVSS CSTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK | 43 |
| 7H1 kappa light chain | DIQMTQSPSS LSASLGERVS LTCRASQEIS GYLSWLQQKP DGTIKRLIYA ASTLDSGVPK RFSGSRSGSD YSLTISGLES EDFADYYCLQ YASYPYTFGG GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC | 44 |
| 4A11 A118C IgG1 heavy chain | EVQLQQSAAE LARPGASVRM SCRTSGYTFT TYTIHWMKQR PGQGLEWIGY INPNGGYTEY NQKFRDRTTL TADKSSSTAY MQLSSLTSED SAVYYCTRNF DYWGQGTTLT VSSCSTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PGK | 45 |
| 4A11 kappa light chain | DIVMTQSPSS MYASLGERVT ITCKASQDIN SYLSWFQQKP GKSPKTLIYR VNRLVDGVPS RFSGSGSGQD YSLTISSLEY EDVGIYYCLQ YDEFPLTLGA GTKLELKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC | 46 |

Table of Sequences

| NAME | SEQUENCE | SEQ ID NO |
|---|---|---|
| 15G1 A118C IgG1 heavy chain | EVQLLETGGG LVQPGGSRGL SCEGSGFTFS GFWMSWVRQT PGKTLEWIGD INSDGSSINY APSIKDRFTI FRDNDKSILY LQMTNVRSED TGTYFCVTTY GDYWGQGTTL TVSSCSTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE LLGGPSVFLF PPKPKDTLMI SRTPEVTCVV VDVSHEDPEV KFNWYVDGVE VHNAKTKPRE EQYNSTYRVV SVLTVLHQDW LNGKEYKCKV SNKALPAPIE KTISKAKGQP REPQVYTLPP SREEMTKNQV SLTCLVKGFY PSDIAVEWES NGQPENNYKT TPPVLDSDGS FFLYSKLTVD KSRWQQGNVF SCSVMHEALH NHYTQKSLSL SPGK | 47 |
| 15G1 kappa light chain | DIVMTQSQKF MSTSVGDRVS VTCKASQNVG SHVGWYQQKS GQSPKALIYS ASNRYIGVPD RFTGSGSGTD FTLTISNVQS EDLAEYFCQQ YHIYPYTFGG GTRLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC | 48 |

What is claimed is:

1. An isolated antibody that binds human GPC3, wherein the antibody comprises HVR-H1 comprising the amino acid sequence of SEQ ID NO: 28, HVR-H2 comprising the amino acid sequence of SEQ ID NO: 29, HVR-H3 comprising the amino acid sequence of SEQ ID NO: 30, HVR-L1 comprising the amino acid sequence of SEQ ID NO: 31, HVR-L2 comprising the amino acid sequence of SEQ ID NO: 32, and HVR-L3 comprising the amino acid sequence of SEQ ID NO: 33.

2. The antibody of claim 1, wherein the antibody binds to an epitope spanning the furin cleavage site at amino acids R358/S359 of human GPC3 of SEQ ID NO: 1.

3. The antibody of claim 2, wherein the antibody binds to full-length mature human GPC3 but does not bind to an N-terminal fragment of human GPC3 consisting of amino acids 25 to 358 of SEQ ID NO: 1, and does not bind to a C-terminal fragment of human GPC3 consisting of amino acids 359 to 560 or amino acids 359 to 580 of SEQ ID NO: 1.

4. The antibody of claim 1, wherein the antibody comprises:
   a) a VH sequence having at least 95% sequence identity to the amino acid sequence of SEQ ID NO: 26;
   b) a VL sequence having at least 95% sequence identity to the amino acid sequence of SEQ ID NO: 27;
   c) a VH sequence having the amino acid sequence of SEQ ID NO: 26;
   d) a VL sequence having the amino acid sequence of SEQ ID NO: 27;
   e) a VH as in (a) or (c), and a VL as in (b) or (d).

5. The antibody of claim 1, which is a monoclonal antibody.

6. The antibody of claim 1, which is a human, humanized, or chimeric antibody.

7. The antibody of claim 1, which is an antibody fragment that binds human GPC3.

8. The antibody of claim 1, wherein the human GPC3 comprises amino acids 25 to 580 of SEQ ID NO: 1.

9. The antibody of claim 1, which is an IgG1, IgG2a or IgG2b antibody.

10. An immunoconjugate comprising the antibody of claim 1 and a cytotoxic agent.

11. The immunoconjugate of claim 10 having the formula Ab-(L-D)p, wherein:
 (a) Ab is the antibody;
 (b) L is a linker;
 (c) D is a cytotoxic agent; and
 (d) p ranges from 1-8.

12. The immunoconjugate of claim 11, wherein the cytotoxic agent is selected from a maytansinoid, a calicheamicin, a pyrrolobenzodiazepine, and a nemorubicin derivative.

13. The immunoconjugate of claim 11, wherein D is a pyrrolobenzodiazepine of Formula A:

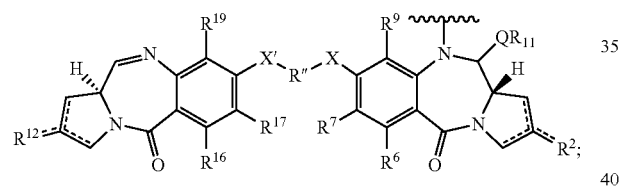

A wherein the dotted lines indicate the optional presence of a double bond between C1 and C2 or C2 and C3;
$R^2$ is independently selected from H, OH, =O, =CH$_2$, CN, R, OR, =CH—$R^D$, =C($R^D$)$_2$, OSO$_2$R, CO$_2$R and COR, and optionally further selected from halo or dihalo, wherein $R^D$ is independently selected from R, CO$_2$R, COR, CHO, CO$_2$H, and halo;
$R^6$ and $R^9$ are independently selected from H, R, OH, OR, SH, SR, NH$_2$, NHR, NRR', NO$_2$, Me$_3$Sn and halo;
$R^7$ is independently selected from H, R, OH, OR, SH, SR, NH$_2$, NHR, NRR', NO$_2$, Me$_3$Sn and halo;
Q is independently selected from O, S and NH;
$R^{11}$ is either H, or R or, where Q is O, SO$_3$M, where M is a metal cation;
R and R' are each independently selected from optionally substituted C$_{1-8}$ alkyl, C$_{3-8}$ heterocyclyl and C$_{5-20}$ aryl groups, and optionally in relation to the group NRR', R and R' together with the nitrogen atom to which they are attached form an optionally substituted 4, 5, 6 or 7 membered heterocyclic ring;
$R^{12}$, $R^{16}$, $R^{19}$ and $R^{17}$ are as defined for $R^2$, $R^6$, $R^9$ and $R^7$ respectively;
R" is a C$_{3-12}$ alkylene group, which chain may be interrupted by one or more heteroatoms and/or aromatic rings that are optionally substituted; and
X and X' are independently selected from O, S and N(H).

14. The immunoconjugate of claim 13, wherein D has the structure:

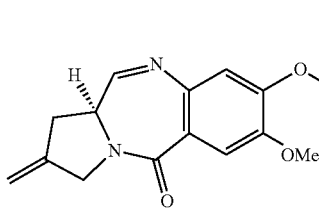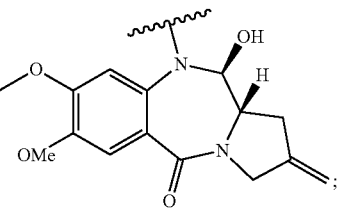

wherein n is 0 or 1.

15. The immunoconjugate of claim 11, wherein D is a nemorubicin derivative.

16. The immunoconjugate of claim 15, wherein D has a structure selected from:

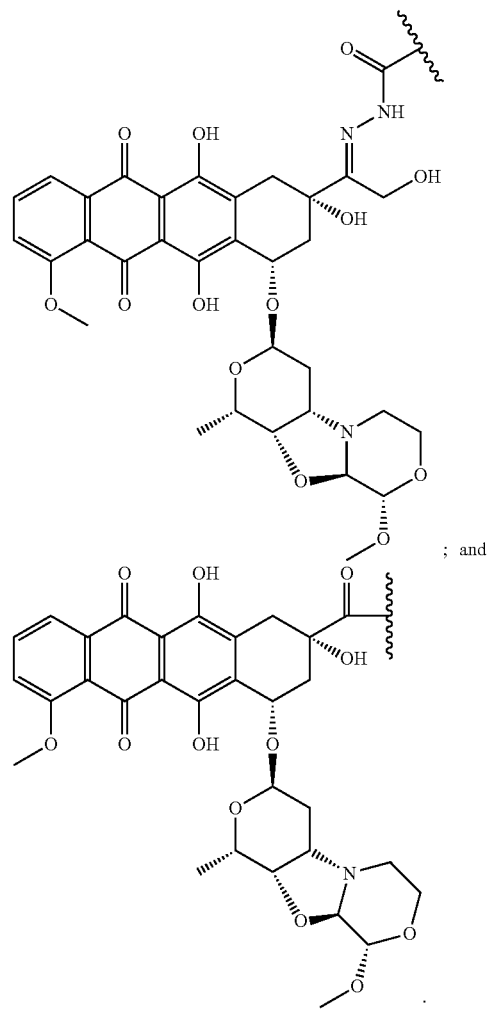

17. The immunoconjugate of claim 11, wherein the linker is cleavable by a protease.

18. The immunoconjugate of claim 11, wherein the linker is acid-labile.

19. The immunoconjugate of claim 18, wherein the linker comprises hydrazone.

20. The immunoconjugate of claim 11 having a formula selected from:

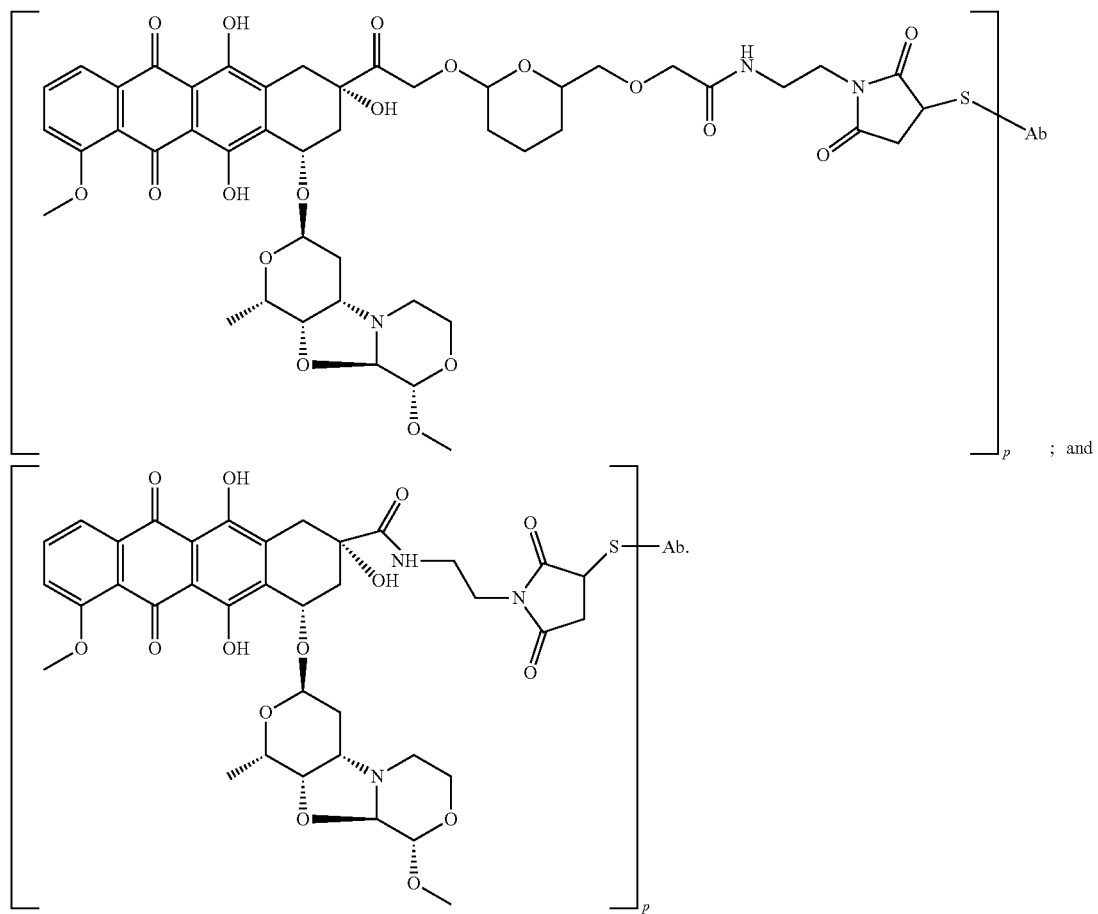

21. The immunoconjugate of claim 11, wherein p ranges from 2-5.

22. A pharmaceutical formulation comprising the immunoconjugate of claim 10 and a pharmaceutically acceptable carrier.

23. A pharmaceutical formulation comprising the antibody of claim 1 and a pharmaceutically acceptable carrier.

24. The antibody of claim 1 conjugated to a label.

25. The antibody of claim 24, wherein the label is a positron emitter.

26. The antibody of claim 25, wherein the positron emitter is $^{89}Zr$.

* * * * *